US011492636B2

(12) United States Patent
Christ et al.

(10) Patent No.: US 11,492,636 B2
(45) Date of Patent: Nov. 8, 2022

(54) MODIFIED BIALAPHOS RESISTANCE ACETYLTRANSFERASE COMPOSITIONS AND USES THEREOF

(71) Applicant: Whitehead Institute for Biomedical Research, Cambridge, MA (US)

(72) Inventors: Bastien Christ, Cambridge, MA (US); Jing-Ke Weng, Belmont, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 107 days.

(21) Appl. No.: 16/340,579

(22) PCT Filed: Oct. 17, 2017

(86) PCT No.: PCT/US2017/056968
§ 371 (c)(1),
(2) Date: Apr. 9, 2019

(87) PCT Pub. No.: WO2018/075507
PCT Pub. Date: Apr. 26, 2018

(65) Prior Publication Data
US 2019/0249188 A1  Aug. 15, 2019

Related U.S. Application Data

(60) Provisional application No. 62/409,087, filed on Oct. 17, 2016.

(51) Int. Cl.
*C12N 15/82* (2006.01)
*C12N 9/10* (2006.01)

(52) U.S. Cl.
CPC ....... *C12N 15/8277* (2013.01); *C12N 9/1029* (2013.01); *C12N 15/8209* (2013.01); *C12Y 203/01183* (2013.01)

(58) Field of Classification Search
CPC .................................. C12N 15/8277
See application file for complete search history.

(56) References Cited

FOREIGN PATENT DOCUMENTS

| WO | 2004/042059 A1 | 5/2004 |
|----|----------------|--------|
| WO | 2009/152359 A2 | 12/2009 |
| WO | 2014/116854 A1 | 7/2014 |

OTHER PUBLICATIONS

Christ et al, Nature Plants (2017) 3:937-945.*
Ng et al, Annual Rev. Genomics Hum. Genetics (2006) 61-80.*
UniProt Accession No. P16426, Integrated Into UniProton Aug. 1, 1990.*
Christ, B. et al., "Non-specific activities of the major herbicide-resistance gene BAR," Nature Plants, vol. 3; 937-945 (2017).
Geneseq, "Phosphinothricin acetyltransferase (BAR) protein SEQ ID No. 124," retrieved from EBI accession No. GSP: AD026731; 1 page (2004).
Notification and Transmittal of the International Search Report and Written Opinion for International Application No. PCT/US2017/056968, entitled: "Modified Bialaphos Resistance Acetyltransferase Compositions and Uses Thereof," dated Feb. 12, 2018.
Notification Concerning Transmittal of International Preliminary Report on Patentability for International Application No. PCT/US2017/056968, titled: "Modified Bialaphos Resistance Acetyltransferase Compositions and Uses Thereof," dated May 2, 2019.

* cited by examiner

*Primary Examiner* — Mykola V. Kovalenko
(74) *Attorney, Agent, or Firm* — Hamilton, Brook, Smith & Reynolds, P.C.

(57) ABSTRACT

Provided herein are engineered bialaphos resistance acetyltransferase variants having a modified acetyltransferase activity against tryptophan or aminoadipate, or both, as compared to a wildtype bialaphos resistance acetyltransferase (e.g., BAR or PAT). Also provided are transgenic plants comprising a bialaphos resistance acetyltransferase variant as well as methods of making such transgenic plants.

11 Claims, 33 Drawing Sheets

Specification includes a Sequence Listing.

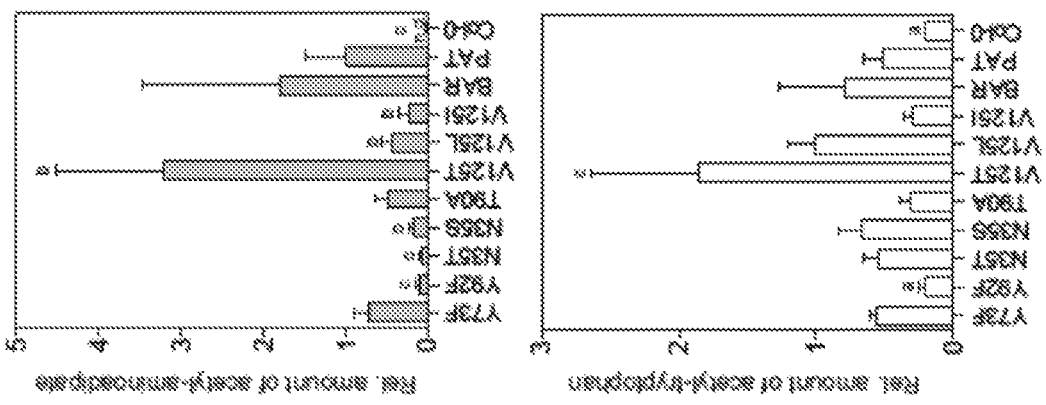
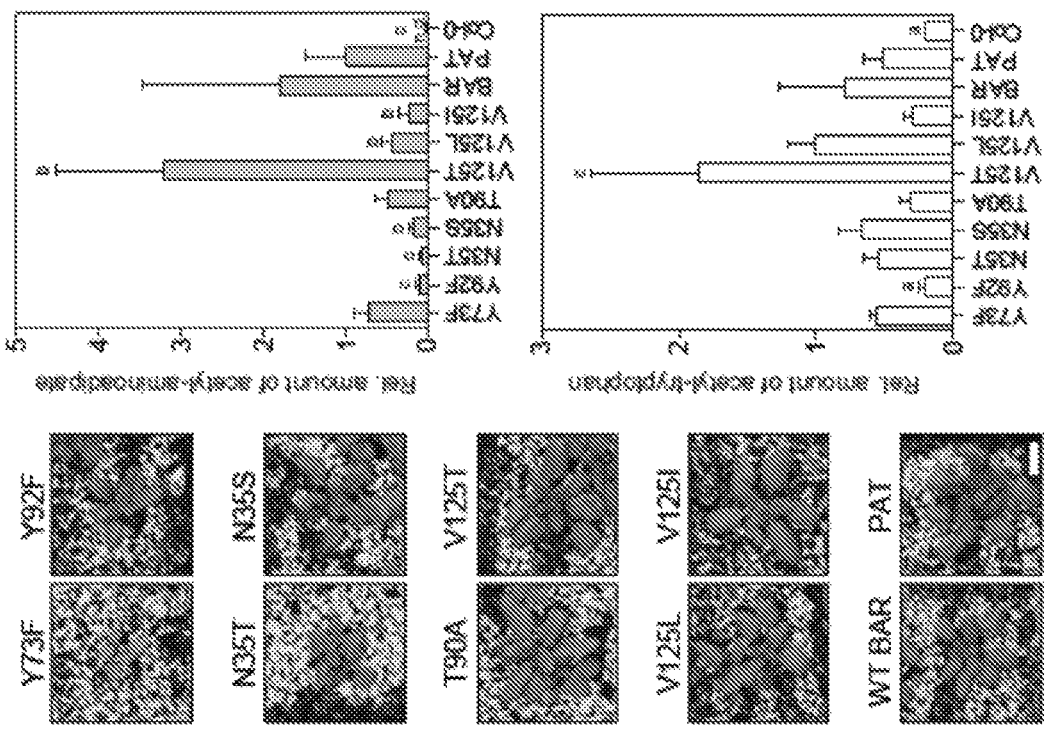

MODIFIED BIALAPHOS RESISTANCE ACETYLTRANSFERASE COMPOSITIONS AND USES THEREOF

RELATED APPLICATION

This application is the U.S. National Stage of International Application No. PCT/US2017/056968, filed Oct. 17, 2017, which designates the U.S., published in English, which claims the benefit of U.S. Provisional Application No. 62/409,087, filed on Oct. 17, 2016. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 03992059003 SequenceListing.txt; created Apr. 5, 2019, 40 KB in size.

BACKGROUND

Transgenic expression of enzymes catalyzing desirable metabolic traits in heterologous hosts is a widespread approach in both basic biological research and translational biotechnology. Prominent examples include reporter enzymes, such as firefly luciferase and β-glucuronidase, antibiotic/herbicide markers, and many enzymes used for metabolic engineering purposes in microbes and higher eukaryotes (Woolston, B. M. et al., *Annual review of chemical and biomolecular engineering* 4, 259-288 (2013)). Although enzymes are generally considered as perfected catalysts with superior substrate specificity and predictable catalytic mechanism, increasing evidence has raised awareness of the unpredictable behaviors of enzymes and their profound implication in natural and directed evolution of new enzymatic functions (Weng, J. K. and Noel, J. P. *Cold Spring Harbor Symposia on Quantitative Biology* 77, 309-320 (2012)).

Herbicide resistance is a major trait of genetically modified plants. Resistance to the herbicide glufosinate, a naturally occurring herbicide derived from the tripeptide antibiotic bialaphos, is achieved by transgenic expression of a bialaphos resistance enzyme (e.g., bacterial acetyltransferase (BAR) and phosphinothricin acetyltransferase (PAT)), which inactivates glufosinate through N-acetylation. Given the wide application of phosphinothricin resistance in genetically modified plants, methods for ensuring predictability of bialaphos resistance enzymatic activity are needed.

SUMMARY OF THE INVENTION

The herbicide-resistance enzyme, generically referred to as bialaphos resistance acetyltransferase (e.g., BAR or PAT) interferes with plant amino acid metabolism through its promiscuous activities. The present invention provides methods for repressing such undesirable activities through structure-guided enzyme engineering.

In one aspect, the present invention relates to a nucleic acid encoding a bialaphos resistance (BAR) protein variant, wherein the BAR protein variant possesses a modified acetyltransferase activity against tryptophan or aminoadipate, or both, as compared to a wildtype BAR protein (e.g., comprising the sequence set forth in SEQ ID NO: 1).

In another aspect, the present invention relates to a nucleic acid encoding a phosphinothricin acetyltransferase (PAT) variant, wherein the PAT variant possesses a modified acetyltransferase activity against tryptophan or aminoadipate, or both, as compared to a wildtype PAT protein (e.g., comprising the sequence set forth in SEQ ID NO: 2).

In other aspects, the present invention relates to a method of generating a transgenic plant. The method comprises introducing into a plant a nucleic acid encoding a BAR protein variant, wherein the BAR protein variant possesses a modified acetyltransferase activity against tryptophan or aminoadipate, or both, as compared to a wildtype BAR protein (e.g., comprising the sequence set forth in SEQ ID NO: 1). In a particular embodiment, the method also comprises integrating the nucleic acid into the genome of the plant, thereby generating a transgenic plant.

In other aspects, the present invention relates to a method of generating a transgenic plant. The method comprises introducing into a plant a nucleic acid encoding a PAT protein variant, wherein the PAT variant possesses a modified acetyltransferase activity against tryptophan or aminoadipate, or both, as compared to a wildtype PAT protein (e.g., comprising the sequence set forth in SEQ ID NO: 2). In a particular embodiment, the method also comprises integrating the nucleic acid into the genome of the plant, thereby generating a transgenic plant.

In further aspects, the present invention relates to a transgenic plant comprising a nucleic acid encoding a BAR protein variant, wherein the BAR protein variant possesses a modified acetyltransferase activity against tryptophan or aminoadipate, or both, as compared to a wildtype BAR protein (e.g., comprising the sequence set forth in SEQ ID NO: 1).

In another aspect, the present invention relates to a transgenic plant comprising a nucleic acid encoding a PAT protein variant, wherein the PAT protein variant possesses a modified acetyltransferase activity against tryptophan or aminoadipate, or both, as compared to a wildtype PAT protein (e.g., comprising the sequence set forth in SEQ ID NO: 2).

The present invention provides new methods for improving the substrate specificity of bialaphos resistance acetyltransferase (e.g., BAR or PAT) and/or preventing or reducing formation of non-native metabolites.

BRIEF DESCRIPTION OF THE DRAWINGS

FIG. 1A. Metabolite profiles of senescent leaves from Wassilewskija (Ws) and clh2-1 (FLAG_076H05), displayed as base peak chromatograms (BPC), reveal the ectopic accumulation of acetyl-aminoadipate (1) and acetyl-tryptophan (2). FIG. 1B. Relative quantification of acetyl-aminoadipate and absolute quantification of acetyl-tryptophan in *Arabidopsis* mutants from different insertional mutant collections that contain either BAR (SAIL and FLAG) or alternative selection marker genes (SALK and GABI). FW, fresh weight; n.d., not detected.

FIG. 2A. Aminoadipate is derived from the lysine degradation pathway in plants, which can be metabolized by BAR as a promiscuous substrate. FIG. 2B Quantification of acetyl-aminoadipate and acetyl-tryptophan in green and senescent leaves from the heterozygous (Hz) and homozygous (Ho) FLAG_lkrsdh mutant, harboring a BAR-containing T-DNA that abolishes the *Arabidopsis* LKR/SDH gene. Ws, Wassilewskija wild-type plants; n.d., not detected.

FIG. 3A An apparent KM value of 39±7.6 µM was obtained for phosphinothricin, similar to previously published data (Thompson, C. J. et al., *The EMBO J.* 6, 2519-2523 (1987); Wehrmann, A. et al., *Nature Biotech.* 14, 1274-1278 (1996); Vinnemeier, J. et al., *Zeitschrift Fur Naturforschung Section C-a Journal of Biosciences* 50, 796-805 (1995)). FIG. 3B. Aminoadipate and tryptophan are in vitro substrates of BAR. Both substrates reached solubility limit before reaching saturation concentration for BAR. Negative controls (open square for aminoadipate and open circle for tryptophan) were performed in absence of BAR at the highest substrate concentration tested at 8.4 mM.

FIGS. 4A-4G. Structural basis for amino acid N-acetylation catalyzed by BAR and structure-guided engineering of BAR with reduced promiscuous activities. FIG. 4A. Cartoon representation of BAR homodimer in complex with phosphinothricin and CoA. Two monomers of the dimer are colored in blue and yellow respectively. FIG. 4B. Close-up view of the BAR active site. The |2Fo-Fc| omit electron density map (contoured at 3.0 σ) is shown for phosphinothricin. FIG. 4C. Proposed catalytic mechanism of BAR. FIG. 4D. Docking of tryptophan and aminoadipate within the BAR active site reveals reduced favorable contacts compared to phosphinothricin. FIG. 4E. Enzyme activity assays using purified BAR mutant proteins against phosphinothricin, aminoadipate and tryptophan as substrates. Error bars represent standard deviation of triplicate assays. Wild-type BAR (WT BAR) and PAT from *Streptomyces viridochromogenes* were also examined as controls. The relative activity is displayed based on activities measured in WT BAR. FIG. 4F. Photographs of *Arabidopsis* T1 lines transformed with select BAR mutants 20 days after phosphinothricin treatment. Scale bar=0.5 cm. FIG. 4G. Levels of acetyl-aminoadipate and acetyl-tryptophan in phosphinothricin-resistant T1 *Arabidopsis* plants transformed with select BAR mutants. Error bars represent standard deviation of biological quadruplets. Significance levels were indicated based on one-way ANOVA with Dunnett's test for multiple comparisons to WT BAR. a, p-value<0.1; b, p-value<0.05; c, p-value<0.01.

FIG. 7A. Photograph of wild-type and phosphinothricin-resistant *Glycine max* taken 14 days after herbicide treatment. Scale bar=2 cm. FIG. 7B. Relative quantification of acetyl-aminoadipate and acetyl-tryptophan in seeds, green leaves and senescent leaves of wild-type and phosphinothricin-resistant *Glycine max* (LL). Note that wild-type *Glycine max* has been shown to accumulate acetyl-tryptophan naturally (Yu, P. et al., *The Plant journal: for cell and molecular biology* 79, 1065-1075 (2014)). FIG. 7C. Relative quantification of acetyl-aminoadipate and acetyl-tryptophan in seeds, green leaves and senescent leaves of wild-type and phosphinothricin-resistant *Brassica juncea* (lines #5 and #7, (Song, W. Y. et al., *PNAS* 108, 19808-19813 (2011)).

FIG. 8A. BAR expression and purification was monitored by SDS-PAGE. The 6×His-BAR protein fusion was isolated from the *E. coli* lysate (lane 1, uninduced cells; lane 2, induced cells; lane 3, soluble proteins; lane 4, insoluble proteins) by metal affinity chromatography (Ni2+-charged HisTrap (GE Healthcare); lane 5, flow-through; lane 6, 6×His-BAR elution). Partially purified 6×His-BAR protein fusion was then treated with 6×His-TEV protease (Tropea, J. E., et al. *Methods Mol. Biol.* 498, 297-307 (2009)) and passed through the HisTrap to remove the His-tag (lane 7, flow-through; lane 8, elution of 6×His-TEV and uncut 6×His-BAR) and further purified by gel exclusion chromatography (lane 9). Time-dependent activities of purified 6×His-BAR were determined at substrate concentration of 100 µM for phosphinothricin (FIG. 8B) and 400 µM for aminoadipate (FIG. 8C) and tryptophan (FIG. 8D).

FIG. 9A. Diagram showing two views of the alignment performed using the SSM structural alignment function under Coot (Adams, P. D. et al., *Acta crystallographica. Section D, Biological crystallography* 66, 213-221 (2010)). FIG. 9B. Close-up view of the active site.

FIG. 10A. Each asymmetric unit (ASU) is constituted of one homodimer and two monomers that form homodimer with chains from neighboring cells (shown as transparent chains). FIG. 10B. Surface representation of BAR revealing a large open cavity at the dimer interface.

FIG. 11A. Close-up of view of the active site of BAR. FIG. 11B. Diagram showing the residues involved in catalysis. Distances are shown in Angstroms.

(SEQ ID NO: 90); *Streptomyces xiamenensis* (SEQ ID NO: 91), AKG45686; *Salinispora tropica*, WP_028566484 (SEQ ID NO: 92); *Owenweeksia hongkongensis*, WP_014202881 (SEQ ID NO: 93); *Vibrio diazotrophicus*, WP_042485812 (SEQ ID NO: 94); *Alcaligenes faecalis*, CAA00175 (SEQ ID NO: 95); *Sphingomonas wittichii*: WP_037526498 (SEQ ID NO: 96); *Ponticaulis koreensis*, WP_022694195 (SEQ ID NO: 97); *Pseudomonas syringae*, WP_032656505 (SEQ ID NO: 98); *Sphingobium herbicidovorans*, WP_037462269 (SEQ ID NO: 99).

Figure 14:
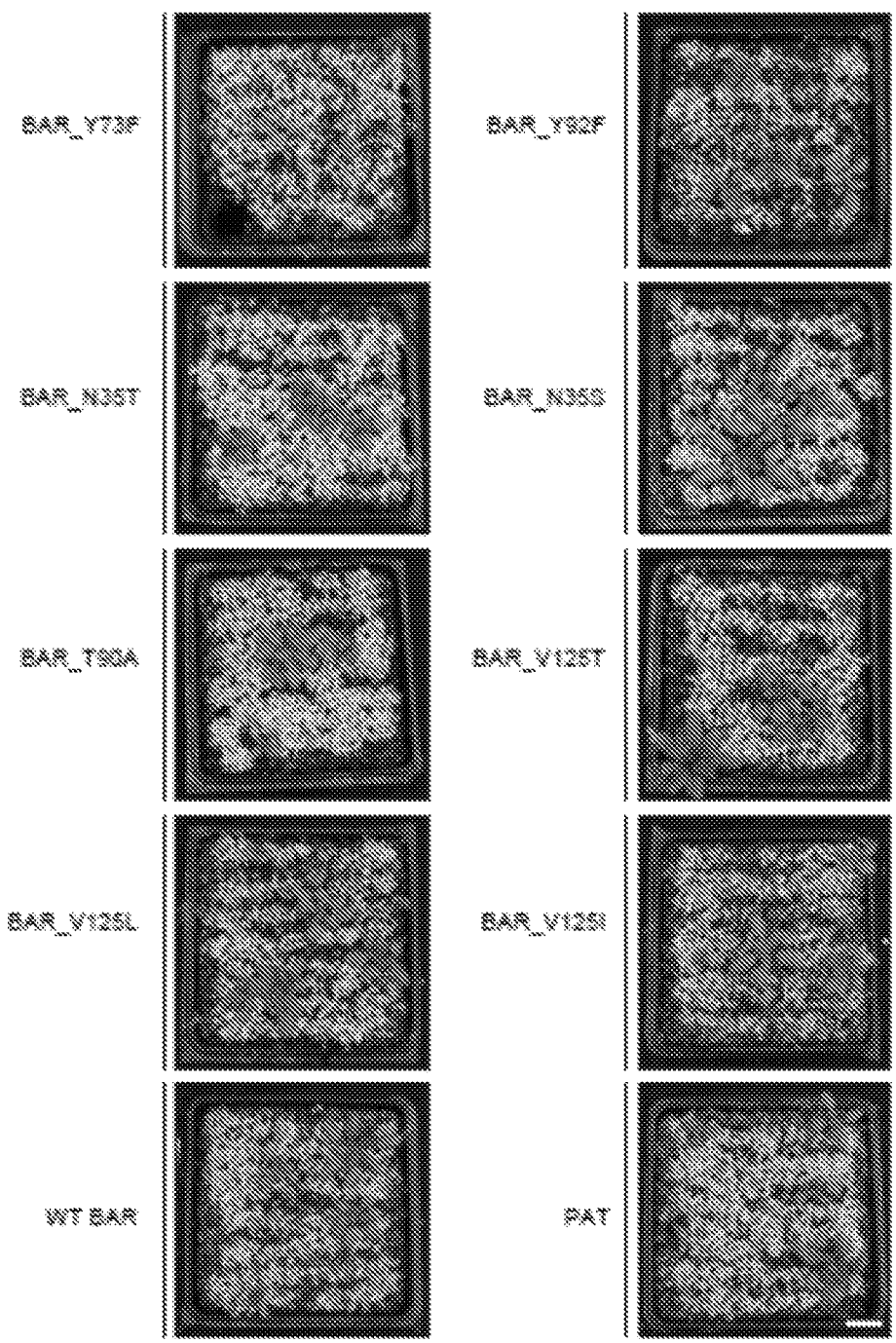

FIG. 14. Photographs of *Arabidopsis* T1 lines transformed with WT BAR, PAT from *Streptomyces viridochromogenes* and selected BAR mutants taken 20 days after phosphinothricin treatment. Scale bar=1 cm.

Figure 15A:
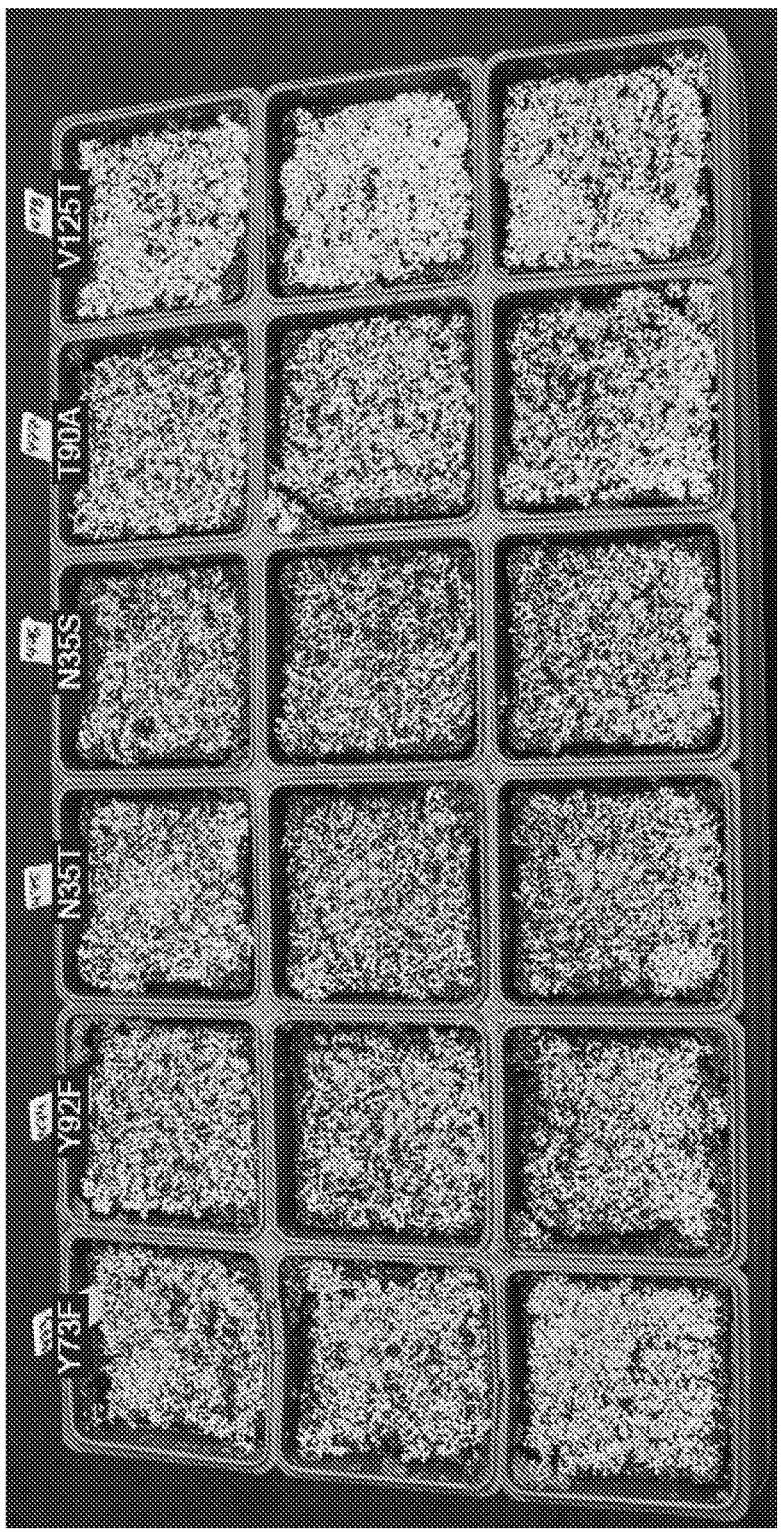
Figure 15B:
Figure 16A:
Figure 16B:
Figure 16C:
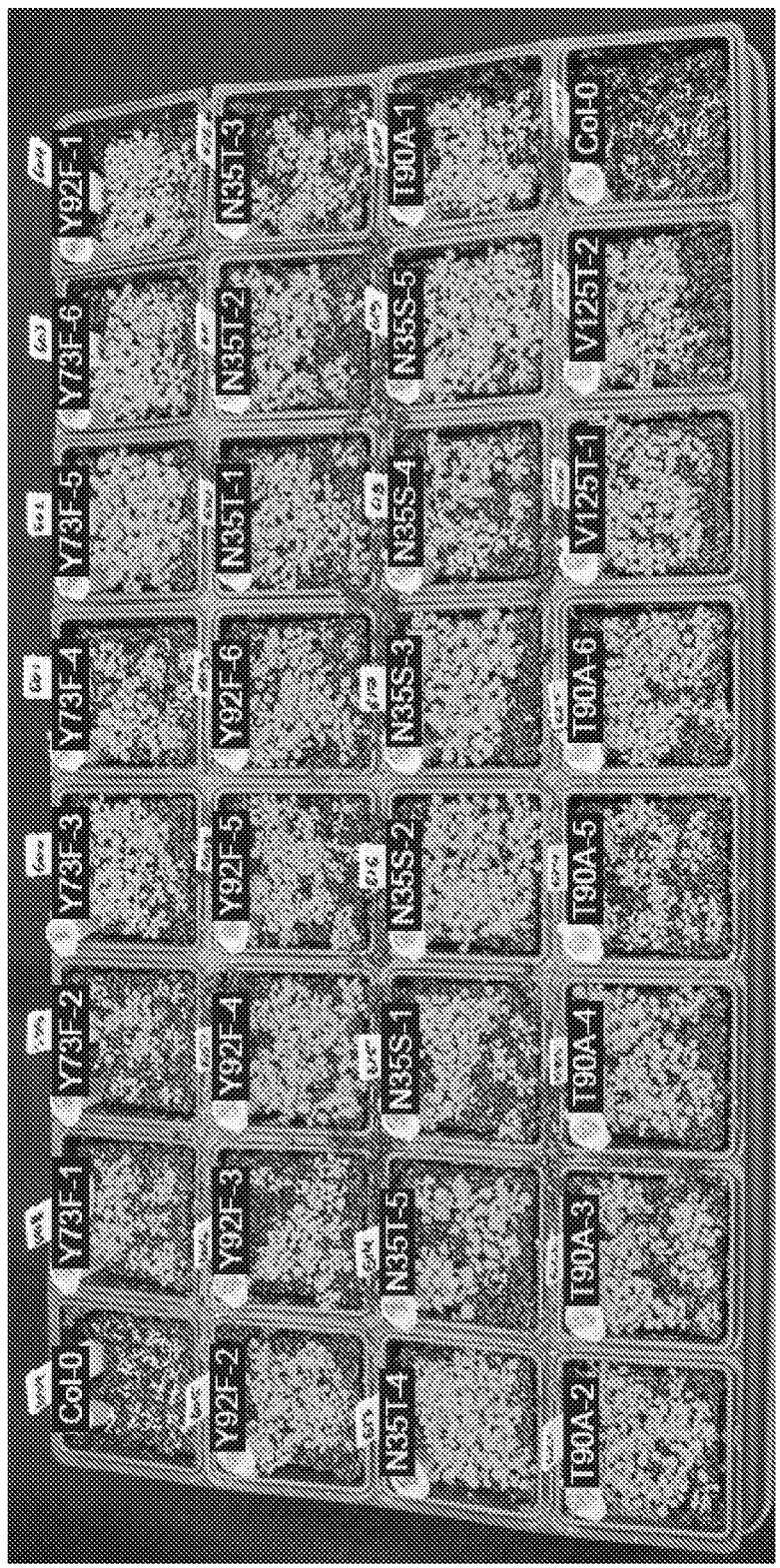
Figure 16D:

FIGS. 15A-15B. Selection of T1 transgenic *Arabidopsis* transformed with BAR variants. Photographs of *Arabidopsis* T1 lines transformed with wild-type BAR from *Streptomyces hygroscopicus* (WT BAR), PAT from *Streptomyces viridochromogenes* and selected BAR mutants taken 10 days after Finale® application. Scale bar=1 cm.

FIGS. 16A-16D. Resistance to phosphinothricin of T2 transgenic *Arabidopsis* transformed with BAR variants. 7-day old transgenic T2 plants were sprayed with Finale® and further grown for 8 days. Photographs were taken before (FIGS. 16A and 16B) and after (FIGS. 16C and 16D) Finale® application. Scale bar=1 cm.

Figure 17A:
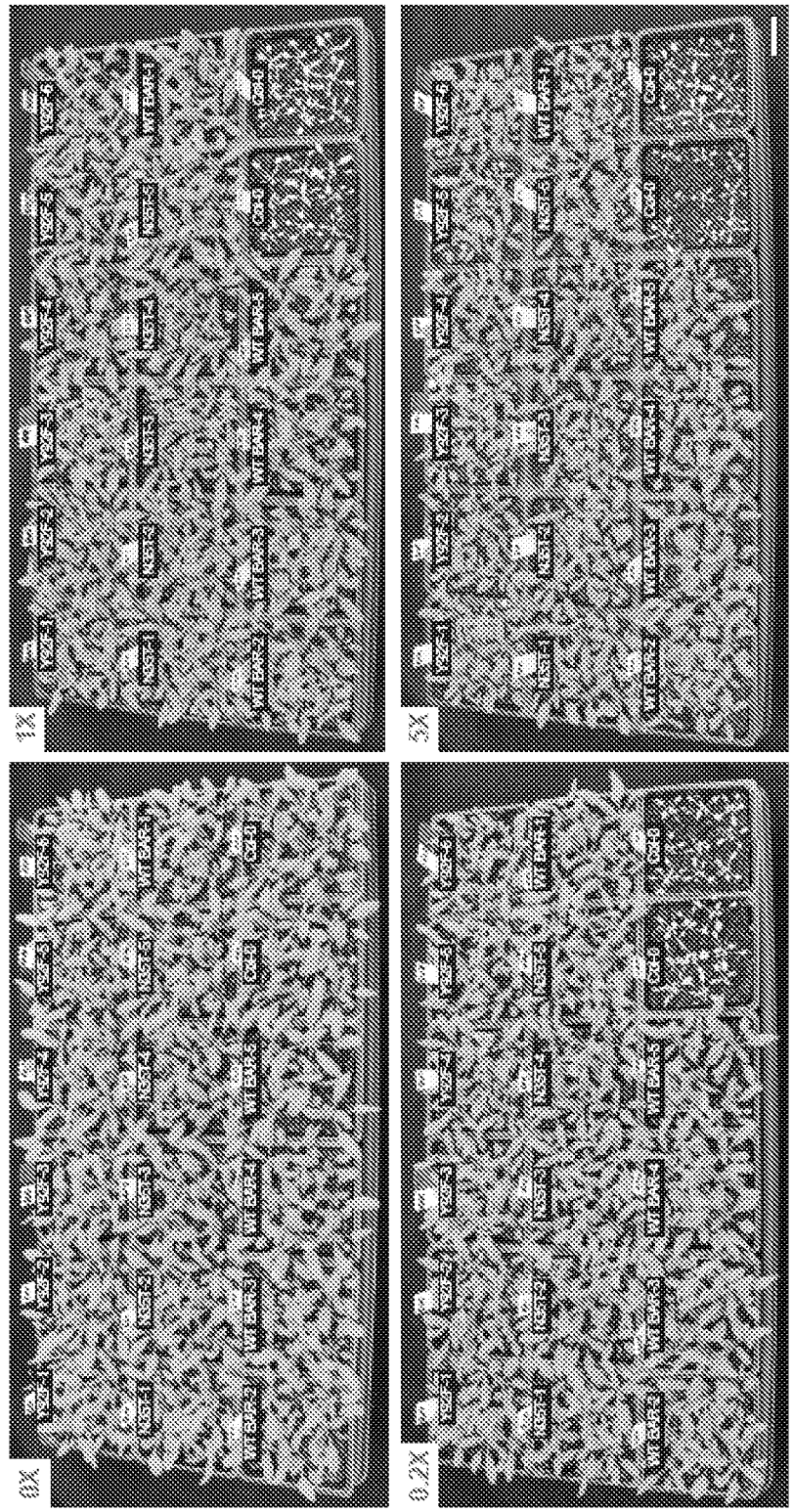
Figure 17B:
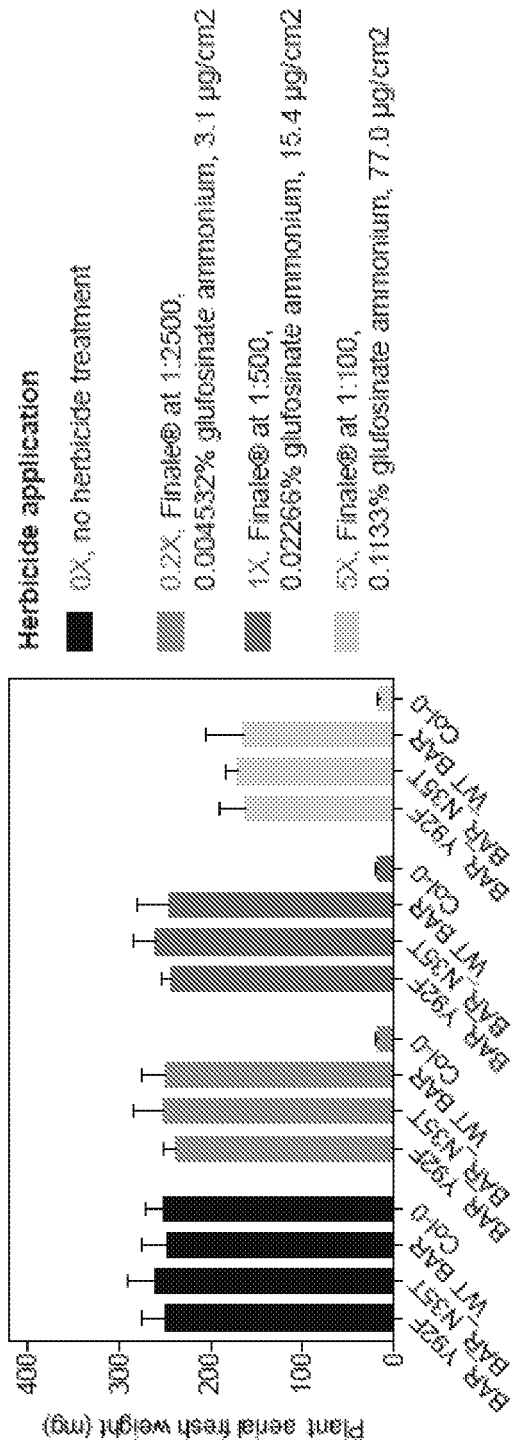

FIGS. 17A-17B. Resistance to phosphinothricin of transgenic *Arabidopsis* transformed with BAR variants Y92F, N35T and WT BAR. FIG. 17A. 17-day old transgenic T2 plants were sprayed with 3 different concentrations of Finale® and further grown for 8 days. Photographs were taken 8 days after Finale® application. Scale bar=1 cm. FIG. 17B. Average fresh weight were measured for each population 8 days after Finale® application. Error bars, mean of plant aerial fresh weight ±s.d. (n=6 (Y92F), 5 (N35T), 5 (WT BAR), 2 (Col-0) biological replicates from individual populations). The weight of 7-9 plants were measured and averaged for each individual population.

DETAILED DESCRIPTION OF THE INVENTION

A description of example embodiments of the invention follows.

Glufosinate, also known as phosphinothricin, is a naturally occurring herbicide derived from the tripeptide antibiotic bialaphos isolated from species of *Streptomyces* soil bacteria. Glufosinate is a structural analog of glutamate, and thereby inhibits glutamine synthetase, an essential enzyme necessary for glutamine synthesis and ammonia detoxification in plants, giving rise to its herbicidal activity, C. J. Thompson et al., *EMBO J.* 6, 2519-2523 (1987). In the 1980s, the bialaphos resistance (BAR) gene and its closely related homolog phosphinothricin acetyltransferase (PAT) gene were isolated from *S. hygroscopicus* and *S. viridochromogenes*, respectively, and were later broadly used as transgenes to confer herbicide resistance in a variety of major genetically modified (GM) crops, including corn, soybean, canola, and cotton. Currently, glufosinate-resistance is the second most widespread herbicide-resistance trait after glyphosate resistance (Duke, S. O. *Pest Management Science* 61, 211-218 (2005)). In addition, BAR and PAT have also gained much utility in basic research as selection markers for generating transgenic plants (Wehrmann, A. et al., *Nature Biotech.* 14, 1274-1278 (1996)). Mechanistically, BAR and PAT encode phosphinothricin acetyltransferase, which transfers an acetyl group from acetyl coenzyme A (acetyl-CoA) to the α-NH2 group of phosphinothricin, resulting in herbicide inactivation.

BAR interferes with plant metabolism by converting two endogenous amino acids, aminoadipate and tryptophan, to their respective N-acetylated products in various species of BAR-containing transgenic plants. Presented herein are structural and mechanistic bases for the native and promiscuous reactions catalyzed by BAR. Through structure-guided protein engineering, several BAR variants that display significantly reduced promiscuous activities while maintaining their glufosinate deactivating activity in plants were generated. These variants can be applicable in developing herbicide resistance technology in plants.

Bialaphos Resistance Acetyltransferase Variant Compositions

Accordingly, in one aspect, the present invention relates to a nucleic acid encoding a bialaphos resistance (BAR) protein variant, wherein the BAR protein variant possesses a modified acetyltransferase activity against tryptophan or aminoadipate, or both, as compared to a wildtype BAR protein (e.g., comprising the sequence set forth in SEQ ID NO: 1).

In another aspect, the present invention relates to a nucleic acid encoding a phosphinothricin acetyltransferase (PAT) variant, wherein the PAT variant possesses a modified acetyltransferase activity against tryptophan or aminoadipate, or both, as compared to a wildtype PAT protein (e.g., comprising the sequence set forth in SEQ ID NO: 2).

In certain embodiments, the nucleic acid encoding a bialaphos resistance acetyltransferase (e.g., BAR or PAT) further comprises a promoter sequence operably linked to the sequence that encodes a bialaphos resistance acetyltransferase (e.g., BAR or PAT) variant. Promoters capable of directing transcription in a plant are available and known to one of ordinary skill in the art. Examples of such promoters include cauliflower mosaic virus promoter, mannopine synthase promoter, and figwort mosaic caulimovirus promoter.

As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As used herein, "wildtype" in the context of the BAR protein refers to the canonical amino acid sequence as found in nature (e.g., as occurs in the bacterium *S. hygroscopicus*). A particular example of a wildtype *S. hygroscopicus* BAR sequence is SEQ ID NO:1. Similarly, "wildtype" in the context of the PAT protein refers to the canonical amino acid sequence as found in nature (e.g., as occurs in the bacterium *S. viridochromogenes*). A particular example of a wildtype *S. viridochromogenes* PAT sequence is SEQ ID NO:2. Table 1 provides the sequences of BAR and PAT proteins from *S.*

*hygroscopicus* and *S. viridochromogenes*, respectively. A nucleic acid sequence that encodes SEQ ID NO: 1 or SEQ ID NO: 2 can be readily determined by those of skill in the art. An example of a known nucleic acid sequence that encodes SEQ ID NO: 1 can be found at GenBank accession no. X17220.1. As those of skill in the art would appreciate, a nucleic acid sequence can be modified, e.g., for codon optimization in a plant.

TABLE 1

BAR and PAT amino acid sequences

Wildtype BAR  MSPERRPADIRRATEADMPAVCTIVNHYIETSTVNFRTEPQEPQEWTDD
              LVRLRERYPWLVAEVDGEVAGIAYAGPWKARNAYDWTAESTVYVSP
              RHQRTGLGSTLYTHLLKSLEAQGFKSVVAVIGLPNDPSVRMHEALGYA
              PRGMLRAAGFKHGNWHDVGFWQLDFSLPVPPRPVLPVTEI
              (SEQ ID NO: 1)

Wildtype PAT  MSPERRPVEIRPATAADMAAVCDIVNHYIETSTVNFRTEPQTPQEWIDD
              LERLQDRYPWLVAEVEGVVAGIAYAGPWKARNAYDWTVESTVYVSH
              RHQRLGLGSTLYTHLLKSMEAQGFKSVVAVIGLPNDPSVRLHEALGYT
              ARGTLRAAGYKHGGWHDVGFWQRDFELPAPPRPVRPVTQI
              (SEQ ID NO: 2)

As used herein, a "variant" in the context of a BAR protein refers to an engineered BAR protein having an amino acid sequence that differs from a wildtype BAR amino acid sequence. Similarly, a "variant" in the context of a PAT protein refers to an engineered PAT protein having an amino acid sequence that differs from a wildtype PAT protein amino acid sequence. In certain embodiments, the variant is at least 90%, at least 91%, at least 92%, at least 93%, at least 94%, at least 95%, at least 96%, at least 97%, at least 98%, at least 99%, or more identical to SEQ ID NO: 1 or SEQ ID NO: 2.

As described herein, the BAR protein variants or the PAT protein variants of the present invention possess a modified acetyltransferase activity against tryptophan or aminoadipate, or both, as compared to the respective wildtype enzyme. As used herein, "modified" in the context of acetyltransferase activity refers to activity that is altered (e.g., reduced or increased) relative to the acetyltransferase activity of the respective wildtype enzyme, as measured by standard methods in enzyme kinetics (e.g., measuring Km, Kcat or Kcat/Km values).

In certain embodiments, the BAR protein variant or PAT protein variant possesses a reduced acetyltransferase activity against tryptophan or aminoadipate, or both. In certain embodiments, the variant activity is reduced by at least 10%. For example, in certain embodiments, the variant activity is reduced by between 10% and 25%, between 25% and 50%, between 50% and 75%, between 75% and 90%. In certain embodiments, the variant activity is reduced by about 10%, about 20%, about 30%, about 40%, about 50%, about 60%, about 70%, about 80%, about 90%, or about 100% compared to its wildtype counterpart.

In certain embodiments, the BAR protein variant or PAT protein variant possesses an increased acetyltransferase activity against tryptophan or aminoadipate, or both. In certain embodiments, the variant activity is increased by at least 10%. For example, in certain embodiments, the variant activity is increased by between 10% and 25%, between 25% and 50%, between 50% and 75%, between 75% and 90%, between 90% and 110%, between 110% and 140%, between 140% and 175%, between 175% and 200%, between 225% and 250%, between 250% and 275%, between 275% and 300%, between 300% and 325%, between 325% and 350%, between 350% and 375%, between 375% and 400%, between 425% and 450%, between 450% and 475%, between 475% and 500%. In certain embodiments, the variant activity is increased by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, or about 500% compared to its wildtype counterpart.

Unless otherwise indicated or otherwise evident from the context and understanding of one of ordinary skill in the art, values that are expressed as ranges can assume any specific value or subrange within the stated ranges in various embodiments, unless the context clearly dictates otherwise. "About" in reference to a numerical value generally refers to a range of values that fall within ±8%, in some embodiments ±6%, in some embodiments ±4%, in some embodiments ±2%, in some embodiments ±1%, in some embodiments ±0.5% of the value unless otherwise stated or otherwise evident from the context.

In certain embodiments, the BAR protein variants or PAT protein variants described herein confer phosphinothricin resistance in a plant. In certain embodiments, the phosphinothricin resistance of the BAR protein variant or PAT protein variant is increased as compared to the phosphinothricin resistance conferred by the respective wildtype enzyme. In certain embodiments, the phosphinothricin resistance of the BAR protein variant or PAT protein variant is reduced as compared to the phosphinothricin resistance conferred by the respective wildtype enzyme.

One or more amino acid substitutions in a BAR or PAT protein that confer a modified acetyltransferase activity can be determined according to the methods described herein. In certain embodiments, a BAR protein variant comprises an amino acid substitution at any one or more amino acid residues at position N35, Y73, T90, Y92, V125, F36, K78, R80, or Y83 of SEQ ID NO: 1. In certain embodiments, a PAT protein variant comprises an amino acid substitution at any one or more amino acid residues at position N35, Y73, T90, Y92, V125, F36, K78, R80, or Y83 of SEQ ID NO: 2. In certain embodiments, at least one amino acid substitution is a conservative substitution. In certain embodiments, at least one amino acid substitution is a non-conservative substitution. One of ordinary skill in the art can readily identify which substitutions are conservative or non-conservative, on the basis of, e.g., structure and/or the general chemical characteristics of each amino acid R group. For example, a conservative substitution can be made by substituting one aliphatic amino acid (e.g., G, A, V, L, or I) with another; by substituting one aromatic amino acid (e.g., F, Y, or W) with another; or substituting one basic amino acid (e.g., H, K, or R) with another. Various classifications of amino acids are available and well known to one or ordinary skill in the art. Methods for producing proteins having amino acid substitutions (e.g., site-directed mutagenesis) are well known and routine to one of ordinary skill in the art.

In certain embodiments, the BAR protein variant comprises any one or more of the following amino acid substitutions: N35T, N35S, Y53F, T90A, Y92F, V125T, V125L, V125I, F36A, K78A, R80A, or Y83F of SEQ ID NO: 1. In certain embodiments, the PAT protein variant comprises any one or more of the following amino acid substitutions: N35T, N35S, Y53F, T90A, Y92F, V125T, V125L, V125I, F36A, K78A, R80A, or Y83F of SEQ ID NO: 2.

In certain embodiments, a BAR protein variant having reduced acetyltransferase activity against tryptophan or aminoadipate, or both, comprises any one or more of the following amino acid substitutions: N35T, N35S, Y53F, T90A, Y92F, V125L, V125I, F36A, or R80A of SEQ ID NO: 1. In certain embodiments, a PAT protein variant having reduced acetyltransferase activity against tryptophan or aminoadipate, or both, comprises any one or more of the following amino acid substitutions: N35T, N35S, Y53F, T90A, Y92F, V125L, V125I, F36A, or R80A of SEQ ID NO: 2.

In certain embodiments, a BAR protein variant having increased acetyltransferase activity against tryptophan or aminoadipate, or both, comprises any one or more of the following amino acid substitutions: K78A, Y83F, or V125T of SEQ ID NO: 1. In certain embodiments, a PAT protein variant having increased acetyltransferase activity against tryptophan or aminoadipate, or both, comprises any one or more of the following amino acid substitutions: K78A, Y83F, or V125T of SEQ ID NO: 2.

Figure 13A:
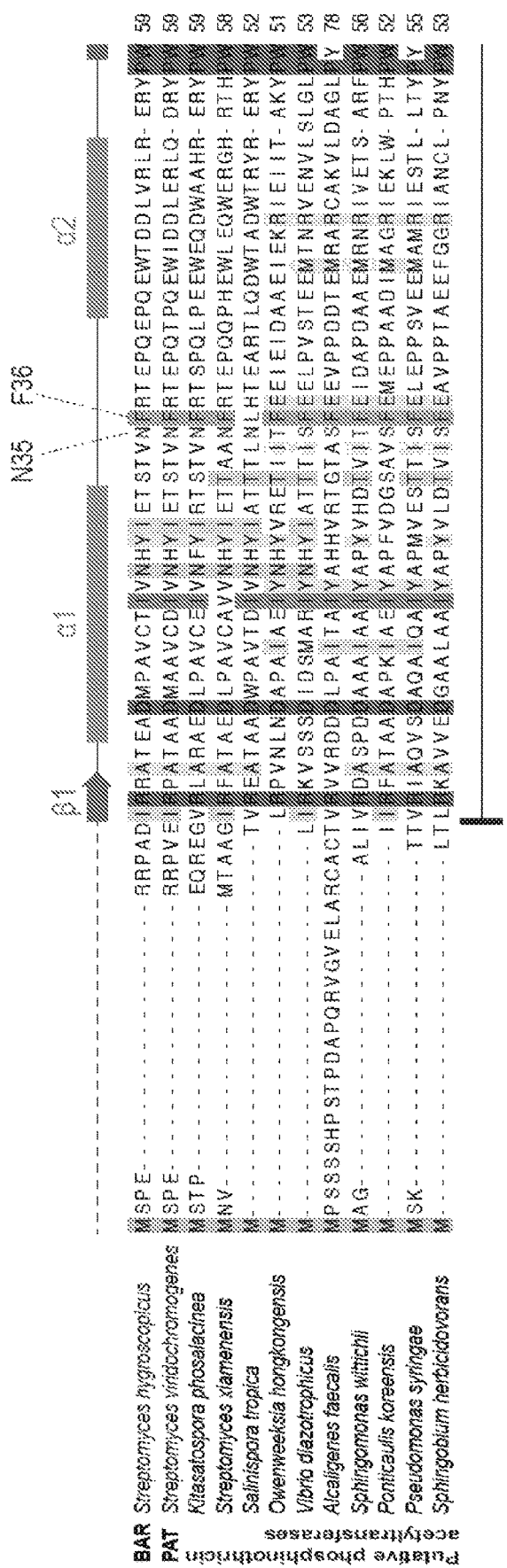
FIGS. 13A-13C. Protein sequence alignment of BAR from *Streptomyces hygroscopicus* (SEQ ID NO: 88), PAT from *Streptomyces viridochromogenes* (SEQ ID NO: 89) and closely related homologues from other species (SEQ ID NOs: 90-99). Active site residues as displayed in FIG. 4B are labeled. The alignment was performed using Jalview V2 (T-Coffee, default settings; Waterhouse, A. M., et al. *Bioinformatics* 25, 1189-1191 (2009)). Secondary structure of BAR as labeled in FIG. 4A is shown. The acetyltransferase GNAT domain (pfam13420) is displayed. Protein sequences related to BAR from *Streptomyces hygroscopicus* were retrieved from GenBank at the NCBI website using protein BLAST search. Protein sequence accessions (GenBank): *Streptomyces hygroscopicus*: CAA29262 (SEQ ID NO: 88); *Streptomyces viridochromogenes* (SEQ ID NO: 89), WP 003988626; *Kitasatospora phosalacinea*, WP 033213694
Figure 13B:
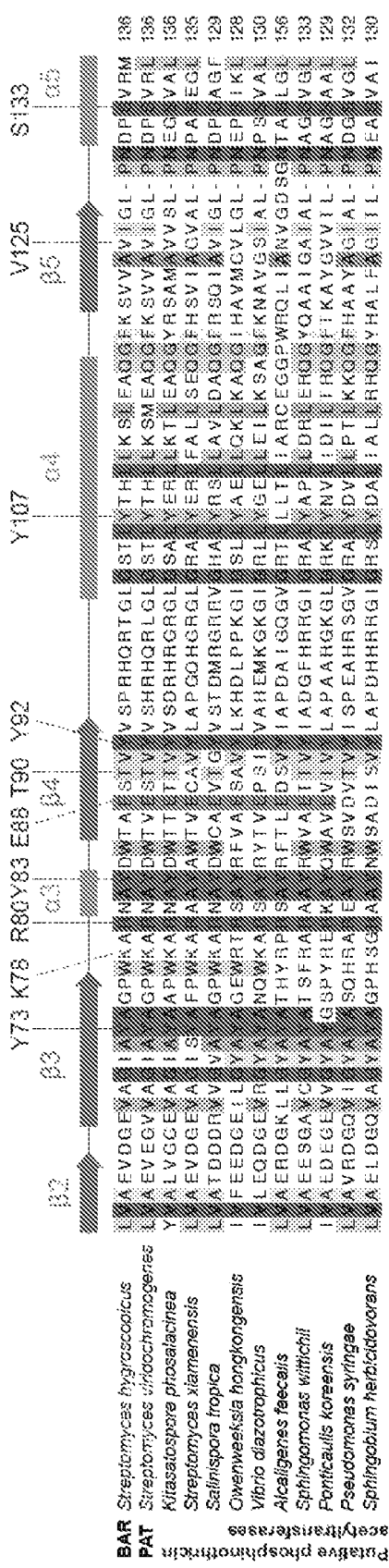
Figure 13C:
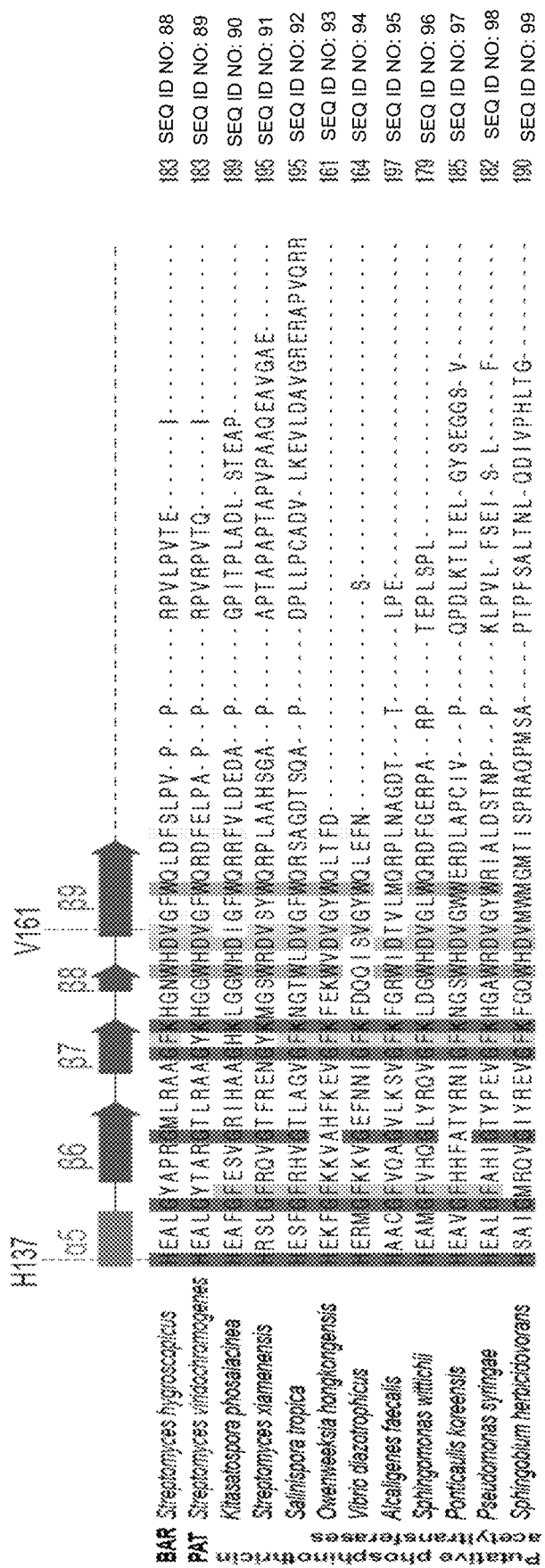

In certain embodiments, the BAR or PAT variant may differ at one or more positions in addition to one or more of the specific positions described herein from a corresponding wildtype BAR or PAT (e.g., N35, Y73, T90, Y92, V125, F36, K78, R80, or Y83 of SEQ ID NO: 1 or SEQ ID NO: 2). For example, as those of skill in the art would appreciate, one or more amino acids between BAR and PAT that are not identical, but occur at equivalent positions, can be substituted for the other and maintain an equivalent function. As another example, one or more amino acids that are not identical between BAR proteins from different species (e.g., homologs or orthologs of BAR), but occur at equivalent positions can be substituted for the other and maintain an equivalent function. Similarly, one or more amino acids that are not identical between PAT proteins from different species (e.g., homologs or orthologs of PAT), but occur at equivalent positions can be substituted for the other and maintain an equivalent function. In certain embodiments, any one or more of the mutations described herein may be incorporated into a wild type homolog or ortholog of SEQ ID NO: 1 or SEQ ID NO: 2 to produce a variant of said wild type homolog or ortholog. In some embodiments the variant is at least 90%, at least 91%, at least 92%, at least 93%, at least 94%, at least 95%, at least 96%, at least 97%, at least 98%, at least 99%, or more identical to a wild type homolog or ortholog of SEQ ID NO: 1 or SEQ ID NO: 2. Examples of species that encode homologs or orthologs, along with sequences of such homologs are provided in FIGS. 13A-13C. One of ordinary skill in the art could readily identify additional homologs or orthologs from other species.

In other aspects, the present invention relates to a vector comprising the nucleic acid of any of the preceding embodiments. In certain embodiments, the vector is a plasmid, and includes any one or more plasmid sequences such as, e.g., a promoter sequence, a selection marker sequence, or a locus-targeting sequence for integration into the genome of a plant. In certain embodiments, a BAR protein variant itself can be used as a selectable marker. In certain embodiments, a PAT protein variant itself can be used as a selectable marker.

In other aspects, the present invention relates to a host cell comprising a vector as described herein. In certain embodiments, the host cell is an *Agrobacterium*. In certain embodiments, the host cell is a plant cell that belongs to any of the known species of plants. In certain embodiments, the plant cell belongs to a genus selected from the group consisting of *Arabidopsis, Beta, Glycine, Helianthus, Solanum, Triticum, Oryza, Brassica, Medicago, Prunus, Malta, Hordeum, Musa, Phaseolus, Citrus, Piper, Sorghum, Daucus, Manihot, Capsicum*, and *Zea*.

Methods of Using Bialaphos Resistance Acetyltransferase Variants

The present invention also provides methods of generating a transgenic plant that comprises any of the foregoing bialaphos resistance acetyltransferase (e.g., BAR or PAT) variants described herein. Any of the bialaphos resistance acetyltransferase (e.g., BAR or PAT) variants described herein can be used in the methods described herein.

In one aspect, the present invention relates to a method of generating a transgenic plant that comprises a BAR protein variant, as described herein. The method comprises introducing into a plant a nucleic acid encoding a BAR protein variant, wherein the BAR protein variant possesses a modified acetyltransferase activity against tryptophan or aminoadipate, or both, as compared to a wildtype BAR protein (e.g., comprising the sequence set forth in SEQ ID NO: 1). In one embodiment, the method further comprises integrating the nucleic acid into the genome of the plant, thereby generating a transgenic plant. However, as those skilled in the art would recognize, transient transformation techniques (e.g., protoplast transformation) can be used that do not require integration into the plant genome. In certain embodiments, the method further comprises expressing the BAR protein variant in the plant tissue, cell, or seed.

In another aspect, provided herein is method of generating a transgenic plant that comprises a PAT protein variant, as described herein. The method comprises introducing into a plant a nucleic acid encoding a PAT protein variant, wherein the PAT protein variant possesses a modified acetyltransferase activity against tryptophan or aminoadipate, or both, as compared to a wildtype PAT protein (e.g., comprising the sequence set forth in SEQ ID NO: 2). In one embodiment, the method further comprises integrating the nucleic acid into the genome of the plant, thereby generating a transgenic plant. However, as those skilled in the art would recognize, transient transformation techniques (e.g., protoplast transformation) can be used that do not require integration into the plant genome. In certain embodiments, the method further comprises expressing the PAT protein variant in the plant tissue, cell, or seed.

In certain embodiments, the nucleic acid is introduced into a tissue, cell, or seed of the plant. Various methods of introducing nucleic acid into the tissue, cell, or seed of plants are known to one of ordinary skill in the art. The particular method can be selected based on several considerations, such as, e.g., the type of plant used. For example, the floral dip method, as described herein, is a suitable method for introducing genetic material into *Arabidopsis*. In certain embodiments, the nucleic acid can be delivered into the plant by an *Agrobacterium*.

In certain embodiments, the plant belongs to a genus selected from the group consisting of *Arabidopsis, Beta, Glycine, Helianthus, Solanum, Triticum, Oryza, Brassica, Medicago, Prunus, Malta, Hordeum, Musa, Phaseolus, Citrus, Piper, Sorghum, Daucus, Manihot, Capsicum,* and *Zea.*

The present invention also provides a transgenic plant that comprises any of the foregoing bialaphos resistance acetyltransferase (e.g., BAR or PAT) variants described herein.

In one aspect, provided herein is a transgenic plant comprising a nucleic acid encoding a BAR protein variant, wherein the BAR protein variant possesses a modified acetyltransferase activity against tryptophan or aminoadipate, or both, as compared to a wildtype BAR protein (e.g., comprising the sequence set forth in SEQ ID NO: 1).

In another aspect, provided herein is a transgenic plant comprising a nucleic acid encoding a PAT protein variant, wherein the PAT protein variant possesses a modified acetyltransferase activity against tryptophan or aminoadipate, or both, as compared to a wildtype PAT (e.g., comprising the sequence set forth in SEQ ID NO: 2).

As those of skill in the art would appreciate, the present invention also provides a product produced by, or derived from, a transgenic plant described herein. For example, the present invention provides a fruit, oil, fiber, wood, or any portion (e.g., flowers, leaves, roots, or vegetable) derived from a transgenic plant described herein.

A transgenic plant according to the present invention can be generated from any of the known species of plants. In certain embodiments, the plant belongs to a genus selected from the group consisting of *Arabidopsis, Beta, Glycine, Helianthus, Solanum, Triticum, Oryza, Brassica, Medicago, Prunus, Malus, Hordeum, Musa, Phaseolus, Citrus, Piper, Sorghum, Daucus, Manihot, Capsicum,* and *Zea.*

In certain aspects, the present invention also provides a method of cultivating a transgenic plant described herein, comprising exposing the plant to a herbicide (e.g., phosphinothricin) during at least part of the cultivation period, and harvesting the plant or a product of the plant (e.g., a fruit, oil, fiber, wood, or any portion of the plant).

In another aspect, the present invention provides a product produced by, or derived from, a transgenic plant described herein. The product includes, e.g., a fruit, oil, fiber, wood, or any portion (e.g., leaves, roots, or vegetable) derived from a transgenic plant described herein.

Methods of Identifying Interference with Plant Endogenous Amino Acid Metabolism

The present invention also provides a method of detecting acetyl-aminoadipate and/or acetyl-tryptophan levels in a plant or a product produced by, or derived from, a plant. Such a method can have various applications, including, determining e.g., whether a plant is a transgenic plant (e.g., whether it is a BAR- or PAT-modified plant); whether a BAR- or PAT-modified plant produces a byproduct of bialaphos resistance acetyltransferase activity, such as acetyl-aminoadipate and/or acetyl-tryptophan; and/or whether a product is produced by or derived from a BAR- or PAT-modified plant.

Thus, provided herein is method of detecting acetyl-aminoadipate or acetyl-tryptophan, or both, in a plant, comprising extracting metabolites from the plant and measuring the level of the metabolite acetyl-aminoadipate or acetyl-tryptophan, or both, in the plant extract. Methods of extracting metabolites from a plant, as well as measuring the level of acetyl-aminoadipate and acetyl-tryptophan, are described herein, and are well known to one or ordinary skill in the art. For example, as described herein, metabolites can be extracted from various parts of a plant, e.g., leaves, flowers, roots, stems, fruits, ovary, pollen, or seeds of plants. Levels of acetyl-aminoadipate or acetyl-tryptophan can be measured according to various methods known in the art, including, e.g., chromatographic, colorimetric, and fluorometric methods.

In certain embodiments, the method further comprises comparing the level measured to a reference level of acetyl-aminoadipate or acetyl-tryptophan. In certain embodiments, the reference level is the level of acetyl-aminoadipate or acetyl-tryptophan measured from a control plant, e.g., a plant that does not express a BAR protein or a BAR protein variant; or a PAT protein or a PAT protein variant. In certain embodiments, the reference level is a level of acetyl-aminoadipate or acetyl-tryptophan that is accepted as a baseline level for the particular plant species.

In certain embodiments, an increase in the measured level of acetyl-aminoadipate or acetyl-tryptophan as compared to a control level of acetyl-aminoadipate or acetyl-tryptophan, respectively, identifies a plant as having an interference in its endogenous amino acid metabolism that results from BAR or PAT expression. In certain embodiments, the measured level of acetyl-aminoadipate or acetyl-tryptophan is increased by at least 10%. For example, in certain embodiments, the measured level of acetyl-aminoadipate or acetyl-tryptophan is increased by between 10% and 25%, between 25% and 50%, between 50% and 75%, between 75% and 90%, between 90% and 110%, between 110% and 140%, between 140% and 175%, between 175% and 200%, between 225% and 250%, between 250% and 275%, between 275% and 300%, between 300% and 325%, between 325% and 350%, between 350% and 375%, between 375% and 400%, between 425% and 450%, between 450% and 475%, between 475% and 500%, between 500% and 550%, between 550% and 600%, between 650% and 700%, between 700% and 800%, between 800% and 900%, between 900% and 1000%, between 1000% and 1250%, between 1250% and 1500%, between 1500% and 2000%, between 2000% and 3000%, between 3000% and 4000%, between 4000% and 5000%, between 5000% and 6000%, between 6000% and 7000%, between 7000% and 8000%, between 8000% and 9000%, between 9000% and 10000%. In certain embodiments, the measured level of acetyl-aminoadipate or acetyl-tryptophan is increased by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, about 500%, about 600%, about 700%, about 800%, about 900%, about 1000%, about 1100%, about 1200%, about 1300%, about 1400%, about 1500%, about 1600%, about 1700%, about 1800%, about 1900%, about 2000%, about 2500%, about 3000%, about 3500%, about 4000%, about 4500%, about 5000%, about 5500%, about 6000%, about 6500%, about 7000%, about 7500%, about 8000%, about 8500%, about 9000%, about 9500%, or about 10000% as compared to a reference level of acetyl-aminoadipate or acetyl-tryptophan, respectively.

In certain embodiments, the plant from which the level of acetyl-aminoadipate or acetyl-tryptophan is measured expresses a bialaphos resistance acetyltransferase, e.g., a wildtype BAR protein (e.g., comprising the sequence set forth in SEQ ID NO: 1), a wildtype PAT protein (e.g., comprising the sequence set forth in SEQ ID NO: 2), or a BAR protein variant or PAT protein variant, as described herein.

EXEMPLIFICATION

Materials and Methods

Plant Materials

*Arabidopsis* (*Arabidopsis thaliana*) Columbia-0 (Col-0) and Wassilewskija (Ws) were used as wild-types. T-DNA insertion lines were from the following collections: SALK lines (Alonso, J. M. et al., *Science* 301, 653-657 (2003)): SALK_130606 (SALK_1), SALK_051823C (SALK_2), SALK_110649 (SALK_3); SAIL lines *The Plant Cell* 14, 2985-2994 (2002)): SAIL_1165_B02 (SAIL_1), SAIL_503_C03 (SAIL_2), SAIL_1235_D10 (SAIL_3); GABI lines (Rosso, M. G. et al., *Plant Molecular Biology* 53, 247-259 (2003)): GABI_453E01 (GABI_1), GABI_833F02 (GABI_2), GABI_453A08 (GABI_3); FLAG lines (Samson, F. et al., *Nucleic Acids Res.* 30, 94-97 (2002)): FLAG_076H05 (clh2-1 (Schenk, N. et al., *FEBS letters* 581, 5517-5525 (2007)); FLAG_1), FLAG_271B02 (FLAG_2), FLAG_495A09 (FLAG_3), FLAG_271B12 (FLAG_lkrsdh). SALK, SAIL and GABI lines were obtained from the European *Arabidopsis* Stock Center. The FLAG lines were obtained from the INRA Versailles *Arabidopsis* Stock Center. Homozygous (and heterozygous for FLAG_lkrsdh) plants were identified by PCR using T-DNA- and gene-specific primers.

*Arabidopsis* T-DNA lines were grown on soil under a 12-h-light/12-h-dark photoperiod with fluorescent light of 80 to 120 µmol photons $m^{-2}$ $s^{-1}$ at 22° C. and 60% relative humidity. For senescence induction, leaves from 5-week-old plants were excised and incubated in permanent darkness on wet filter paper for 8 d at ambient temperature. Transgenic *Arabidopsis* lines transformed with BAR mutants were grown on soil under a 16-h-light/8-h-dark photoperiod with fluorescent light of 80 to 120 µmol photons $m^{-2}$ $s^{-1}$ at 22° C. and 60% relative humidity. For senescence induction, leaves from phosphinothricin-resistant, 4-week-old plants were excised and incubated in permanent darkness on wet filter paper for 6 d at ambient temperature.

Wild-type and phosphinothricin-resistant *Brassica juncea* (Song, W. Y. et al., *PNAS USA* 108, 19808-19813 (2011)) were grown on soil under a 16-h-light/8-h-dark photoperiod with fluorescent light of 80 to 120 µmol photons $m^{-1}$ $s^{-1}$ at 22° C. and 60% relative humidity. For senescence induction, fully developed cotyledons were excised and incubated in permanent darkness on wet filter paper for 5-7 d at ambient temperature.

Figure 7A:
FIGS. 7A-7C. Accumulation of acetyl-aminoadipate and acetyl-tryptophan in *Glycine max* and *Brassica juncea* carrying the BAR transgene.

Phosphinothricin-resistant *Glycine max* (Liberty Link trait A2704-12, 283 Morril MC-116, Credenz CZ 3841 LL, Bayer CropScience). Wild-type *Glycine max* (variety: Chiba Green) was obtained from local market (High Mowing Organic Seed). *Glycine max* was grown on soil under a 16-h-light/8-h-dark photoperiod with fluorescent light of 80 to 120 µmol photons $m^{-1}s^{-1}$ at 22° C. and 60% relative humidity. For testing phosphinothricin resistance, 30-days old plants were sprayed with Finale® (Bayer CropScience) diluted 1:500 in water and photographs were taken after 14 days (FIG. 7A). Green and senescent leaf samples were collected from 40-days old plants.

Metabolite Extraction

*Arabidopsis* samples were collected in 2 mL Eppendorf tubes containing 500 µL of 1.5 mm glass beads, weighted and snap-frozen in liquid nitrogen. The frozen samples were ground using a MM300 Mixer Mill (Retsch) at 30 Hz for 5 min and stored at −80° C. until further processing. *Brassica juncea* and *Glycine max* samples were snap-frozen in liquid nitrogen and ground with a mortar and pestle. Metabolites were extracted using 5 (leaf samples) or 10 volumes (seed samples; w/v) of ice-cold extraction buffer (80% methanol, 20% water, 0.1% formic acid (v/v/v) and 1 µg $mL^{-1}$ ampicillin as internal standard). Extracts were homogenized at 30 Hz for 5 min and centrifuged (14,000-16,000 g, 4° C.). After re-centrifugation, supernatants were transferred to LC vials and analyzed by LC-MS.

LC-MS Analysis of *Arabidopsis* T-DNA Mutants and *Brassica juncea*

The LC-MS instrument was composed of an Ultimate 3000 Rapid Separation LC system (Thermo Scientific) coupled to a Bruker Compact ESI-Q-TOF (Bruker Daltonics). The reverse-phase chromatography system consisted of an 150 mm C18 column (ACQUITY UPLC™ BEH, 1.7 µm, 2.1×150 mm, Waters), which was developed using LC-MS solvents (Chemie Brunschwig) with a gradient (flow rate of 0.3 mL $min^{-1}$) of solvent B (acetonitrile with 0.1% (v/v) formic acid) in solvent A (water with 0.1% (v/v) formic acid) as follows (all (v/v)): 5% for 0.5 min, 5% to 100% in 11.5 min, 100% for 4 min, 100% to 5% in 1 min and 5% for 1 min. Electrospray ionization (ESI) source conditions were set as follows: gas temperature, 220° C.; drying gas, 9 L $min^{-1}$; nebulizer, 2.2 BAR; capillary voltage, 4500 V; end plate offset, 500 V. Tuning conditions were set as follows: funnel 1 RF, 250 Vpp; funnel 2 RF, 150 Vpp; isCID energy, 0 eV; hexapole RF, 50 Vpp; quadrupole ion energy, 3.0 eV; quadrupole low mass, 90 m/z; collision cell, 6 eV; pre-pulse storage time, 3 µs. The instrument was set to acquire over the m/z range 50-1300, with an acquisition rate of 4 spectra $s^{-1}$. Conditions for MS2 of automatically selected precursors (data-dependent MS2) were set as follows: threshold, 1000 counts; active smart exclusion (5×); active exclusion (exclude after 3 spectra, release after 0.2 min, reconsider precursor if current intensity/previous intensity is >5); number of precursors, 3; active stepping (basic mode, timing 50%-50%, collision RF from 350 to 450 Vpp, transfer time from 65 to 80 µs, collision energy from 80 to 120%). All data were recalibrated internally using pre-run injection of sodium formate (10 mM sodium hydroxide in 0.2% formic acid, 49.8% water, 50% isopropanol (v/v/v)). After data recalibration using DataAnalysis (version 4.2, Bruker Daltonics) and data conversion to mzXML format using ProteoWizard MSConvert (Chambers, M. C. et al. *Nature Biotech.* 30, 918-920 (2012)), metabolite features detected in Ws and FLAG_076H05 (senescent leaves, four replicates) were aligned according to retention time and relatively quantified using XCMS online (Gowda, H. et al., *Anal. Chem.* 86, 6931-39 (2014)) (pairwise comparison using XCMS online pre-set parameters "UPLC/Bruker Q-TOF"). Upregulated features in FLAG_076H05 were identified at retention times of 2.8 min (labeled as "1" in FIG. 1A, m/z 204.086 (fold change ≥10, p-value ≤0.005, intensity threshold 800,000)) and 6.5 min (labeled as "2" in FIG. 1A, m/z 247.108 (fold change ≥10, p-value ≤0.005, intensity threshold 100,000)) and further characterized as ions derived from N-acetyl-L-aminoadipate and N-acetyl-L-tryptophan, respectively, by database searches in METLIN (Smith C. A. et al., *Therap. Drug Monitoring* 27, 747-51 (2005) using MS and MS2 spectra.

Figure 1A:
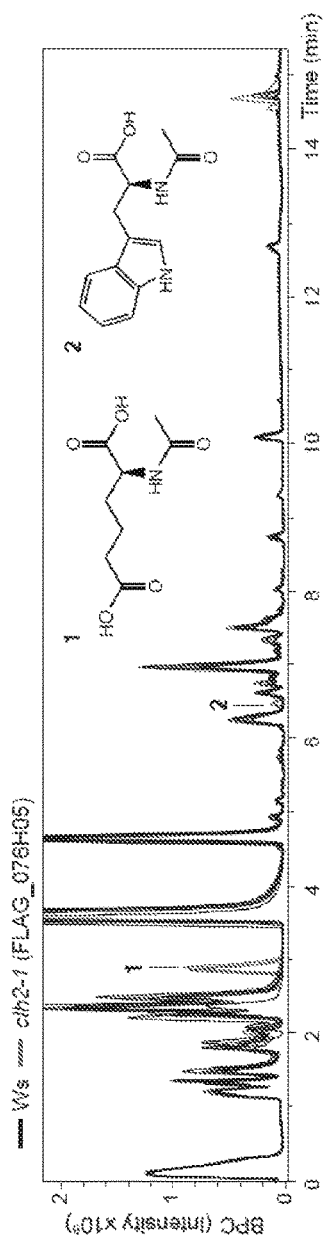
FIGS. 1A and 1B. Accumulation of acetyl-aminoadipate and acetyl-tryptophan in senescent leaves of *Arabidopsis* carrying the BAR transgene.
Figure 1B:
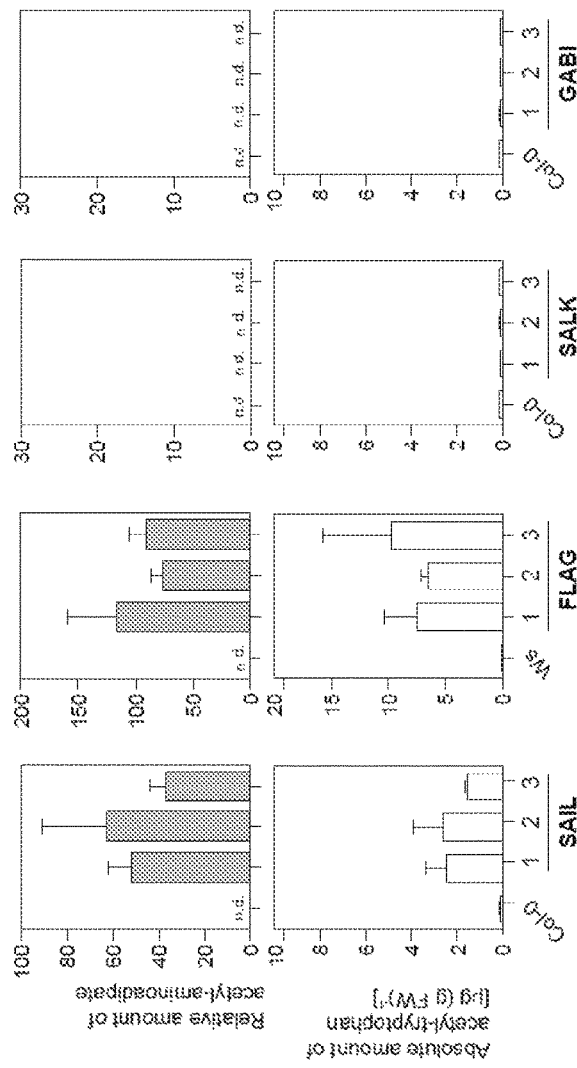

Quantification of acetyl-aminoadipate and acetyl-tryptophan in *Arabidopsis* mutants from different insertion mutant collections was carried out by QuantAnalysis (version 2.2, Bruker Daltonics) using extracted ion chromatogram (EIC) traces ([M+H]$^+$). Because a standard was not commercially available for acetyl-aminoadipate, relative quantification is shown in FIG. 1B. Absolute quantification of acetyl-tryptophan was based on a standard curve established with pure acetyl-tryptophan (Sigma-Aldrich) between 100 pg and 20 µg.

LC-MS Analysis of Phosphinothricin-Resistant *Glycine max*

The LC-MS instrument was composed of an Ultimate 3000 Rapid Separation LC system (Thermo Scientific) coupled to a Q-Exactive mass spectrometer (Thermo Scientific). The reverse-phase chromatography system consisted of an 150 mm C18 Column (Kinetex 2.6 µm silica core shell C18 100 Å pore, Phenomenex), which was developed using Optima™ LC/MS solvents (Fisher Chemical) with a gradient (flow rate of 0.8 mL min$^{-1}$) of solvent B (acetonitrile with 0.1% (v/v) formic acid) in solvent A (water with 0.1% (v/v) formic acid) as follows (all (v/v)): 2% for 2 min, 2% to 99% in 25 min, 99% for 5 min, 99% to 2% in 1 min and 2% for 2 min.

The mass spectrometer was configured as to perform 1 MS scan from m/z 100-800 followed by 1-4 data-dependent MS2 scans using HCD fragmentation with collision energy of 30 eV. The ion source parameters were as follows: spray voltage (+) at 3000 V, capillary temperature at 275° C., sheath gas at 40 arb units, aux gas at 15 arb units, sweep gas at 1 arb unit, max spray current at 100 (µA), probe heater temp at 350° C., ion source: HESI-II. The raw data in Thermo format was converted to mzML format using ProteoWizard MSConvert (Chambers, M. C. et al., *Nature Biotechnology* 30, 918-920 (2012)). Data analysis was performed with Xcalibur (Thermo Scientific) and MZmine2 (Pluska, T. et al., *BMC Bioinform.* 11, 395 (2010)).

Heterologous Expression of Wild-Type BAR and Activity Determination

The BAR coding sequence was amplified by PCR (KaPa HiFi HotStart polymerase; KaPa Biosystems) from genomic DNA extracted from homozygous plants of the SAIL line SAIL_1165_B02 using primers SAIL_BAR_F_pPROEX and SAIL_BAR_R_pPROEX (see Table 3) and then cloned into pProEX Hta (Invitrogen) via EcoRI and HindIII resulting in a 6×His-BAR fusion construct. 6×His-BAR was expressed in *E. coli* BL21(DE3) grown in Luria-Bertani medium. At an optical density at 600 nm of 0.6, protein expression was induced with 1.0 mM isopropylthio-β-galactoside (IPTG), and cells were grown at 37° C. for 2.5 h. Cells from a 200 mL culture were harvested by centrifugation and resuspended in 8 mL binding buffer (20 mM HEPES-KOH pH 7.4, 0.5 M NaCl, 10% (v/v) glycerol, 20 mM imidazole) supplemented with 3 U mL$^{-1}$ DNase (Promega), 2 mM MgCl2 and ⅒ of a tablet containing a protease inhibitor cocktail (Complete; Roche Applied Science). Cell lysis was performed by use of a high-pressure cell breaker (Cell Disruption System; Constant Systems) at a pressure of 150 MPa. All the following steps were carried out at 4° C. The lysate was centrifuged (16,000 g, 20 min) and a 50% (v/v) slurry of Ni$^{2+}$-ion charged agarose beads (Ni Sepharose 6 Fast Flow; GE Healthcare) in binding buffer was added to the supernatant (0.25 mL 50% slurry per mL of supernatant). The mix was incubated for 1 h with slight shaking and then loaded on a Poly-Prep® chromatography column (0.8×4 cm; Bio-Rad). The beads were washed with 10 mL of binding buffer and 3 mL of wash buffer (20 mM HEPES-KOH pH 7.4, 0.5 M NaCl, 10% (v/v) glycerol, 40 mM imidazole) by gravity flow before elution with 3 mL of elution buffer (20 mM HEPES-KOH pH 7.4, 0.5 M NaCl, 10% (v/v) glycerol, 500 mM imidazole). The buffer was exchanged with storage buffer (20 mM HEPES-KOH pH 7.4, 0.5 M NaCl, 10% (v/v) glycerol, 1 mM dithiothreitol) using an ultra-centrifugal filter (MWCO 10,000; Vivaspin 6, Sartorius Stedim Biotech). The purity of the protein preparation was assessed by SDS-PAGE and the concentration was determined by using a NanoDrop 2000 UV-VIS spectrometer (Thermo Scientific).

Enzyme assays were carried out in 10 mM HEPES-KOH (pH 7.4), 20 mM MgCl2, and 2 mM acetyl-CoA (Sigma-Aldrich; final volume 25 µl). Before determining the kinetics of BAR with different substrates, time-dependent activity of the purified protein was tested at substrate concentrations of 200 µM L-phosphinothricin (glufosinate ammonium, considered as a 1:1 mixture of L- and D-enantiomers; Sigma-Aldrich) or 400 µM (L-aminoadipate and L-tryptophan; Sigma-Aldrich). Reactions were initiated by the addition of purified BAR at 0.03 µM (assays with L-phosphinothricin) or 20 µM (assays with aminoadipate or tryptophan) and incubated at 25° C. for the indicated times (FIGS. 8A-8D). Reactions were stopped by the addition of three volumes of methanol supplemented with 0.5% (v/v) formic acid. Likewise, substrate concentration-dependence was determined by incubating assays for 7.5 min (assays with L-phosphinothricin) or 2 h (assays with aminoadipate or tryptophan; FIG. 3). Control assays (FIG. 3B) were performed with aminoadipate and tryptophan at 8.4 mM, but in the absence of BAR. In addition, D-tryptophan (Sigma-Aldrich) was tested as potential substrate at 8.4 mM (FIG. 3B).

In vitro assays with aminoadipate and tryptophan as substrate were analyzed by LC-MS as described above. In vitro assays with L-phosphinothricin were analyzed by LC-MS as described above, but using a normal-phase chromatography system as follows: an 150 mm amide column (ACQUITY UPLC™ BEH amide, 1.7 µm, 2.1×150 mm, Waters) was developed using LC-MS solvents (Chemie Brunschwig) with a gradient (flow rate of 0.4 mL min$^{-1}$) of solvent B (acetonitrile with 0.1% (v/v) formic acid) in solvent A (water with 0.1% (v/v) formic acid) as follows (all (v/v)): 95% for 0.5 min, 95% to 30% in 12 min, 30% for 2 min, 30% to 95% in 1 min and 95% for 5 min. Data were analyzed using DataAnalysis and QuantAnalysis (versions 2.2, Bruker Daltonics). Relative values for acetyl-aminoadipate and acetyl-tryptophan were normalized by correcting for the different ionization efficiencies of their substrates aminoadipate and tryptophan. The KM value for phosphinothricin was inferred using the Michaelis-Menten kinetics nonlinear regression function under Prism 5 (GraphPad).

X-Ray Crystallography

6×His-tagged BAR protein was expressed from pProEx Hta (see above) in *E. coli* BL21(DE3) grown in Terrific Broth medium. At an optical density at 600 nm of 0.6, protein expression was induced with 1.0 mM IPTG and cells were grown at 37° C. for 2.5 h. Cells from 1 L culture were harvested by centrifugation and resuspended in 25 mL binding buffer (50 mM Tris-HCl pH 8, 500 mM NaCl, 30 mM imidazole). All the following steps were carried out at 4° C. Cell lysis was performed using a microfluidizer (HC-8000, Microfluidics). The lysate was centrifuged (16,000 g) for 20 min, and the 6×His-tagged BAR protein was purified by metal affinity (5-ml HisTrap HP column, GE Healthcare) and size-exclusion chromatography (HiLoad 16/600 Superdex 200 pg, GE Healthcare) using an AKTA Pure FPLC system (GE Healthcare). The 6×His-TEV tag was removed from BAR prior to size-exclusion chromatography by overnight incubation with 1 µg of 6×His-TEV protease (Tropea, J. E. et al., *Methods in Mol. Bio.* 498, 297-307 (2009)) per 10 µg protein in 50 mM Tris-HCl pH 8, 500 mM NaCl, 1 mM dithiothreitol, followed passage through HisTrap HP column. Purified recombinant BAR was dialyzed in storage buffer (12.5 mM Tris-HCl pH 8, 50 mM NaCl, 2 mM dithiothreitol) and concentrated to 13 mg/mL using a ultra-centrifugal filter (10,000 Da MWCO, Amicon EMD Millipore). The purity of recombinant BAR was assessed by SDS-PAGE. Purified BAR was aliquoted, snap-frozen in liquid nitrogen and stored at −80° C. until further use.

BAR protein was incubated with 1 mM acetyl-CoA for >2 hour prior to setting crystal trays. Crystals of BAR were obtained after 3 days at 20° C. in hanging drops containing 1 µL of protein solution (7.5 mg/ml) and 1 µL of reservoir solution (0.18 M calcium acetate, 0.1 M Tris-HCl pH 7, 18% (w/v) PEG 3000, 0.2% N-nonyl β-D-glucopyranoside, 1 mM acetyl-CoA). Several crystals were soaked in reservoir solution supplemented with 30 mM L-phosphinothricin for 30-60 min before freezing. Crystals were frozen in reservoir solution supplemented with 15% ethylene glycol. Acetylation of phosphinothricin occurred during soaking as no density for the acetyl group of acetyl-CoA was observed in the BAR/CoA/phosphinothricin ternary complex. Co-crystallization screens and soaking experiments were performed using aminoadipate and tryptophan at final concentrations between 5-30 mM. However, we could not identify electron density supporting the presence of these substrates within the resolved crystal structures.

X-ray diffraction data were collected on the 24-ID-C beam line of the Structural Biology Center at the Advanced Photon Source (Argonne National Laboratory) equipped with a Pixel Array Detector (Pilatus-6MF). Diffraction intensities were indexed, integrated, and scaled with the iMosflm (Battye, T. G. et al., *Acta Crystallographica. Section D, Biological Crystallo.* 67, 271-281, (2011)) and SCALA (Evans, P. *Acta Crystallographica. Section D, Biological Crystallo.* 62, 72-82 (2006)) programs. Initial phases were determined by molecular replacement using Phaser under Phenix (Adams, P. D. et al., *Acta Crystallographica. Section D, Biological Crystallo.* 66, 213-221, (2010)). Subsequent structural building and refinements utilized Phenix programs (Adams, P. D. et al., supra). Coot was used for graphical map inspection and manual rebuilding of atomic models (Emsley, P. and Cowtan, K. *Acta Crystallographica. Section D, Biological Crystallo.* 60, 2126-32 (2004)). Crystallographic calculations were performed using Phenix. Molecular graphics were produced with the program PyMol.

Heterologous Expression of BAR Mutants and Activity Determination

Single amino acid mutants of BAR were generated using the QuikChange II site-directed mutagenesis kit (Agilent Technologies) and 6×His-BAR in pProEX Hta as template (see Table 3 for primer sequences). PAT from *Streptomyces viridochromogenes* was amplified using primers BAC0327 and BAC0328 from pAG31 vector (Goldstein, A. L. and McCusker, J. H. Yeast 15, 1541-53 (1999)) (Addgene 35124) and cloned into BamHI/HindIII-linearized pProEX Hta by Gibson assembly (New England Biolabs). Wild-type 6×His-BAR, 6×His-BAR mutants and 6×His-PAT were expressed in *E. coli* BL21(DE3) grown in Terrific Broth medium. At an optical density at 600 nm of 0.6, protein expression was induced with 1.0 mM IPTG and cells were grown at 37° C. for 2.5 h. Cells from a 150 mL cultures were harvested by centrifugation, lysed using BPER™ Bacterial Protein Extraction Reagent (Thermo Scientific) and purified by metal affinity using Ni-NTA Agarose (Qiagen). Purified recombinant proteins were concentrated and buffer-exchanged using storage buffer (10 mM Tris-HCl pH 8.0, 0.2 M NaCl, 10% (v/v) glycerol, 1 mM dithiothreitol) and ultra-centrifugal filters (10,000 Da MWCO, Amicon EMD Millipore). The purity of the recombinant proteins was assessed by SDS-PAGE. Final protein concentrations were determined and normalized using a NanoDrop 2000 UV-VIS spectrometer (Thermo Scientific).

Enzyme assays were carried out in 2 mM Tris-HCl pH 8 and 5 mM acetyl-CoA (Sigma-Aldrich) (final reaction volume 12 Reactions were initiated by the addition of purified recombinant protein at 0.2 µM (assays with L-phosphinothricin) or 300 µM (assays with aminoadipate or tryptophan) and incubated at 25° C. for 15 min (phosphinothricin), 165 min (aminoadipate), or 330 min (L-tryptophan). Reactions were stopped by the addition of three volumes of methanol supplemented with 0.5% (v/v) formic acid, centrifuged for 2 min (14,000-16,000 g), and transferred to LC vials.

The assays were analyzed on an Ultimate 3000 Rapid Separation LC system (Thermo Scientific) coupled to a TSQ Quantum Access MAX triple-quadrupole mass spectrometer (Thermo Scientific). Assays on phosphinothricin were analyzed as follows. The normal-phase chromatography system consisted of an 150 mm HILIC column (Kinetex 2.6 µm silica core shell HILIC 100 Å pore, Phenomenex), which was developed using Optima™ LC/MS solvents (Fisher Chemical) with a gradient (flow rate of 0.8 mL min$^{-1}$) of solvent B (50% water, 50% acetonitrile (v/v), 5 mM ammonium formate pH 3) in solvent A (10% water, 90% acetonitrile (v/v), 5 mM ammonium formate pH 3) as follows (all (v/v)): 0% for 2 min, 0% to 70% in 10 min, 70% to 100% in 30 sec, 100% for 90 sec, 100% to 0% in 30 sec and 0% for 3.5 min. The mass spectrometer was configured to perform selected-ion-monitoring scans of 0.5 seconds using Q3 (center mass m/z: 224.068, scan width 1.0 m/z, scan time 0.5 sec). Assays on aminoadipate were analyzed as follows. The reverse-phase chromatography system consisted of an 150 mm C18 column (Kinetex 2.6 µm silica core shell C18 100 Å pore, Phenomenex), which was developed using Optima™ LC/MS solvents (Fisher Chemical) with a gradient (flow rate of 0.6 mL min') of solvent B (acetonitrile with 0.1% (v/v) formic acid) in solvent A (water with 0.1% (v/v) formic acid) as follows (all v/v): 1% for 2 min, 1% to 30% in 9 min, 30% to 99% in 30 sec, 99% for 30 sec, 99% to 1% in 1 min and 1% for 2 min. The mass spectrometer was configured to perform selected-ion-monitoring scans of 0.5 seconds using Q3 (center mass m/z: 204.086, scan width 0.5 m/z, scan time 0.5 sec). Assays on tryptophan were analyzed as follow: the reverse-phase chromatography system consisted of an 150 mm C18 column (Kinetex 2.6 µm silica core shell C18 100 Å pore, Phenomenex) which was developed using Optima™ LC/MS solvents (Fisher Chemical) with a gradient (flow rate of 0.7 mL min') of solvent B (acetonitrile with 0.1% (v/v) formic acid) in solvent A (water with 0.1% (v/v) formic acid) as follows (all v/v): 5% for 1 min, 5% to 99% in 9 min, 99% for 2 min, 99% to 5% in 2 min and 5% for 1 min. The mass spectrometer was configured to perform selected-ion-monitoring scans of 0.5 seconds using Q3 (center mass m/z: 247.108, scan width 0.5 m/z, scan time 0.5 sec).

Analysis of BAR Mutants in Plants

Wild-type BAR from *Streptomyces hygroscopicus*, selected BAR mutants and wild-type PAT from *Streptomyces viridochromogenes* were amplified by PCR (Phusion polymerase; New England Biolabs) from pProEX Hta clones (see above) using primers listed in Table 3 and cloned into Bpil-linearized pICH41308 (Engler, C. et al., *ACS Synthetic Biol.* 3(11), 839-43 (2014)) (Golden Gate entry vector) by Gibson assembly (New England Biolabs). BAR and PAT coding sequences were fused with *Agrobacterium tumefaciens* mannopine synthase promoter (from pICH85281) and terminator (from pICH77901) into the empty binary vector pICH47732 by Golden Gate assembly (Engler, C. et al., *ACS Synthetic Biol.* 3(11), 839-43 (2014)). pICH47732 constructs were transformed into *Agrobacterium tumefaciens* GV3130 strain by electroporation and transformed into *Arabidopsis* Col-0 by the floral dip method (Clough, S. J. and Bent, A. F., *The Plant Journal: for cell and molecular biology* 16, 735-743 (1998)). T1 plants were grown on soil and transformants were selected with Finale® (contains 11.33% glufosinate ammonium; Bayer CropScience) diluted 1:500 in water. Photographs were taken 20 days after herbicide treatment (FIG. 14).

In additional experiments, 90 mg of T1 seeds were sown on soil and transformants were selected with Finale® (contains 11.33% glufosinate ammonium; Bayer CropScience) diluted 1:500 in water. Photographs were taken 10 days after herbicide treatment (FIGS. 15A-15B). This experiment was repeated once with similar results. T2 seeds from 5 to 6 T1 plants were collected for each BAR mutant, sown on soil and transgenic individuals were selected with Finale® diluted 1:500 in water (FIGS. 16A-16D).

To further compare the phosphinothricin tolerance in T2 lines transformed with Y92F, N35T and wild-type BAR, seeds from 5-6 independent lines were germinated on ½ MS medium containing 1% sucrose and 8 µg/mL glufosinate ammonium (45520-Sigma-Aldrich). Seven-day old seedlings were then transformed on soil and further grown for 10 days. Photographs were taken before treatment with four different concentrations of Finale® (0, 0.2×, 1× and 5×; see FIG. 17B for further details on the herbicide concentrations). Plants were further grown for 8 days, photographs were taken (FIG. 17A) and the average aerial mass of each T2 populations was measured (average from 8-9 individuals) (FIG. 17B).

Metabolites were extracted from dark-incubated leaves collected from T1 phosphinothricin-resistant individuals as described above and then analyzed on an Ultimate 3000 Rapid Separation LC system (Thermo Scientific) coupled to a TSQ Quantum Access MAX triple-quadrupole mass spectrometer (Thermo Scientific). The reverse-phase chromatography system consisted of an 150 mm C18 column (Kinetex 2.6 µm silica core shell C18 100 Å pore, Phenomenex) which was developed using Optima™ LC/MS solvents (Fisher Chemical) with a gradient (flow rate of 0.6 mL min$^{-1}$) of solvent B (acetonitrile with 0.1% (v/v) formic acid) in solvent A (water with 0.1% (v/v) formic acid) as follows (all (v/v)): 2% for 3 min, 2% to 99% in 9 min, 99% for 4 min, 99% to 2% in 1 min and 2% for 1 min. The mass spectrometer was configured to perform two selected-reaction-monitoring scans, each for 0.5 seconds, for acetyl-aminoadipate and acetyl-tryptophan. The m/z resolution of Q1 was set to 0.4 FWHM, the nitrogen collision gas pressure of Q2 was set to 1.5 mTorr, and the Q3 scan width was set to 0.500 m/z in both cases. Selected reaction monitoring for acetyl-aminoadipate was as follows: precursor ion selection at 204.086 m/z on positive ion mode, fragmentation at 10 V, and product ion selection at 144.065 m/z. Selected reaction monitoring for acetyl-tryptophan was as follows: precursor ion selection at 247.107 m/z on positive ion mode, fragmentation at 20 V, and product ion selection at 188.070 m/z.

Results

Figure 5A:
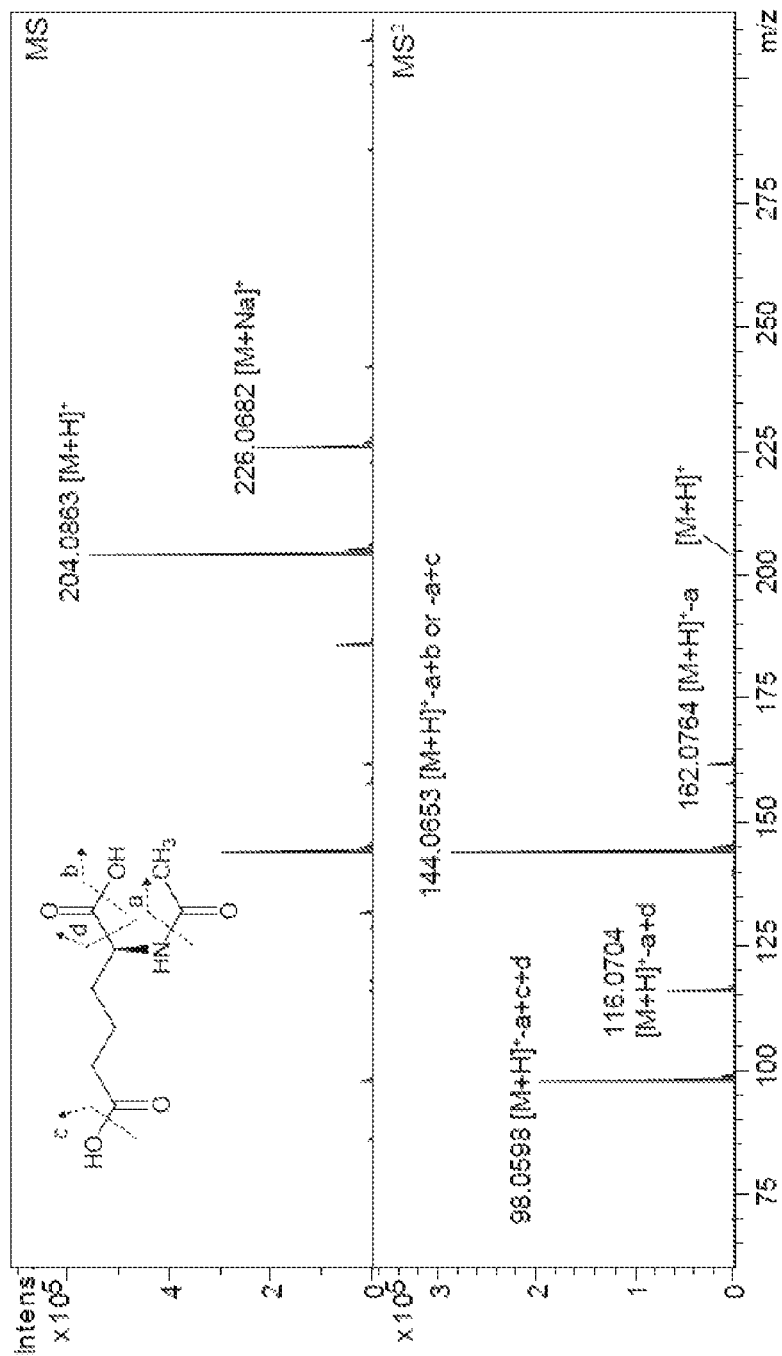
FIGS. 5A and 5B. Liquid chromatography-tandem mass spectrometry (LC-MS2) identification of N-acetyl-L-aminoadipate (FIG. 5A) and N-acetyl-L-tryptophan (FIG. 5B) accumulating in senescent leaves clh2-1 (FLAG_076H05). MS and MS2 spectra, chemical structures and fragmentation pattern are shown. Note that the fragmentation pattern for N-acetyl-L-aminoadipate and N-acetyl-L-tryptophan is concordant with the fragmentation pattern of L-aminoadipate and L-tryptophan as in METLIN database.
Figure 5B:
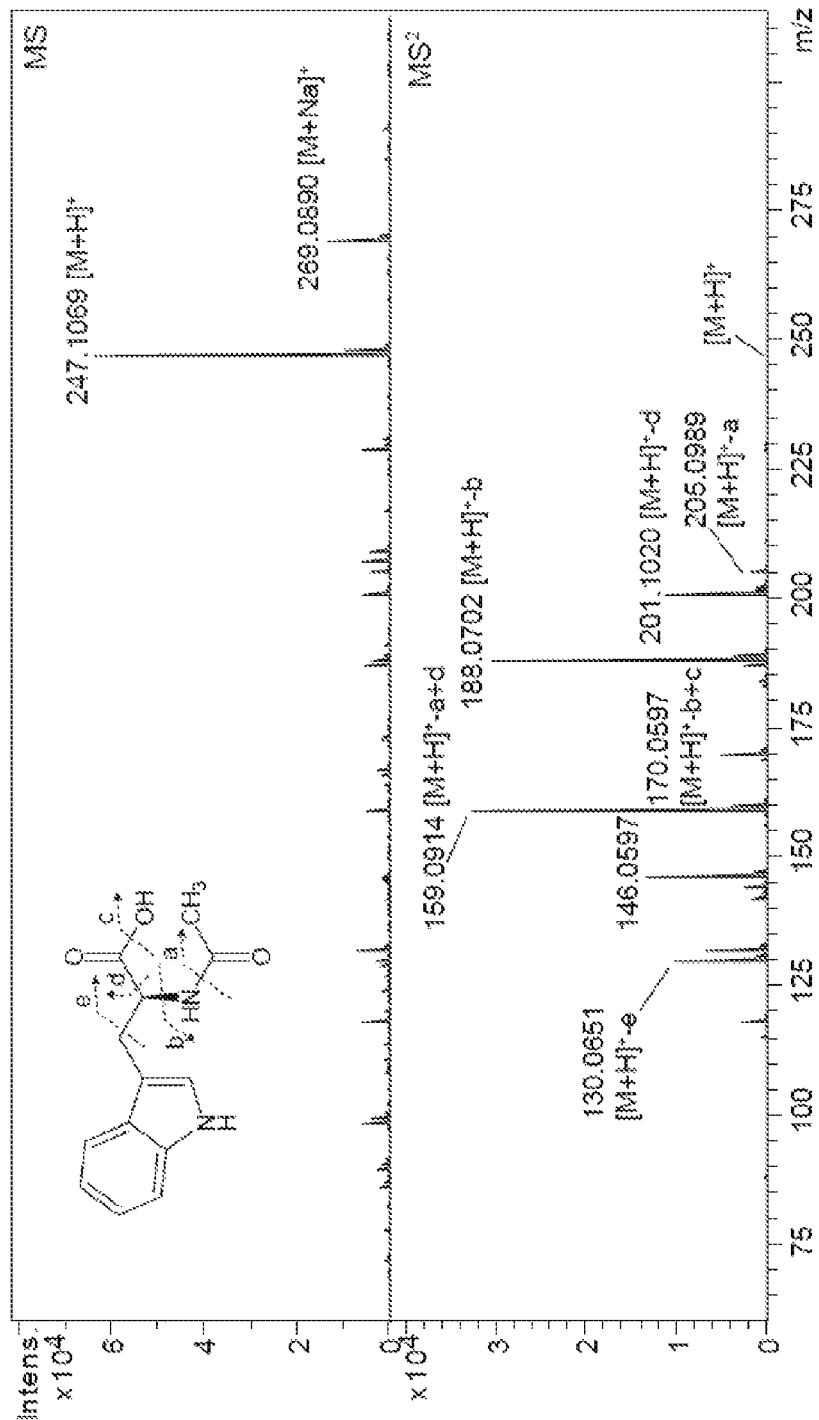

The *Arabidopsis thaliana* clh2-1 mutant (FLAG_76H05) deficient in CHLOROPHYLLASE 2 has been previously characterized (N. Schenk et al., *FEBS letters* 581, 5517-5525 (2007)). Untargeted metabolomics analysis of senescent leaves revealed two metabolites that were ectopically accumulated at high levels in clh2-1 compared to wild type (FIG. 1A). Using liquid chromatography-tandem mass spectrometry (LC-MS$^2$) these two metabolites were identified as N-acetyl-L-aminoadipate and N-acetyl-L-tryptophan (referred to as acetyl-aminoadipate and acetyl-tryptophan respectively hereafter; FIG. 1A and FIG. 5). Since the deficiency of CHLOROPHYLLASE 2, a serine esterase (N. Schenk et al., *FEBS letters* 581, 5517-5525 (2007)) in clh2-1 does not explain the accumulation of these acetylated metabolites, it was hypothesized that the BAR gene present on the transfer DNA (T-DNA) as a selection marker in clh2-1 might be responsible for the formation of these metabolites. To test this, the metabolomics analysis was extended to additional *Arabidopsis* T-DNA insertional mutants unrelated to chlorophyll metabolism that carry either BAR (e.g. mutants from the FLAG (Samson, F. et al., FLAGdb/FST: *Nucleic Acids Research* 30, 94-97 (2002)) and SAIL (Sessions, A. et al., *The Plant Cell* 14, 2985-2994 (2002)) collections) or alternative antibiotic selection markers (e.g. mutants from the SALK (Alonso, J. M. et al., *Science* 301, 653-657 (2003)) and GABI (Rosso, M. G., et al., *Plant Molecular Biology* 53, 247-259 (2003)) collections). Senescent leaves of all six T-DNA mutants carrying BAR manifested accumulation of acetyl-aminoadipate and acetyl-tryptophan, while these metabolites were significantly lower in wild type and T-DNA mutants containing alternative selection markers (FIG. 1B). The abundance of acetyl-aminoadipate and acetyl-tryptophan were estimated to be around 100 µg/g fresh weight and 10 µg/g fresh weight, respectively, in senescent leaf tissue of BAR-containing *Arabidopsis*. These results indicate that the ectopic accumulation of these metabolites is likely resulted from the promiscuous N-acetyltransferase activities of transgenic BAR acting upon plant endogenous amino acids.

Figure 2A:
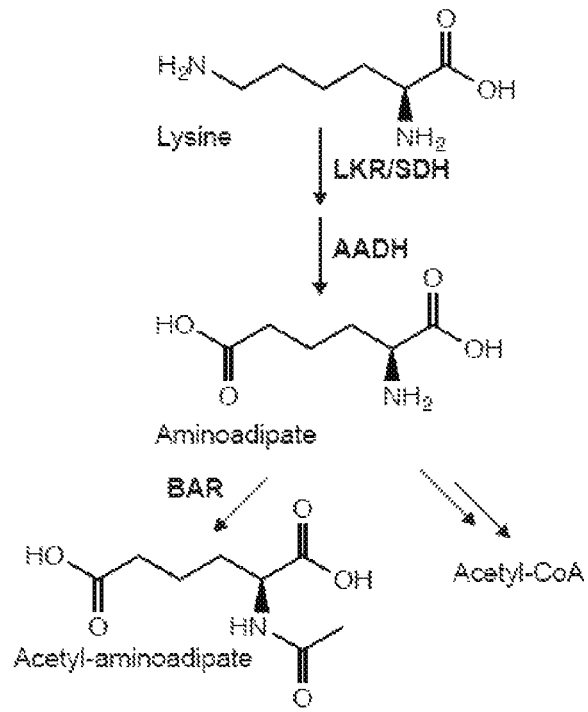
FIGS. 2A and 2B. BAR-dependent accumulation of acetyl-aminoadipate and acetyl-tryptophan is linked to nitrogen remobilization during senescence.
Figure 2B:
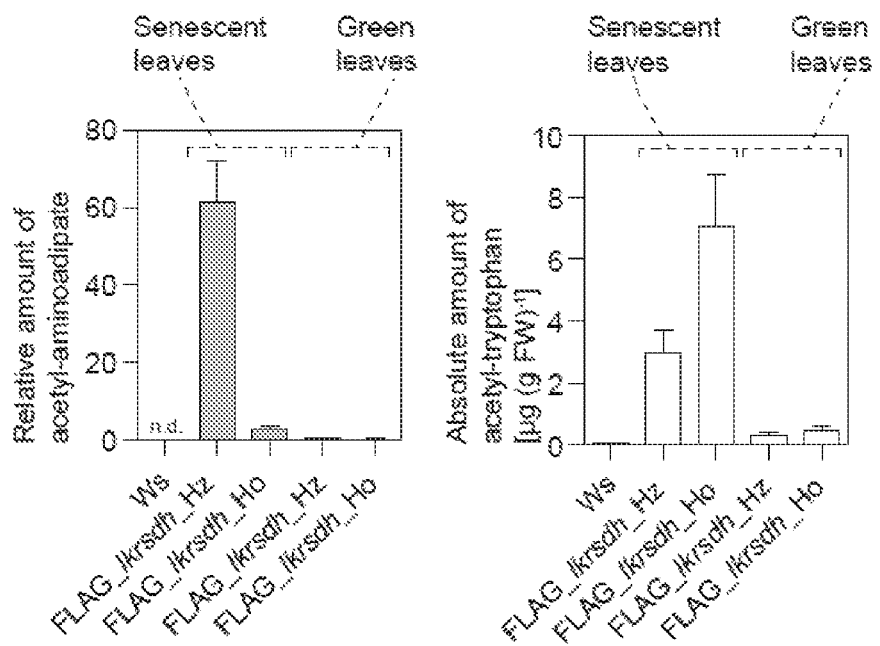
Figure 6:
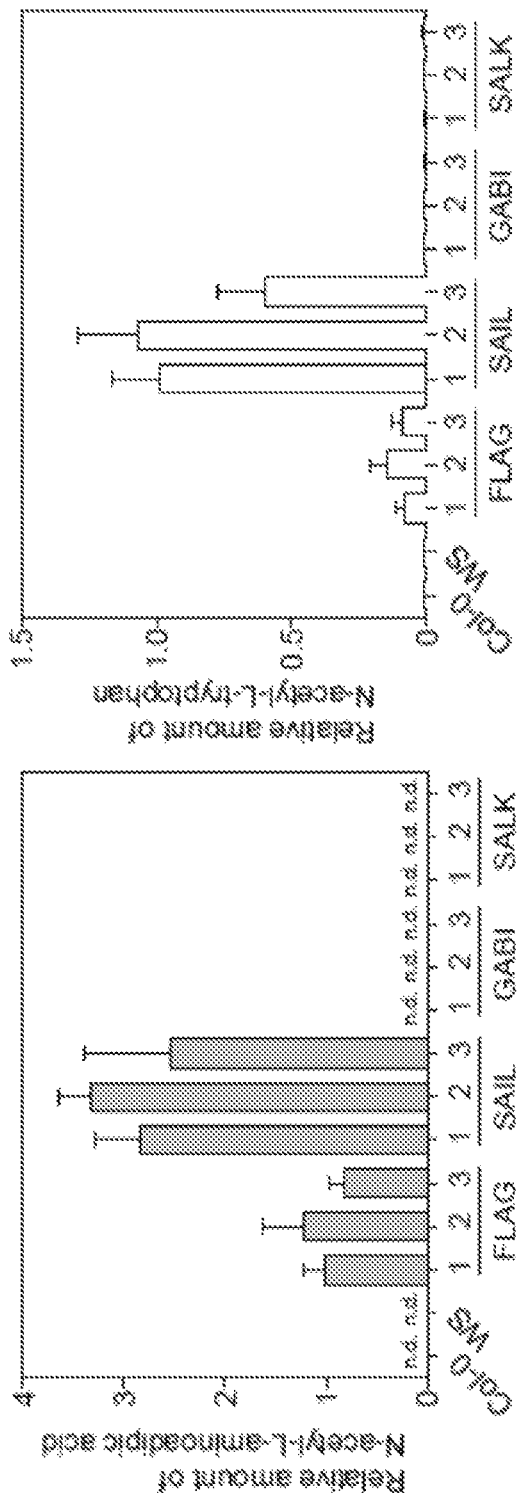
FIG. 6. Relative quantification of acetyl-aminoadipate and acetyl-tryptophan in seeds of *Arabidopsis* mutants from different insertional mutant collections that contains either the BAR gene (SAIL and FLAG) or alternative selection marker genes (SALK and GABI). n.d., not detected.

The concentration of free tryptophan is low in photosynthetically active leaves, but increases significantly in senescent leaves (Soudry, E., et al. *J. of Expt'l Botany* 56, 695-702 (2005)). This is due to enhanced proteolysis during senescence, facilitating remobilization of protein-bound nitrogen and other nutrients to sink organs, such as seeds (Hortensteiner, S. and Feller, U. *J. of Expt'l Botany* 53, 927-937 (2002)). Aminoadipate, an intermediate of lysine degradation, also exhibits a similar accumulation pattern during leaf senescence (Arruda, P. *Trends in Plant Science* 5, 324-330 (2000)). To test whether BAR-catalyzed production of acetyl-aminoadipate is dependent on lysine degradation, an *Arabidopsis* mutant from the FLAG collection was analyzed, FLAG_lkrsdh, in which the BAR-containing T-DNA disrupts At4g33150 encoding the *Arabidopsis* bifunctional lysine-ketoglutarate reductase/saccharopine dehydrogenase (LKR/SDH) (Zhu, X. et al., *Plant Physiology* 126, 1539-1545 (2001)). LKR/SDH catalyzes the first committed step of lysine degradation, and, together with the subsequent aminoadipate semialdehyde dehydrogenase (AADH), converts lysine to aminoadipate (FIG. 2A). In a segregating population for the FLAG_lkrsdh locus, heterozygous, homozygous and wild-type plants were identified by genotyping, and subjected to metabolic profiling by LC-MS after senescence induction (FIG. 2B). Acetyl-aminoadipate occurred at highest level in the heterozygous mutant, but was greatly reduced in the homozygous mutant, suggesting that the ectopic accumulation of acetyl-aminoadipate in BAR-containing plants is dependent on LKR/SDH of the lysine degradation pathway in senescent leaves (FIG. 2A). By contrast, the relative abundance of acetyl-tryptophan in the segregating population of FLAG_lkrsdh generally reflected the copy number of the BAR-containing T-DNA transgene, with approximately 2-fold acetyl-tryptophan level observed in the homozygotes compared to the heterozygotes (FIG. 2B). Furthermore, acetyl-aminoadipate and acetyl-tryptophan levels were approximately 10-20 fold higher in senescent leaves than those in green leaves (FIG. 2B), which is likely due to the increased availability of free tryptophan and aminoadipate during senescence. Consistent with these observations in leaves, ectopic accumulation of acetyl-aminoadipate and acetyl-tryptophan was also observed in seeds of multiple BAR-containing T-DNA mutant lines, but not in the wild-type controls (FIG. 6).

Figure 7B:
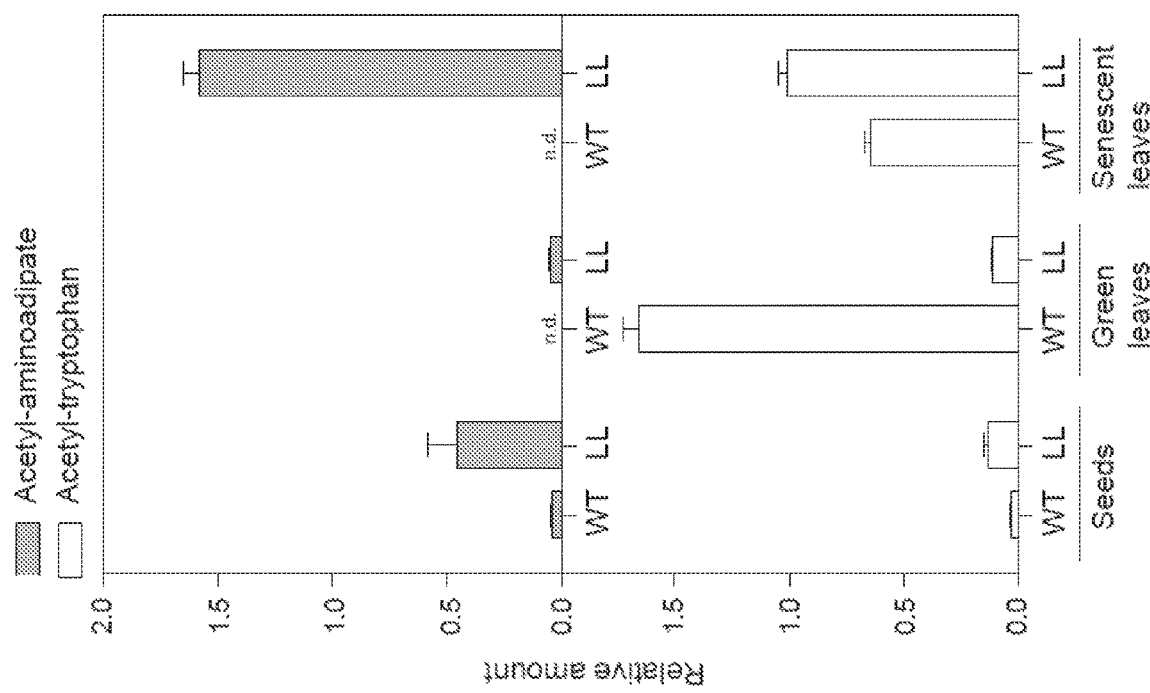
Figure 7C:
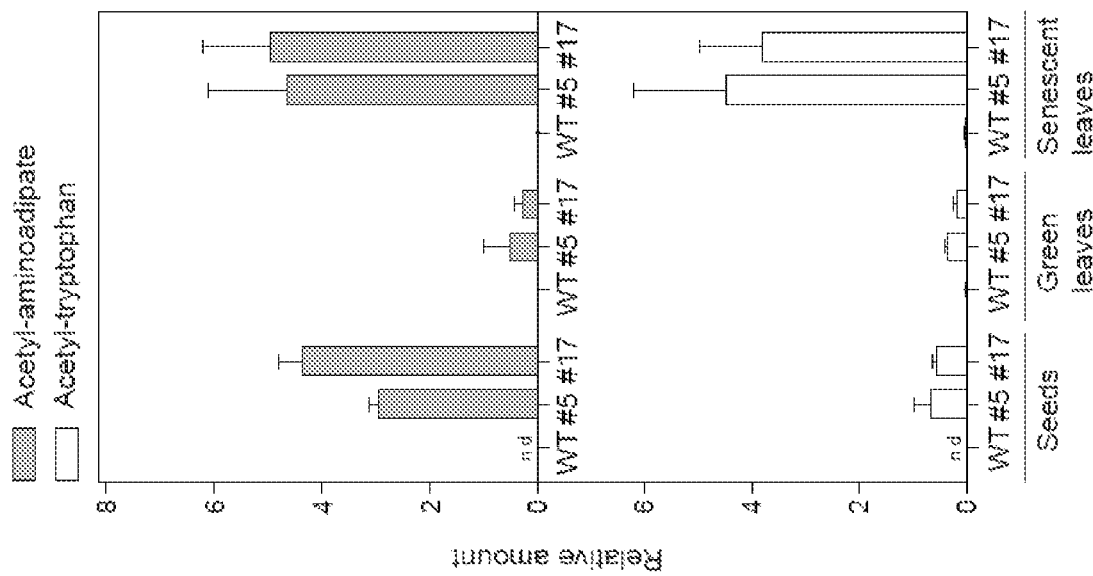
Figure 8B:
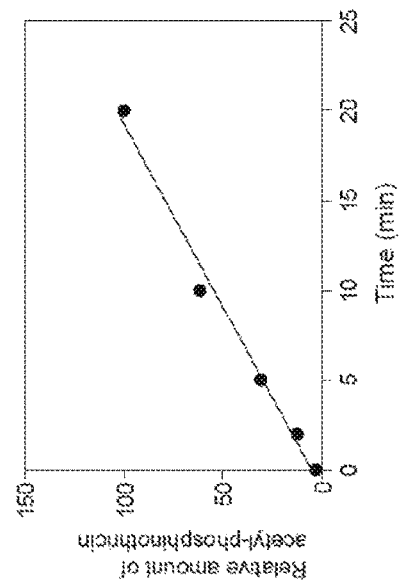
FIGS. 8A-8D. Purification and time-dependent activities of recombinant BAR from *E. coli*.
Figure 8D:
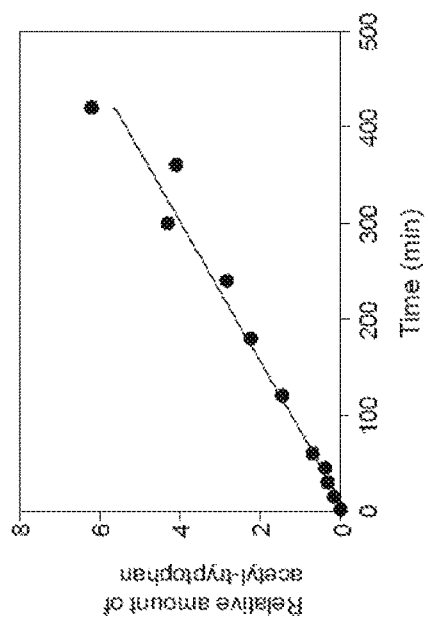
Figure 8A:
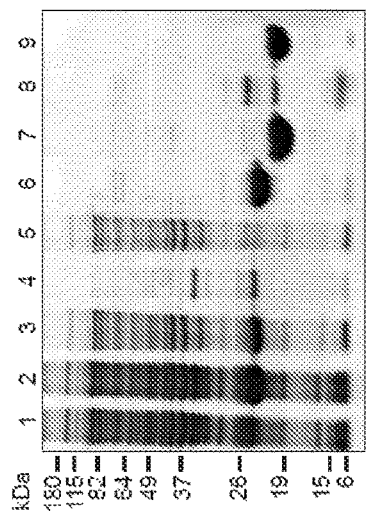
Figure 8C:
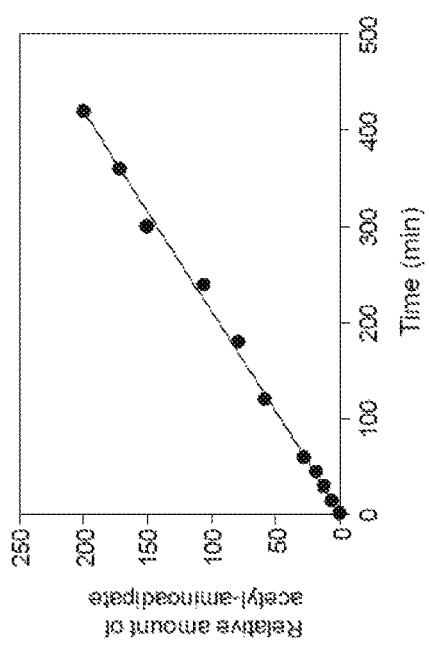

To assess whether the promiscuous activities of transgenic BAR also manifest in other plant hosts, metabolic profiling of various tissue samples from glufosinate-resistant soybean (*Glycine max*) and Chinese mustard (*Brassica juncea*) were performed. Substantially increased accumulation of acetyl-aminoadipate and acetyl-tryptophan was also detected in some tissues of these transgenic crops (FIG. 7), indicating that our findings regarding the in vivo promiscuous activities of BAR may apply broadly to a wide range of BAR-containing transgenic plants.

Figure 3A:
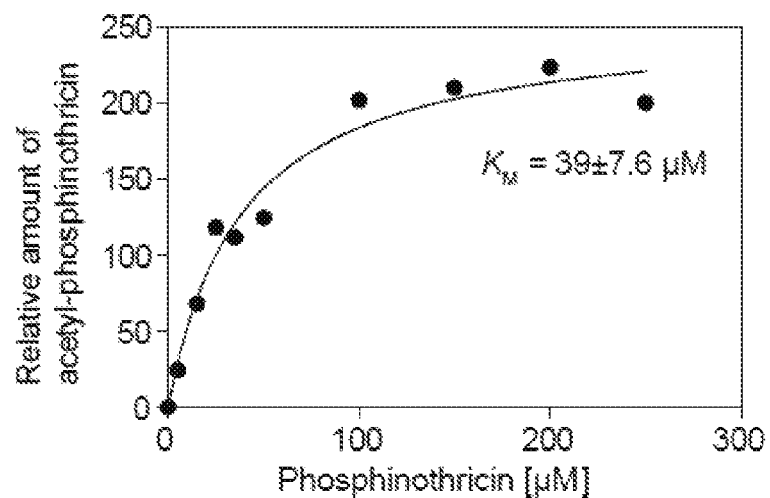
FIGS. 3A and 3B. In vitro enzyme kinetic assays of BAR against native and non-native substrates.
Figure 3B:
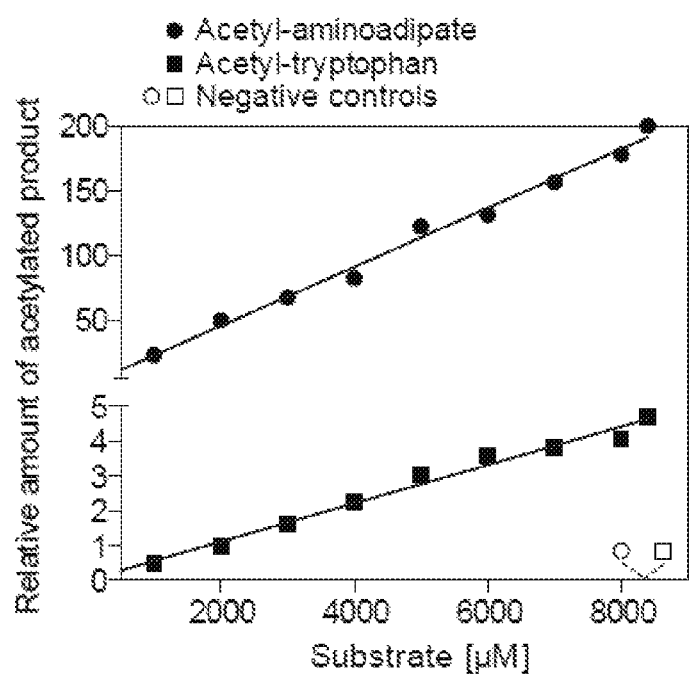

To further characterize the catalytic properties of BAR, pseudo-first-order enzyme kinetic assays were carried out using recombinant BAR against several native and non-native amino acid substrates (FIGS. 3A and 3B and FIGS. 8A-8D). Similar to published data, (Thompson, C. J. et al., *The EMBO J* 6, 2519-2523 (1987); Wehrmann, A. et al., *Nature biotechnology* 14, 1274-1278 (1996); Vinnemeier, J. et al., *Zeitschrift Fur Naturforschung Section C-a Journal of Biosciences* 50, 796-805 (1995)), N-acetylation of phosphinothricin exhibits Michaelis-Menten kinetics with an apparent KM of approximately 39 µM (FIG. 3A). Although BAR clearly showed N-acetyltransferase activities toward aminoadipate and tryptophan, kinetic constants for these non-native substrates could not be established, as both substrates reached solubility limit before reaching saturation concentration for BAR (FIG. 3B). Based on these results, it was estimated that the KM values of BAR against aminoadipate and tryptophan are at least in the millimolar range (FIG. 3B). BAR also exhibited relatively higher catalytic activity toward aminoadipate than tryptophan in vitro (FIG. 3B).

Figure 4A:
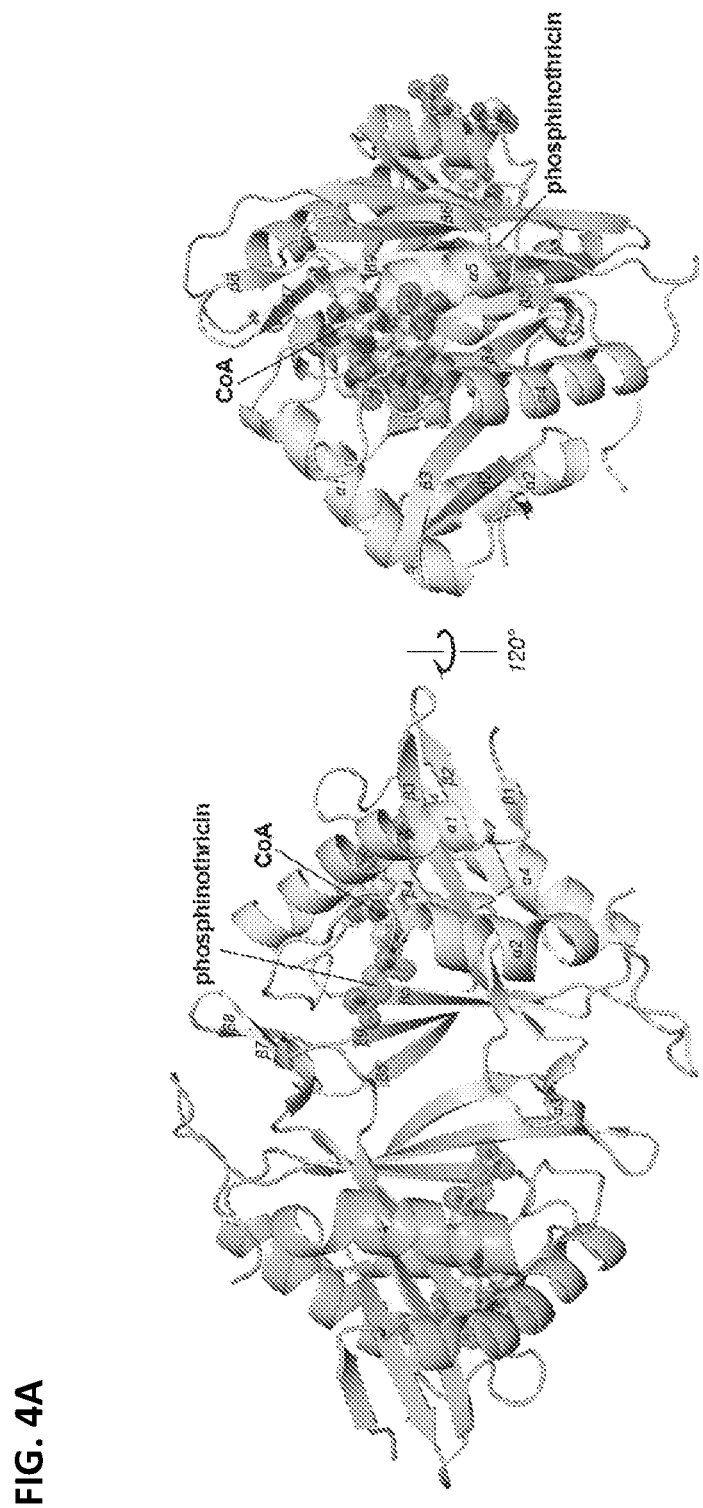
Figure 4B:
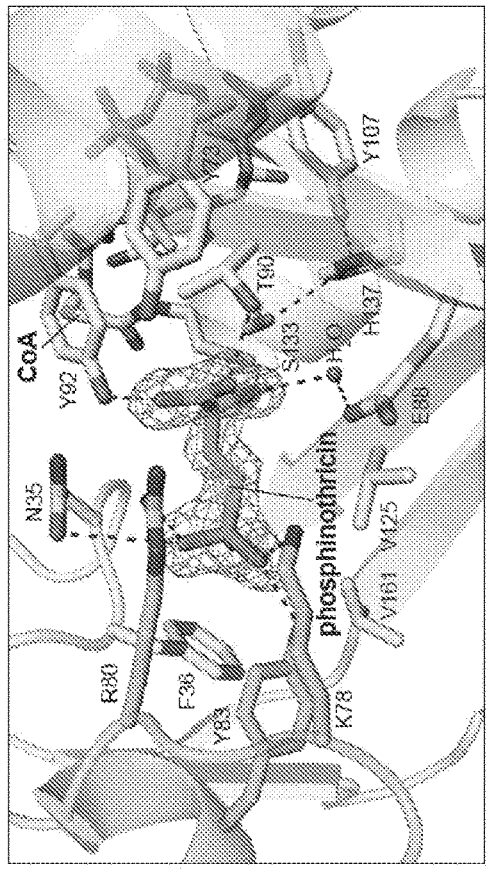
Figure 4C:
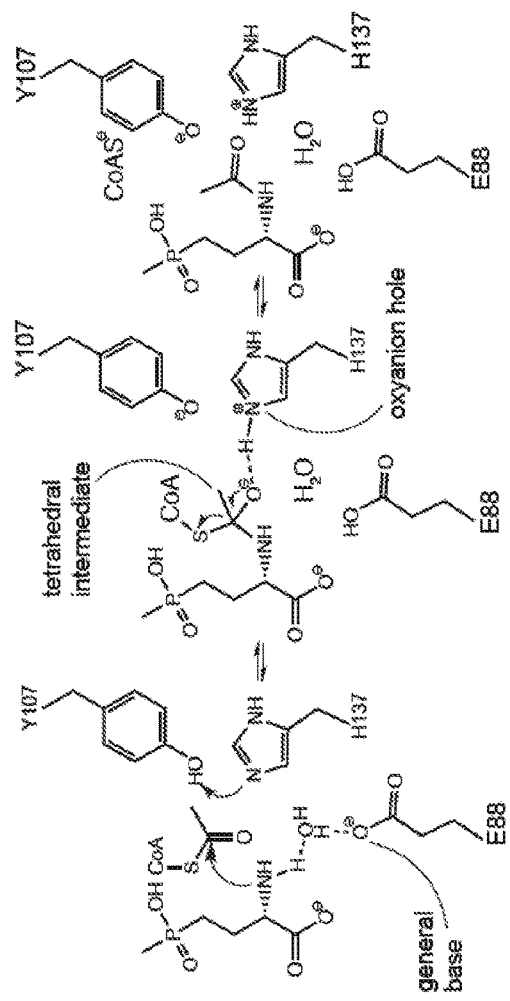
Figure 9A:
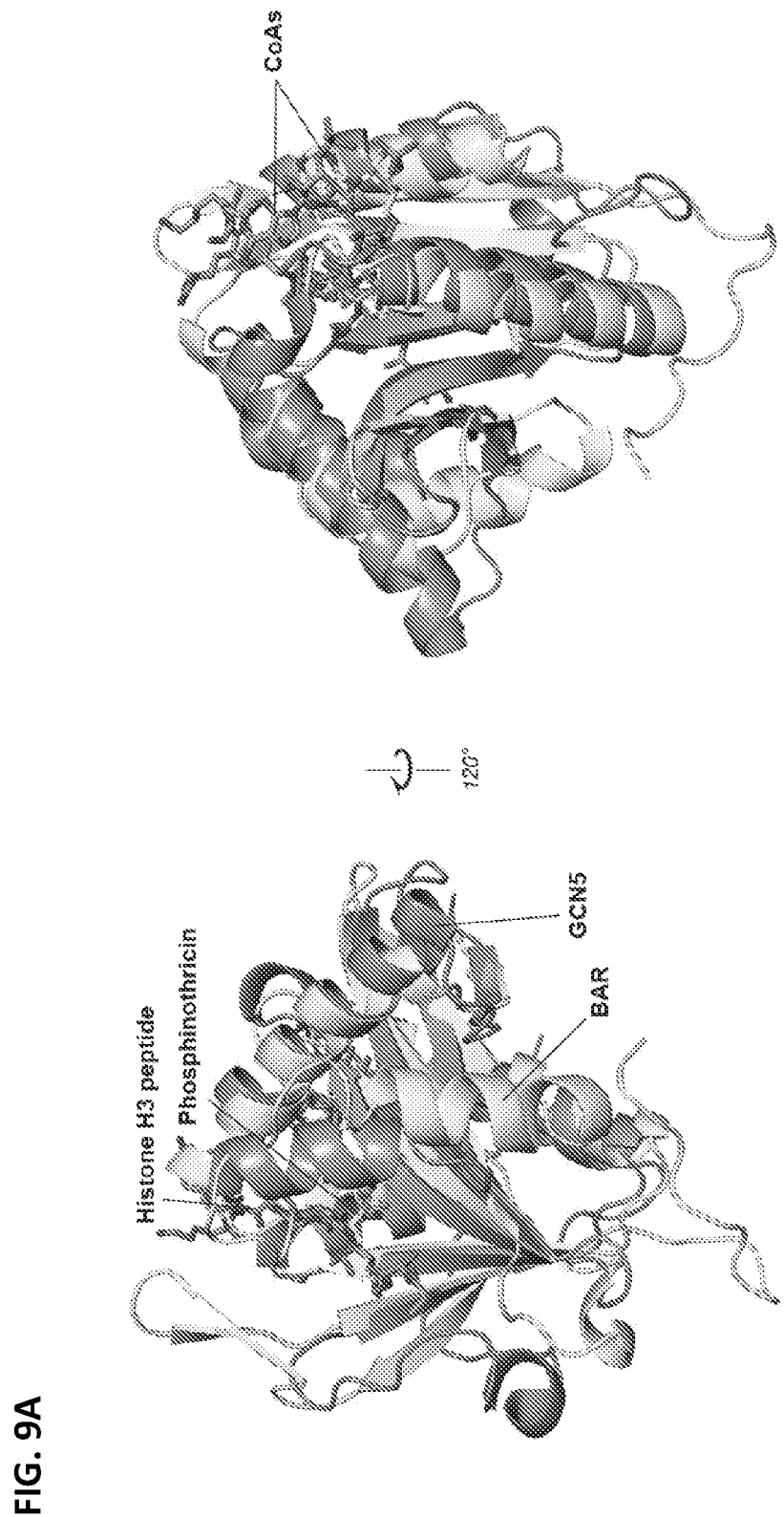
FIGS. 9A and 9B. Structural alignment of BAR/CoA/phosphinothricin ternary complex (yellow) and Tetrahymena GCN5 bound to CoA and histone H3 peptide (red, PBD ID: 1QSN).
Figure 9B:
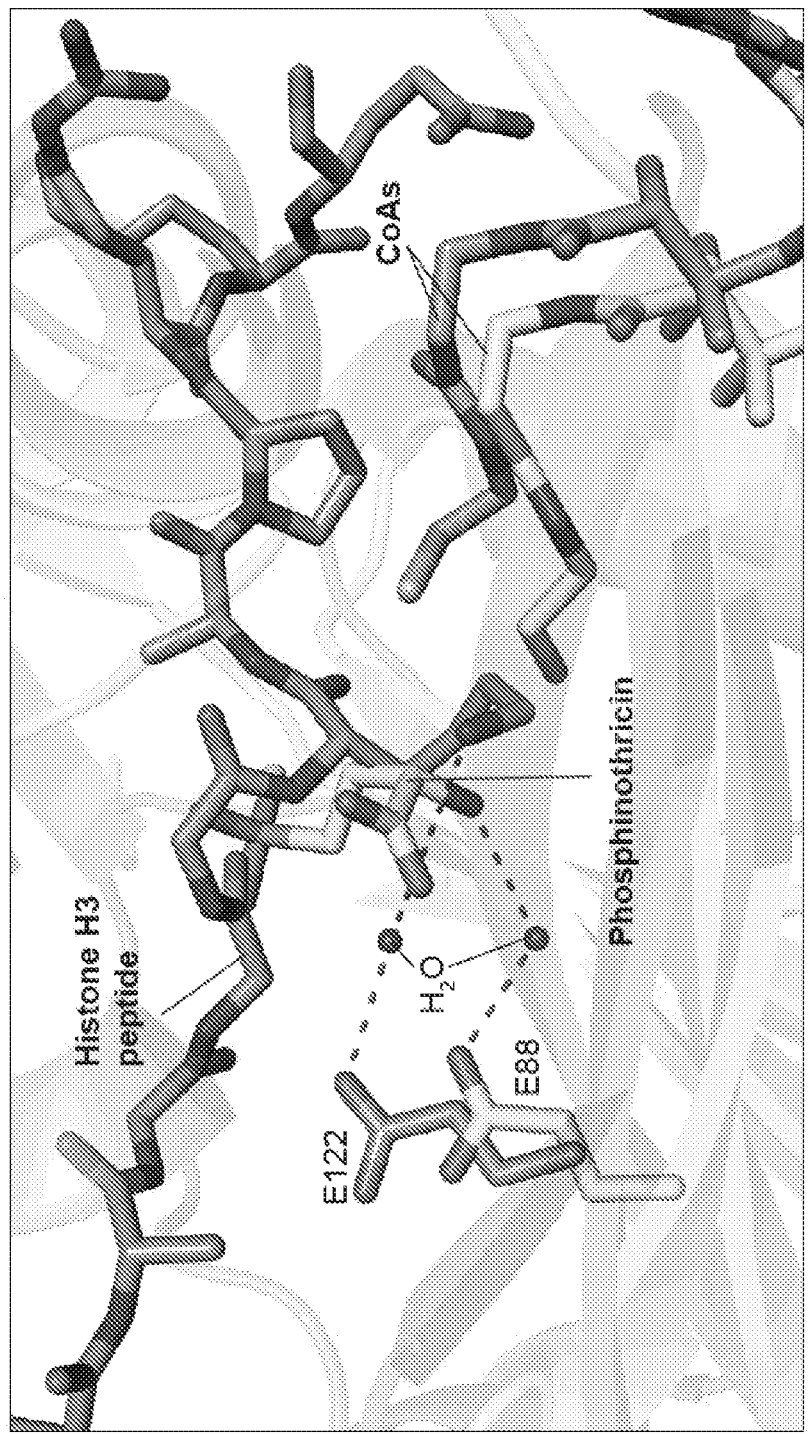
Figure 10A:
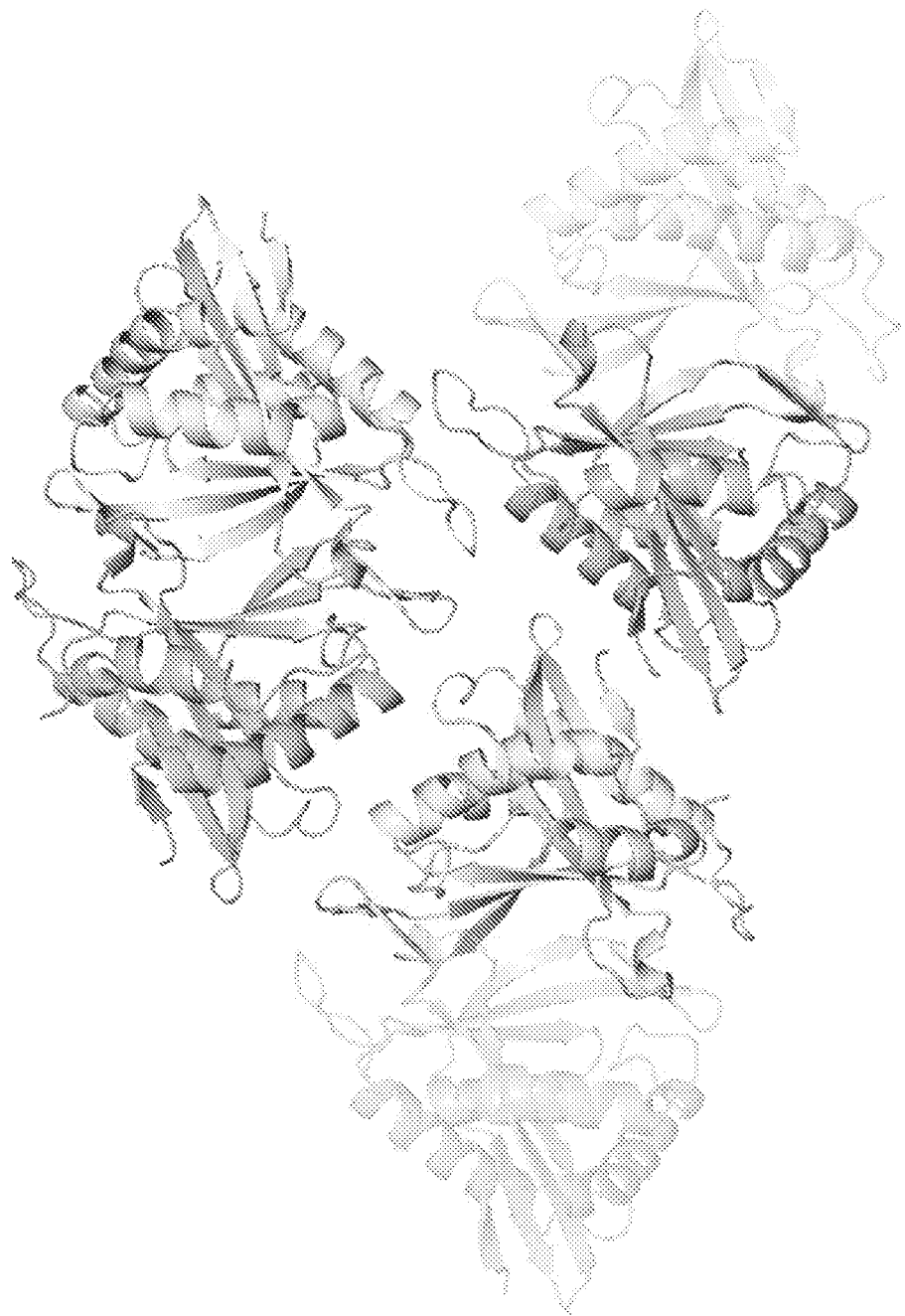
FIGS. 10A and 10B. BAR crystallizes as homodimer with two active sites symmetrically distributed around the dimer interface.
Figure 10B:
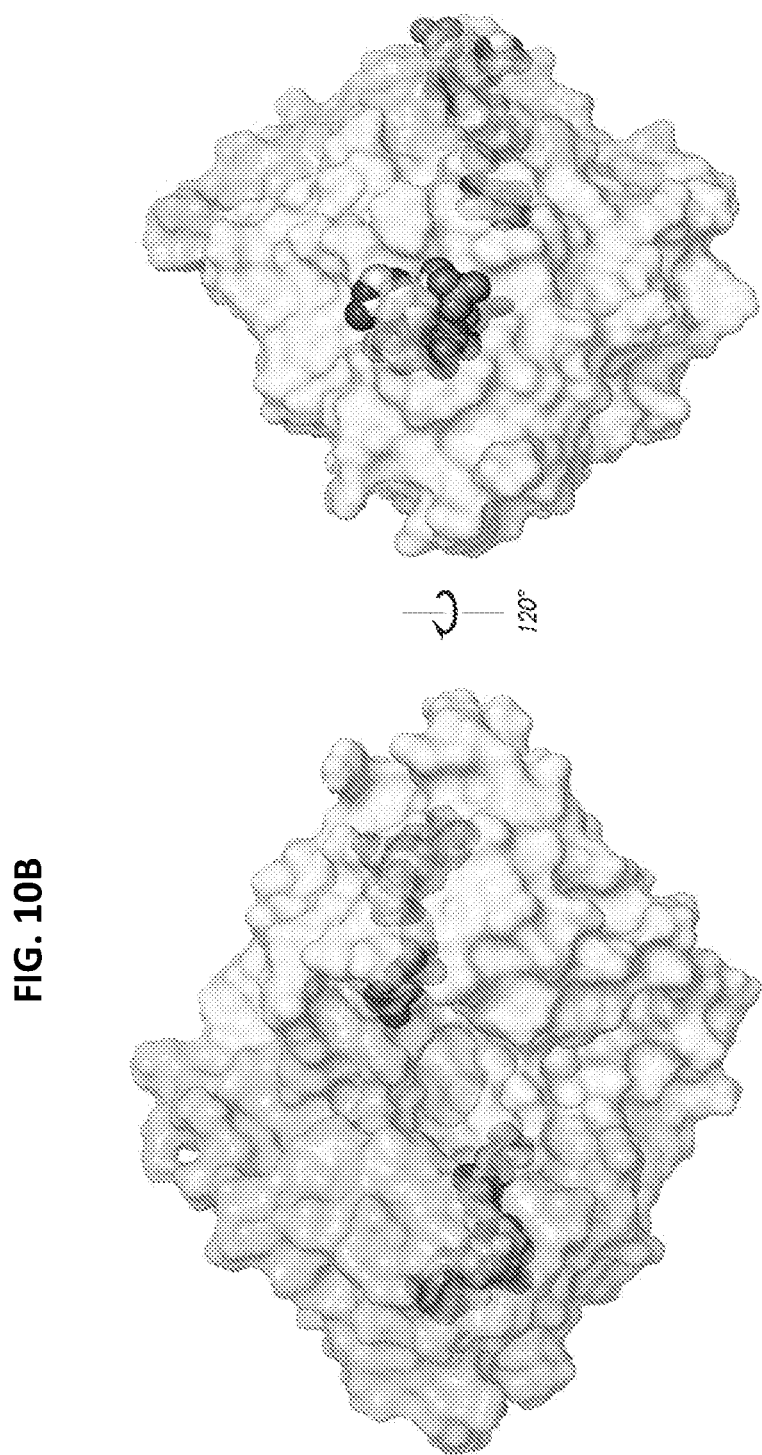
Figure 11A:
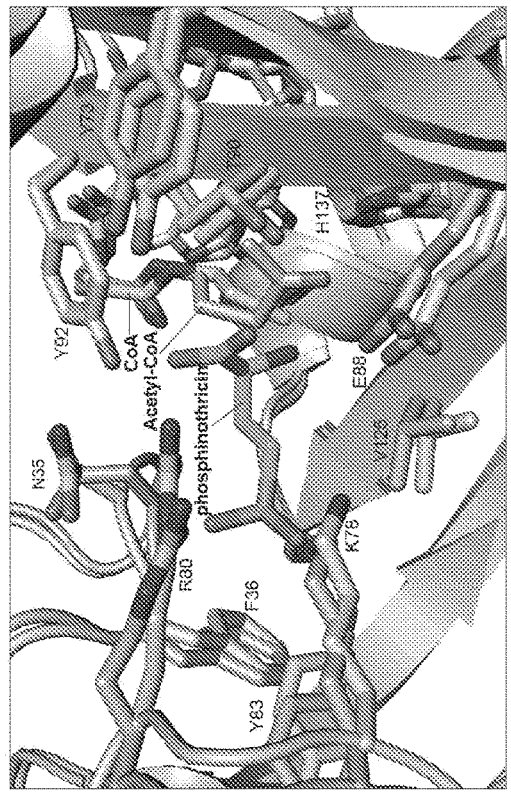
FIGS. 11A and 11B. Structural alignment of the BAR/acetyl-CoA holo complex (purple) with the BAR/CoA/phosphinothricin ternary complex (brown).
Figure 11B:
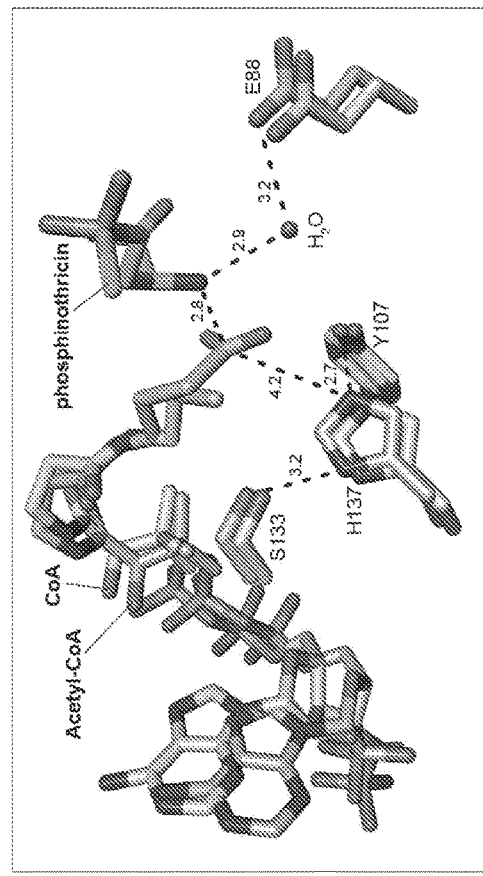

To understand the structural basis for substrate selectivity and catalytic mechanism of BAR, the crystal structures of the BAR/acetyl-CoA holo complex and the BAR/CoA/phosphinothricin ternary complex (see Table 2 for data collection and refinement statistics) were determined. The refined structures revealed that BAR is an αβ protein harboring a globular tertiary structure resembling the previously reported Gcn5-related N-acetyltransferase (GNAT) structures (FIG. 9) (Dyda, F. et al., *Annual Review of Biophysics and Biomolecular Structure* 29, 81-103 (2000)); Vetting, M. W. et al., *Archives of Biochemistry and Biophysics* 433, 212-226 (2005); Srivastava, P. et al., *PLoS ONE* 9, (2014); Rojas, J. R. et al., *Nature* 401, 93-98 (1999)). BAR crystalizes as homodimer with two active sites symmetrically distributed around the dimer interface inside a large open cavity (FIG. 4A and FIG. 10). The cofactor acetyl-CoA binds to a cleft between a4 and a5 on the opposite side of the dimer interface with the acetyl group pointing toward the catalytic center (FIG. 4A). Close examination of the BAR/acetyl-CoA and BAR/CoA/phosphinothricin structures illuminates the catalytic mechanism of BAR (FIG. 4B, FIG. 4C and FIG. 11). Similar to other GNATs, BAR utilizes a conserved catalytic Glu88 as a general base to deprotonate the amino group of phosphinothricin through a water molecule as the proton shuttle (FIG. 4B, FIG. 4C and FIG. 11) (Rojas, J. R. et al., *Nature* 401, 93-98 (1999)). The deprotonated amino group then undergoes nucleophilic attack on the carbonyl carbon of acetyl-CoA to produce a tetrahedral intermediate, which is further stabilized by an oxyanion hole composed of a positively charged His137 and its proton donor Tyr107 (FIG. 4C and FIG. 11). It is noteworthy that the structural feature underlying this oxyanion hole in BAR must have arisen independently from the functionally analogous oxyanion hole previously described in the histone acetyltransferase GCN5, featuring a backbone amide nitrogen instead (Rojas, J. R. et al., *Nature* 401, 93-98 (1999)). In the final step of the catalytic cycle, coenzyme A is released from the tetrahedral intermediate as a leaving group to produce acetyl-phosphinothricin (FIG. 4C).

Figure 4D:
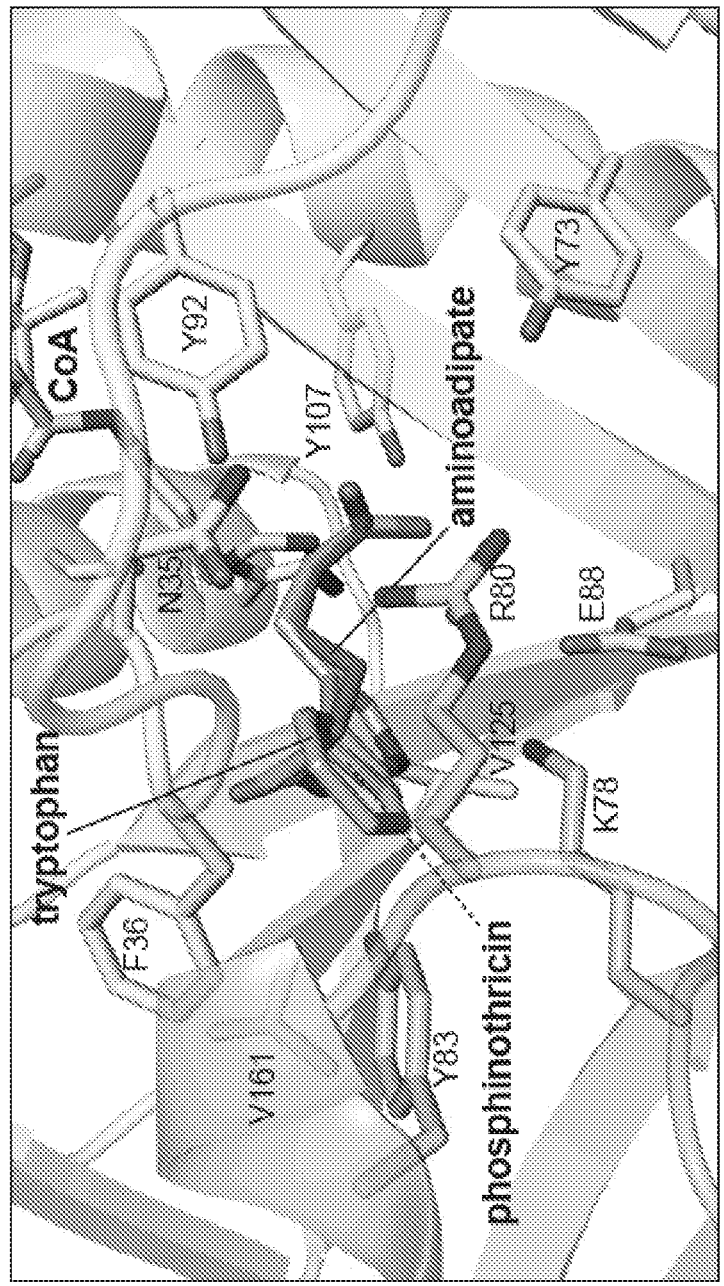

The BAR/CoA/phosphinothricin ternary structure also reveals active-site residues involved in phosphinothricin binding. Within each active site, the methylphosphoryl group of the substrate engages hydrophobic interactions with the surrounding Phe36, Gly127, and Val161 from the same monomer, whereas the two phosphoryl oxygen atoms are coordinated by Lys78, Arg80, and Tyr83 from the β3-loop-α3 region of the neighboring monomer via a set of H-bonds and electrostatic interactions (FIG. 4B). Furthermore, the amino acid group of phosphinothricin is properly positioned at the catalytic center by a H-bond network involving the backbone carbonyl group of Val125 and the side chains of Thr90 and Tyr92 (FIG. 4B). Despite various attempts using co-crystallization and soaking techniques, the complex structures of BAR containing aminoadipate or tryptophan could not be obtained, reflecting the low binding affinity of these promiscuous substrates to BAR. Simulated docking of these substrates within the active site of the BAR/CoA/phosphinothricin structure reveals fewer favorable interactions as well as potential steric clashes with the surrounding residues compared to phosphinothricin (FIG. 4D).

Figure 4E:
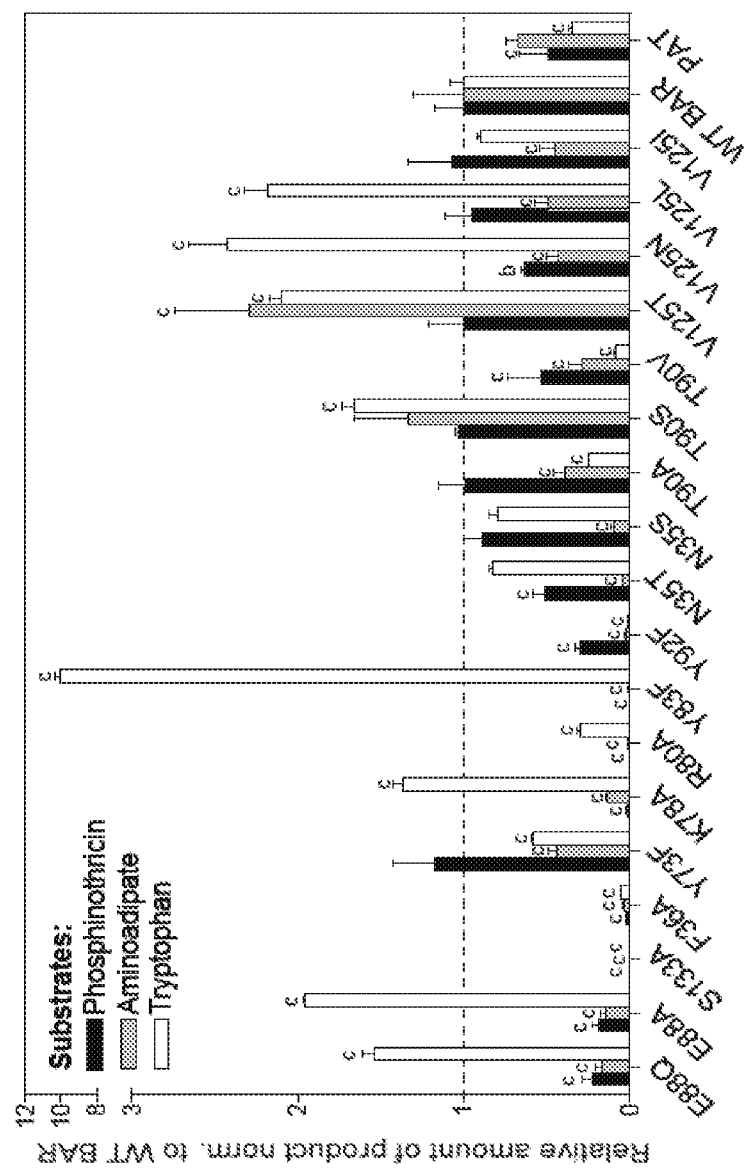
Figure 12:
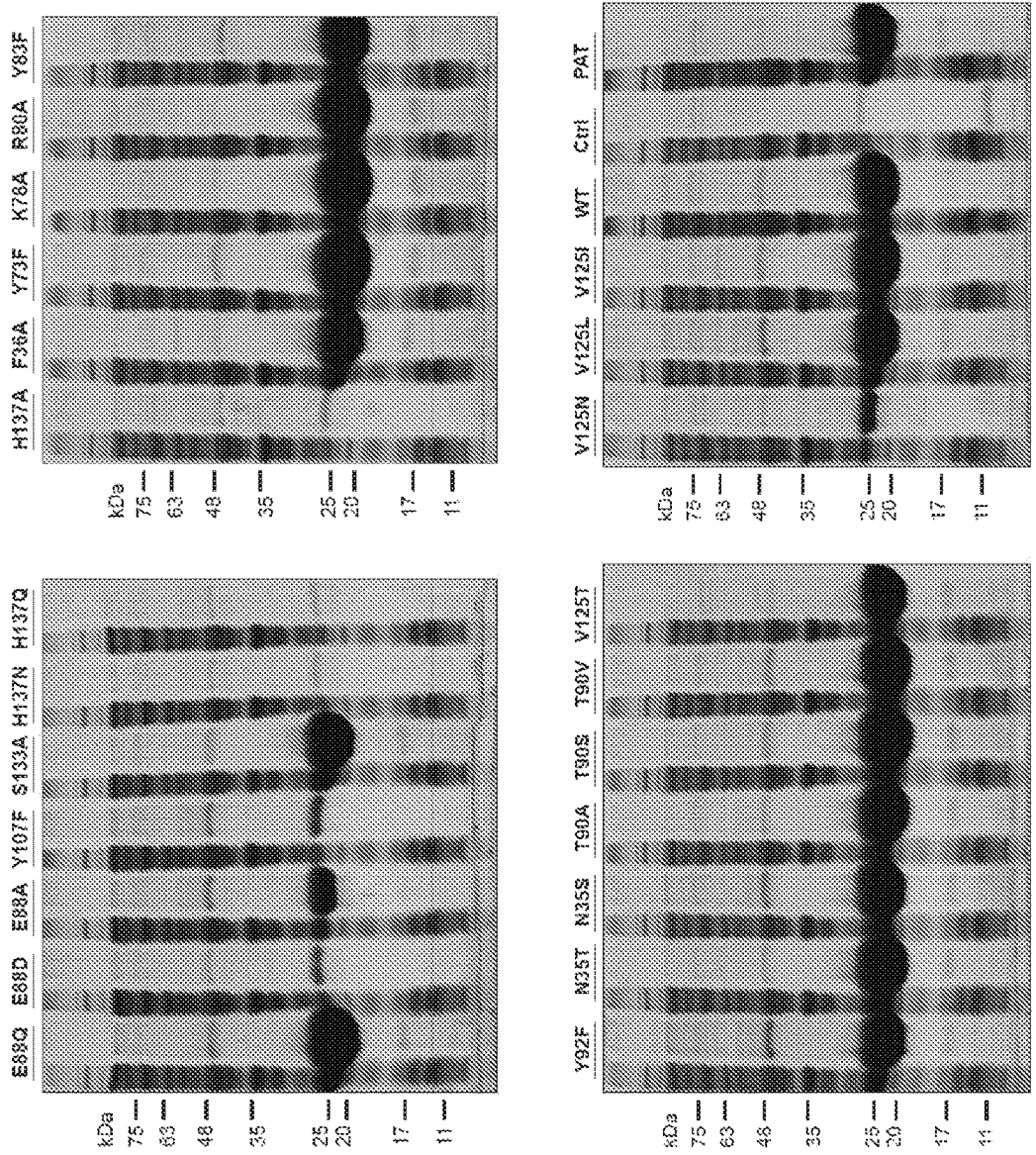
FIG. 12. Expression and purification of 23 recombinant mutant versions of BAR from *Streptomyces hygroscopicus* and wild-type PAT from *Streptomyces viridochromogenes*. Left SDS-PAGE lane, soluble fraction of *E. coli* lysate; right lane, purified protein; Ctrl, empty vector.

Site-directed mutagenesis followed by biochemical assays confirmed the roles of many active-site residues predicted by structural analysis (FIG. 4E and FIG. 12). Mutating the catalytic Glu88 to Ala or Gln greatly reduces the activity of BAR toward phosphinothricin and aminoadipate. Nevertheless, these mutants exhibit higher activity toward tryptophan than that of the wild-type enzyme (FIG. 4E), suggesting that tryptophan may be deprotonated through an alternative mechanism independent of Glu88 and/or the first deprotonation step is not rate-limiting for BAR-catalyzed acetyl-tryptophan formation. H137A and Y107A mutants failed to yield soluble recombinant protein (FIG. 12), preventing the role of the oxyanion hole in catalysis to be directly assessed. Thus, this analysis was carried out indirectly by mutating Ser133, a residue that forms a H-bond with the imidazole ring it-nitrogen of His137 (FIG. 4B). The resulting S133A mutant exhibits completely abolished N-acetyltransferase activity toward the three tested substrates, suggesting an essential role of Ser133 in catalysis, likely through proper positioning of the oxyanion hole (FIG. 4E and FIG. 11). Mutants affecting phosphinothricin-binding residues, including F36A, K78A, R80A, Y83F, Y92F, generally show significantly reduced activity toward phosphinothricin and aminoadipate, while K78A and Y83F display increased activity toward the more hydrophobic substrate tryptophan (FIG. 4E).

With the structural information of BAR, the enzyme was engineered through structure-guided mutagenesis to repress its undesired promiscuous activities toward aminoadipate and tryptophan while maintaining its native activity against phosphinothricin. Residue positions Asn35, Tyr73, Thr90, Tyr92, and Val125 were selected for targeted mutagenesis based on structural analysis as well as multiple sequence alignment containing BAR, PAT, and other closely related homologs from bacteria (FIG. 4B, FIG. 4D and FIG. 13). A set of eleven mutants was first characterized in vitro (FIG. 4E), and eight of those were further tested in transgenic Arabidopsis (FIGS. 4F and 4G). All eight BAR mutants confer phosphinothricin resistance in Arabidopsis (FIG. 4F and FIG. 14). Metabolic profiling of these transgenic lines confirmed that mutations in select active-site residues of BAR can modulate the in vivo promiscuous activities of BAR toward aminoadipate and tryptophan (FIG. 4G). Notably, transgenic Arabidopsis plants containing N35T, N35S, V125L or V125I BAR mutants display significantly reduced levels of acetyl-aminoadipate compared to plants containing wild-type BAR (FIG. 4G). Moreover, plants expressing Y92F BAR mutant exhibit significantly reduced levels of both acetyl-aminoadipate and acetyl-tryptophan compared to plants containing wild-type BAR. In contrast, the V125T BAR mutant shows increased promiscuity against both aminoadipate and tryptophan in vitro and in vivo (FIGS. 4E and 4G).

TABLE 2

| Data collection and refinement statistics | | |
| --- | --- | --- |
| | BAR-ACO (PDB ID: XXX) | BAR-COA-Phosphinothricin (PDB ID: XXX) |
| Resolution range (Å) | 44.79-1.4 (1.45-1.4) | 62.52-1.8 (1.864-1.8) |
| Space group | P 1 21 1 | P 1 21 1 |
| Unit cell (Å) (°) | 65.1 71.5 84.05 90 104.33 90 | 64.18 66.11 86.15 90 103.06 90 |
| Total reflections | 238978 (13056) | 93996 (4082) |
| Unique reflections | 131315 (10035) | 54563 (3385) |
| Multiplicity | 1.8 (1.3) | 1.7 (1.2) |
| Completeness (%) | 89.48 (68.67) | 83.62 (52.15) |
| Mean I/sigma(I) | 8.84 (0.98) | 5.41 (1.03) |
| Wilson B-factor (Å$^2$) | 14.16 | 16.54 |
| R-merge | 0.03773 (0.5096) | 0.07711 (0.3945) |
| R-meas | 0.05336 | 0.109 |
| CC1/2 | 0.998 (0.611) | 0.96 (0.781) |
| CC* | 1 (0.871) | 0.99 (0.936) |
| R-work | 0.1611 (0.3214) | 0.2094 (0.3383) |
| R-free | 0.1931 (0.3451) | 0.2421 (0.3723) |
| Number of non-hydrogen atoms | 6939 | 6246 |
| macromolecules | 5659 | 5551 |
| ligands | 236 | 278 |
| water | 1044 | 417 |
| Protein residues | 706 | 708 |
| RMS(bonds) (Å) | 0.007 | 0.003 |
| RMS(angles) (°) | 1.27 | 0.91 |
| Ramachandran favored (%) | 99 | 98 |
| Ramachandran outliers (%) | 0 | 0.14 |
| Clashscore | 5.91 | 4.81 |
| Average B-factor (Å$^2$) | 20.9 | 22.4 |
| macromolecules | 18.4 | 21.5 |
| ligands | 21 | 28.1 |
| solvent | 34.4 | 30.3 |

Values in parentheses are for highest resolution shell.

TABLE 3

| List of primers | | |
| --- | --- | --- |
| Primer name | Sequence (5'-3') | Used for |
| SALK_T-DNA_LBb1.3 | ATTTTGCCGATTTCGGAAC (SEQ ID NO: 3) | Genotyping Arabidopsis T-DNA lines |
| GABL_T-DNA_o8409 | ATATTGACCATCATACTCATTGC (SEQ ID NO: 4) | Genotyping Arabidopsis T-DNA lines |
| SAIL_T-DNA_LB1 | GCCTTTTCAGAAATGGATAAATAGCCTTGCTTCC (SEQ ID NO: 5) | Genotyping Arabidopsis T-DNA lines |
| SALK_130606_SALK-1_LP | TATTGCCTGATGGATCGATTC (SEQ ID NO: 6) | Genotyping Arabidopsis T-DNA lines |
| SALK_13060_SALK-1_RP | CAGCCATTAACTTAGGTTGCG (SEQ ID NO: 7) | Genotyping Arabidopsis T-DNA lines |
| SALK_051823C_SALK-2_LP | AGAACATGGATGTGCCAGAAG (SEQ ID NO: 8) | Genotyping Arabidopsis T-DNA lines |
| SALK_051823C_SALK-2_RP | CGCTGCATATACCATGTGATG (SEQ ID NO: 9) | Genotyping Arabidopsis T-DNA lines |

TABLE 3-continued

List of primers

| Primer name | Sequence (5'-3') | Used for |
|---|---|---|
| SALK_110649_SALK-3_LP | TAAAGGGAGCTTCGAGTCTCC (SEQ ID NO: 10) | Genotyping Arabidopsis T-DNA lines |
| SALK_110649_SALK-3_RP | TCACCGCATCTTCCTAAAATG (SEQ ID NO: 11) | Genotyping Arabidopsis T-DNA lines |
| SAIL_1165_B02_SAIL-1_LP | CCACTAGACCATTGGCTTTTTC (SEQ ID NO: 12) | Genotyping Arabidopsis T-DNA lines |
| SAIL_1165_B02_SAIL-1_RP | ATCGATGATGTCTTCGTGCTC (SEQ ID NO: 13) | Genotyping Arabidopsis T-DNA lines |
| SAIL_503_C03_SAIL-2_LP | AAAACCAACAAAAGGCAATCC (SEQ ID NO: 14) | Genotyping Arabidopsis T-DNA lines |
| SAIL_503_C03_SAIL-2_RP | CGAGTGCGATACAGAGATTCC (SEQ ID NO: 15) | Genotyping Arabidopsis T-DNA lines |
| SAIL_1235_D10_SAIL-3_LP | TGCTCACTTTTTCCTTTGGTG (SEQ ID NO: 16) | Genotyping Arabidopsis T-DNA lines |
| SAIL_1235_D10_SAIL-3_RP | CACCATATGCAACACTTGTGG (SEQ ID NO: 17) | Genotyping Arabidopsis T-DNA lines |
| GABI_453E01_GABI-1_LP | TTTTGTCTCACCTGCTTCCAC (SEQ ID NO: 18) | Genotyping Arabidopsis T-DNA lines |
| GABI_453E01_GABI-1_RP | TCATGAAGGCACGTCTTTACC (SEQ ID NO: 19) | Genotyping Arabidopsis T-DNA lines |
| GABI_833F02_GABI-2_LP | TCAACAGACCAAGGTGGAATC (SEQ ID NO: 20) | Genotyping Arabidopsis T-DNA lines |
| GABI_833F02_GABI-2_RP | CTCATCCTGCTCTTGACCTTG (SEQ ID NO: 21) | Genotyping Arabidopsis T-DNA lines |
| GABI_453A08_GABI-3_LP | ATAGCTAGCATCGGATGCAAC (SEQ ID NO: 22) | Genotyping Arabidopsis T-DNA lines |
| GABI_453A08_GABI-3_RP | TGTACAGGTTATCGGTGAGCC (SEQ ID NO: 23) | Genotyping Arabidopsis T-DNA lines |
| FLAG_076H05_clh2-1_FLAG-1_LP | TTCAAATCTCCAATTATTTTGTTTG (SEQ ID NO: 24) | Genotyping Arabidopsis T-DNA lines |
| FLAG_076H05_clh2-1_FLAG-1_RP | AACAATTCCGATAGTACCATTTCC (SEQ ID NO: 25) | Genotyping Arabidopsis T-DNA lines |
| FLAG_271B02_FLAG-2_LP | TTTCATGAAGTTGTCAACACCTG (SEQ ID NO: 26) | Genotyping Arabidopsis T-DNA lines |
| FLAG-271B02_FLAG-2_RP | TTGTTGGGAGATTTTGTGGTC (SEQ ID NO: 27) | Genotyping Arabidopsis T-DNA lines |
| FLAG_495A09_FLAG-3_LP | CATTGGTTGCTTAATTGGTCC (SEQ ID NO: 28) | Genotyping Arabidopsis T-DNA lines |
| FLAG_495A09_FLAG-3_RP | GCATGAAAGGTTCTCTTTCCC (SEQ ID NO: 29) | Genotyping Arabidopsis T-DNA lines |
| FLAG_271B12_FLAG-lkrsdh_LP | TCATTCTGCCTTCTCCATCAG (SEQ ID NO: 30) | Genotyping Arabidopsis T-DNA lines |
| FLAG_271B12_FLAG-lkrsdh_RP | AGCAACAACGATATTTCGTGG (SEQ ID NO: 31) | Genotyping Arabidopsis T-DNA lines |
| SAIL_BAR_F_pPROEX | CCGGAATTCATGAGCCCAGAACGACGCC (SEQ ID NO: 32) | Cloning BAR in pProEx Hta (forward) |
| SAIL_BAR_R_pPROEX | CCCAAGCTTTCAGATCTCGGTGACGGGC (SEQ ID NO: 33) | Cloning BAR in pProEx Hta (reverse) |
| BAC0255 | ACACGGTCGACTGGGCCGTCCAGTC (SEQ ID NO: 34) | Site-directed mutagenesis of BAR (E88Q) in pProEx Hta (forward) |

TABLE 3-continued

List of primers

| Primer name | Sequence (5'-3') | Used for |
|---|---|---|
| BAC0256 | GTACACGGTCGAATCGGCC GTCCAGTCG (SEQ ID NO: 35) | Site-directed mutagenesis of BAR (E88D) in pProEx Hta (forward) |
| BAC0257 | GTACACGGTCGACGCGGCC GTCCAGTC (SEQ ID NO: 36) | Site-directed mutagenesis of BAR (E88A) in pProEx Hta (forward) |
| BAC0258 | CAGCAGGTGGGTGAAGAGC GTGGAGCC (SEQ ID NO: 37) | Site-directed mutagenesis of BAR (Y107F) in pProEx Hta (forward) |
| BAC0259 | GTGCATGCGCACGGCCGGG TCGTTGGGC (SEQ ID NO: 38) | Site-directed mutagenesis of BAR (S133A) in pProEx Hta (forward) |
| BAC0260 | CGAGCGCCTCGTTCATGCGC ACGCT (SEQ ID NO: 39) | Site-directed mutagenesis of BAR (H137N) in pProEx Hta (forward) |
| BAC0261 | CCGAGCGCCTCCTGCATGCG CAC (SEQ ID NO: 40) | Site-directed mutagenesis of BAR (H137Q) in pProEx Hta (forward) |
| BAC0262 | TCCGAGCGCCTCGGCCATGC GCACGTC (SEQ ID NO: 41) | Site-directed mutagenesis of BAR (H137A) in pProEx Hta (forward) |
| BAC0263 | GCGGCTCGGTACGGGCGTTG ACCGTGCTTG (SEQ ID NO: 42) | Site-directed mutagenesis of BAR (F36A) in pProEx Hta (forward) |
| BAC0264 | TCGCCGGCATCGCCTTCGCG GGCC (SEQ ID NO: 43) | Site-directed mutagenesis of BAR (Y73F) in pProEx Hta (forward) |
| BAC0265 | GCGTTGCGTGCCGCCCAGGG GCCCGC (SEQ ID NO: 44) | Site-directed mutagenesis of BAR (K78A) in pProEx Hta (forward) |
| BAC0266 | GTCGTAGGCGTTGGCTGCCT TCCAGGGG (SEQ ID NO: 45) | Site-directed mutagenesis of BAR (R80A) in pProEx Hta (forward) |
| BAC0267 | CCGTCCAGTCGAAGGCGTTG CGTGC (SEQ ID NO: 46) | Site-directed mutagenesis of BAR (Y83F) in pProEx Hta (forward) |
| BAC0268 | GGGAGACGTACACGACCGA CTCGGCCGTCC (SEQ ID NO: 47) | Site-directed mutagenesis of BAR (T90V) in pProEx Hta (forward) |
| BAC0269 | GGGGAGACGAACACGGTCG ACTCGGCC (SEQ ID NO: 48) | Site-directed mutagenesis of BAR (Y92F) in pProEx Hta (forward) |
| BAC0270 | GCTCGGTACGGAAGGTGAC CGTGCTTGTC (SEQ ID NO: 49) | Site-directed mutagenesis of BAR (N35T) in pProEx Hta (forward) |
| BAC0271 | GCTCGGTACGGAAGCTGAC CGTGCTTGTC (SEQ ID NO: 50) | Site-directed mutagenesis of BAR (N35S) in pProEx Hta (forward) |
| BAC0272 | GAGACGTACACGGCCGACT CGGCCGTC (SEQ ID NO: 51) | Site-directed mutagenesis of BAR (T90A) in pProEx Hta (forward) |
| BAC0273 | GAGACGTACACGCTCGACTC GGCCGTC (SEQ ID NO: 52) | Site-directed mutagenesis of BAR (T90S) in pProEx Hta (forward) |
| BAC0274 | GGGAGACGTACACGACCGA CTCGGCCGTCC (SEQ ID NO: 53) | Site-directed mutagenesis of BAR (T90V) in pProEx Hta (forward) |
| BAC0275 | GGGCAGCCCGATGGTAGCG ACCACGCTC (SEQ ID NO: 54) | Site-directed mutagenesis of BAR (V125T) in pProEx Hta (forward) |
| BAC0276 | GGGCAGCCCGATGTTAGCG ACCACGCTC (SEQ ID NO: 55) | Site-directed mutagenesis of BAR (V125N) in pProEx Hta (forward) |
| BAC0277 | GCCCGATGAGAGCGACCAC GCTCTTG (SEQ ID NO: 56) | Site-directed mutagenesis of BAR (V125L) in pProEx Hta (forward) |
| BAC0278 | CAGCCCGATGATAGCGACC ACGCTCTTGAAGC (SEQ ID NO: 57) | Site-directed mutagenesis of BAR (V125I) in pProEx Hta (forward) |
| BAC0279 | GACTGGACGGCCCAGTCGA CCGTGT (SEQ ID NO: 58) | Site-directed mutagenesis of BAR (E88Q) in pProEx Hta (reverse) |

TABLE 3-continued

List of primers

| Primer name | Sequence (5'-3') | Used for |
|---|---|---|
| BAC0280 | CGACTGGACGGCCGATTCG ACCGTGTAC (SEQ ID NO: 59) | Site-directed mutagenesis of BAR (E88D) in pProEx Hta (reverse) |
| BAC0281 | GACTGGACGGCCGCGTCGA CCGTGTAC (SEQ ID NO: 60) | Site-directed mutagenesis of BAR (E88A) in pProEx Hta (reverse) |
| BAC0282 | GGCTCCACGCTCTTCACCCA CCTGCTG (SEQ ID NO: 61) | Site-directed mutagenesis of BAR (Y107F) in pProEx Hta (reverse) |
| BAC0283 | GCCCAACGACCCGGCCGTG CGCATGCAC (SEQ ID NO: 62) | Site-directed mutagenesis of BAR (S133A) in pProEx Hta (reverse) |
| BAC0284 | AGCGTGCGCATGAACGAGG CGCTCG (SEQ ID NO: 63) | Site-directed mutagenesis of BAR (H137N) in pProEx Hta (reverse) |
| BAC0285 | GTGCGCATGCAGGAGGCGC TCGG (SEQ ID NO: 64) | Site-directed mutagenesis of BAR (H137Q) in pProEx Hta (reverse) |
| BAC0286 | GAGCGTGCGCATGGCCGAG GCGCTCGGA (SEQ ID NO: 65) | Site-directed mutagenesis of BAR (H137A) in pProEx Hta (reverse) |
| BAC0287 | CAAGCACGGTCAACGCCCG TACCGAGCCGC (SEQ ID NO: 66) | Site-directed mutagenesis of BAR (F36A) in pProEx Hta (reverse) |
| BAC0288 | GGCCCGCGAAGGCGATGCC GGCGA (SEQ ID NO: 67) | Site-directed mutagenesis of BAR (Y73F) in pProEx Hta (reverse) |
| BAC0289 | GCGGGCCCCTGGGCGGCAC GCAACGC (SEQ ID NO: 68) | Site-directed mutagenesis of BAR (K78A) in pProEx Hta (reverse) |
| BAC0290 | CCCCTGGAAGGCAGCCAAC GCCTACGAC (SEQ ID NO: 69) | Site-directed mutagenesis of BAR (R80A) in pProEx Hta (reverse) |
| BAC0291 | GCACGCAACGCCTTCGACTG GACGG (SEQ ID NO: 70) | Site-directed mutagenesis of BAR (Y83F) in pProEx Hta (reverse) |
| BAC0292 | GGACGGCCGAGTCGGTCGT GTACGTCTCCC (SEQ ID NO: 71) | Site-directed mutagenesis of BAR (T90V) in pProEx Hta (reverse) |
| BAC0293 | GGCCGAGTCGACCGTGTTCG TCTCCCC (SEQ ID NO: 72) | Site-directed mutagenesis of BAR (Y92F) in pProEx Hta (reverse) |
| BAC0294 | GACAAGCACGGTCACCTTCC GTACCGAGC (SEQ ID NO: 73) | Site-directed mutagenesis of BAR (N35T) in pProEx Hta (reverse) |
| BAC0295 | GACAAGCACGGTCAGCTTCC GTACCGAGC (SEQ ID NO: 74) | Site-directed mutagenesis of BAR (N35S) in pProEx Hta (reverse) |
| BAC0296 | GACGGCCGAGTCGGCCGTG TACGTCTC (SEQ ID NO: 75) | Site-directed mutagenesis of BAR (T90A) in pProEx Hta (reverse) |
| BAC0297 | GACGGCCGAGTCGAGCGTG TACGTCTC (SEQ ID NO: 76) | Site-directed mutagenesis of BAR (T90S) in pProEx Hta (reverse) |
| BAC0298 | GGACGGCCGAGTCGGTCGT GTACGTCTCCC (SEQ ID NO: 77) | Site-directed mutagenesis of BAR (T90V) in pProEx Hta (reverse) |
| BAC0299 | GAGCGTGGTCGCTACCATCG GGCTGCCC (SEQ ID NO: 78) | Site-directed mutagenesis of BAR (V125T) in pProEx Hta (reverse) |
| BAC0300 | GAGCGTGGTCGCTAACATCG GGCTGCCC (SEQ ID NO: 79) | Site-directed mutagenesis of BAR (V125N) in pProEx Hta (reverse) |
| BAC0301 | CAAGAGCGTGGTCGCTCTCA TCGGGC (SEQ ID NO: 80) | Site-directed mutagenesis of BAR (V125L) in pProEx Hta (reverse) |
| BAC0302 | GCTTCAAGAGCGTGGTCGCT ATCATCGGGCTG (SEQ ID NO: 81) | Site-directed mutagenesis of BAR (V125I) in pProEx Hta (reverse) |
| BAC0327 | ATTTTCAGGGCGCCATGGAT CCGATGGGTAGCCCAGAAC GACG (SEQ ID NO: 82) | Cloning PAT in pProEx Hta by Gibson assembly (forward) |

TABLE 3-continued

List of primers

| Primer name | Sequence (5'-3') | Used for |
|---|---|---|
| BAC0328 | CATCCGCCAAAACAGCCAA GCTTTTAGATCTGTGTGACG GGCCG(SEQ ID NO: 83) | Cloning PAT in pProEx Hta by Gibson assembly (reverse) |
| BAC0385 | CGATTCATTAATCACTCTGT GGTCTCAAATGAGCCCAGA ACGACGC (SEQ ID NO: 84) | Cloning wild-type BAR and mutants in Golden Gate pICH41308 by Gibson assembly (forward) |
| BAC0386 | CCACTGAAGAGCCACTTCGT GGTCTCAAAGCTCAGATCTC GGTGACGGGC (SEQ ID NO: 85) | Cloning wild-type BAR and mutants in Golden Gate pICH41308 by Gibson assembly (reverse) |
| BAC0387 | CGATTCATTAATCACTCTGT GGTCTCAAATGGGTAGCCCA GAACGACG (SEQ ID NO: 86) | Cloning PAT in Golden Gate pICH41308 by Gibson assembly (forward) |
| BAC0388 | CCACTGAAGAGCCACTTCGT GGTCTCAAAGCTTAGATCTG TGTGACGGGCCG (SEQ ID NO: 87) | Cloning PAT in Golden Gate pICH41308 (reverse) by Gibson assembly (reverse) |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A host cell comprising a nucleic acid encoding a bialaphos resistance (BAR) protein variant, wherein the BAR protein variant possesses modified acetyltransferase activity against tryptophan or aminoadipate, or both, as compared to the wildtype BAR protein comprising the sequence set forth in SEQ ID NO: 1, and wherein the variant comprises:
 an amino acid sequence that has at least 98% sequence identity to SEQ ID NO: 1, and
 one or more amino acid substitutions relative to SEQ ID NO: 1, wherein the one or more substitutions are selected from N35T, N35S, Y73F, E88A, E88Q, T90A, Y92F, V125L, V125I, F36A, R80A, K78A, Y83F, or V125T.

2. A host cell comprising a nucleic acid encoding a phosphinothricin acetyltransferase (PAT) variant, wherein the PAT protein variant possesses modified acetyltransferase activity against tryptophan or aminoadipate, or both, as compared to the wildtype PAT protein comprising the sequence set forth in SEQ ID NO: 2, and wherein the variant comprises:
 an amino acid sequence that has at least 98% sequence identity to SEQ ID NO: 2, and
 one or more amino acid substitutions relative to SEQ ID NO: 2, wherein the one or more substitutions are selected from N35T, N35S, Y73F, E88A, E88Q, T90A, Y92F, V125L, V125I, F36A, R80A, K78A, Y83F, or V125T.

3. The host cell of claim 1, wherein the BAR protein variant confers phosphinothricin resistance in a plant, and comprises one substitution relative to SEQ ID NO: 1, wherein the substitution is selected from: N35T, N35S, Y73F, T90A, Y92F, V125L, V125T, or V125I.

4. The host cell of claim 1, wherein the host cell is an Agrobacterium.

5. The host cell of claim 1, wherein the host cell is a plant cell.

6. A method of generating a transgenic plant, comprising:
a) introducing into a plant a nucleic acid encoding
 i) a BAR protein variant, wherein the BAR protein variant possesses modified acetyltransferase activity against tryptophan or aminoadipate, or both, as compared to the wildtype BAR protein comprising the sequence set forth in SEQ ID NO: 1, and wherein the variant comprises:
  an amino acid sequence that has at least 98% sequence identity to SEQ ID NO: 1, and
  one or more amino acid substitutions relative to SEQ ID NO: 1, wherein the one or more substitutions are selected from N35T, N35S, Y73F, E88A, E88Q, T90A, Y92F, V125L, V125I, F36A, R80A, K78A, Y83F, or V125T; or
 ii) a PAT protein variant, wherein the PAT protein variant possesses modified acetyltransferase activity against tryptophan or aminoadipate, or both, as compared to the wildtype PAT protein comprising the sequence set forth in SEQ ID NO: 2, and wherein the variant comprises:
  an amino acid sequence that has at least 98% sequence identity to SEQ ID NO: 2, and
  one or more amino acid substitutions relative to SEQ ID NO: 2, wherein the one or more substitutions are selected from N35T, N35S, Y73F, E88A, E88Q, T90A, Y92F, V125L, V125I, F36A, R80A, K78A, Y83F, or V125T; and
b) integrating the nucleic acid into the genome of the plant,
thereby generating a transgenic plant.

7. The method of claim 6, wherein the nucleic acid is delivered into the plant by an *Agrobacterium*.

8. The method of claim 6, wherein the plant belongs to a genus selected from the group consisting of *Arabidopsis, Beta, Glycine, Helianthus, Solanum, Triticum, Oryza, Brassica, Medicago, Prunus, Malta, Hordeum, Musa, Phaseolus, Citrus, Piper, Sorghum, Daucus, Manihot, Capsicum*, and *Zea*.

9. The method of claim 6, wherein the variant confers phosphinothricin resistance in a plant, and comprises one substitution relative to SEQ ID NO: 1 or SEQ ID NO: 2, wherein the substitution is selected from: N35T, N35S, Y73F, T90A, Y92F, V125L, V125T, or V125I.

10. The host cell of claim 2, wherein the PAT protein variant confers phosphinothricin resistance in a plant, and comprises one substitution relative to SEQ ID NO: 2, wherein the substitution is selected from: N35T, N35S, Y73F, T90A, Y92F, V125L, V125T, or V125I.

11. The host cell of claim 2, wherein the host cell is a plant cell.

\* \* \* \* \*

SEQUENCE LISTING

<160> NUMBER OF SEQ ID NOS: 99

<210> SEQ ID NO 1
<211> LENGTH: 183
<212> TYPE: PRT
<213> ORGANISM: S. hygroscopicus

<400> SEQUENCE: 1

```
Met Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
                20                  25                  30

Thr Val Asn Phe Arg Thr Glu Pro Gln Glu Pro Gln Glu Trp Thr Asp
            35                  40                  45

Asp Leu Val Arg Leu Arg Glu Arg Tyr Pro Trp Leu Val Ala Glu Val
        50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
    130                 135                 140

Arg Gly Met Leu Arg Ala Ala Gly Phe Lys His Gly Asn Trp His Asp
145                 150                 155                 160
```

```
Val Gly Phe Trp Gln Leu Asp Phe Ser Leu Pro Val Pro Pro Arg Pro
                165                 170                 175

Val Leu Pro Val Thr Glu Ile
            180

<210> SEQ ID NO 2
<211> LENGTH: 183
<212> TYPE: PRT
<213> ORGANISM: S. viridochromogenes

<400> SEQUENCE: 2

Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
                20                  25                  30

Thr Val Asn Phe Arg Thr Glu Pro Gln Thr Pro Gln Glu Trp Ile Asp
            35                  40                  45

Asp Leu Glu Arg Leu Gln Asp Arg Tyr Pro Trp Leu Val Ala Glu Val
        50                  55                  60

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
                85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
        115                 120                 125

Pro Asn Asp Pro Ser Val Arg Leu His Glu Ala Leu Gly Tyr Thr Ala
130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                165                 170                 175

Val Arg Pro Val Thr Gln Ile
            180

<210> SEQ ID NO 3
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 3
attttgccga tttcggaac                                          19

<210> SEQ ID NO 4
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 4
atattgacca tcatactcat tgc                                     23

<210> SEQ ID NO 5
<211> LENGTH: 34
<212> TYPE: DNA
<213> ORGANISM: Artificial Sequence
```

```
<220> FEATURE:
<223> OTHER INFORMATION: oligonucleotide primer

<400> SEQUENCE: 5
gccttttcag aaatggataa atagccttgc ttcc                              34

<210> SEQ ID NO 6
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 6
tattgcctga tggatcgatt c                                            21

<210> SEQ ID NO 7
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 7
cagccattaa cttaggttgc g                                            21

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
agaacatgga tgtgccagaa g                                            21

<210> SEQ ID NO 9
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 9
cgctgcatat accatgtgat g                                            21

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 10
taaagggagc ttcgagtctc c                                            21

<210> SEQ ID NO 11
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 11
tcaccgcatc ttcctaaaat g                                            21
```

```
<210> SEQ ID NO 12
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 12
ccactagacc attggctttt tc                                              22

<210> SEQ ID NO 13
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 13
atcgatgatg tcttcgtgct c                                               21

<210> SEQ ID NO 14
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 14
aaaaccaaca aaaggcaatc c                                               21

<210> SEQ ID NO 15
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 15
cgagtgcgat acagagattc c                                               21

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 16
tgctcacttt ttcctttggt g                                               21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 17
caccatatgc aacacttgtg g                                               21

<210> SEQ ID NO 18
<211> LENGTH: 21
<212> TYPE: DNA
<213> ORGANISM: Artificial Sequence
<220> FEATURE:
<223> OTHER INFORMATION: oligonucleotide primer
```

<400> SEQUENCE: 18
ttttgtctca cctgcttcca c                                    21

<210> SEQ ID NO 19
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 19
tcatgaaggc acgtctttac c                                    21

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 20
tcaacagacc aaggtggaat c                                    21

<210> SEQ ID NO 21
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 21
ctcatcctgc tcttgacctt g                                    21

<210> SEQ ID NO 22
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 22
atagctagca tcggatgcaa c                                    21

<210> SEQ ID NO 23
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 23
tgtacaggtt atcggtgagc c                                    21

<210> SEQ ID NO 24
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 24
ttcaaatctc caattatttt gtttg                                25

```
<210> SEQ ID NO 25
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 25
aacaattccg atagtaccat ttcc                                            24

<210> SEQ ID NO 26
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 26
tttcatgaag ttgtcaacac ctg                                             23

<210> SEQ ID NO 27
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 27
ttgttgggag attttgtggt c                                               21

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
cattggttgc ttaattggtc c                                               21

<210> SEQ ID NO 29
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 29
gcatgaaagg ttctctttcc c                                               21

<210> SEQ ID NO 30
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 30
tcattctgcc ttctccatca g                                               21

<210> SEQ ID NO 31
<211> LENGTH: 21
<212> TYPE: DNA
<213> ORGANISM: Artificial Sequence
<220> FEATURE:
<223> OTHER INFORMATION: oligonucleotide primer
```

```
<400> SEQUENCE: 31
agcaacaacg atatttcgtg g                                              21

<210> SEQ ID NO 32
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 32
ccggaattca tgagcccaga acgacgcc                                       28

<210> SEQ ID NO 33
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 33
cccaagcttt cagatctcgg tgacgggc                                       28

<210> SEQ ID NO 34
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 34
acacggtcga ctgggccgtc cagtc                                          25

<210> SEQ ID NO 35
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 35
gtacacggtc gaatcggccg tccagtcg                                       28

<210> SEQ ID NO 36
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 36
gtacacggtc gacgcggccg tccagtc                                        27

<210> SEQ ID NO 37
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 37
cagcaggtgg gtgaagagcg tggagcc                                        27
```

```
<210> SEQ ID NO 38
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 38
gtgcatgcgc acggccgggt cgttgggc                                          28

<210> SEQ ID NO 39
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 39
cgagcgcctc gttcatgcgc acgct                                             25

<210> SEQ ID NO 40
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 40
ccgagcgcct cctgcatgcg cac                                               23

<210> SEQ ID NO 41
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 41
tccgagcgcc tcggccatgc gcacgctc                                          28

<210> SEQ ID NO 42
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 42
gcggctcggt acgggcgttg accgtgcttg                                        30

<210> SEQ ID NO 43
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 43
tcgccggcat cgccttcgcg ggcc                                              24

<210> SEQ ID NO 44
<211> LENGTH: 26
<212> TYPE: DNA
<213> ORGANISM: Artificial Sequence
<220> FEATURE:
<223> OTHER INFORMATION: oligonucleotide primer
```

```
<400> SEQUENCE: 44
gcgttgcgtg ccgcccaggg gcccgc                                          26

<210> SEQ ID NO 45
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 45
gtcgtaggcg ttggctgcct tccagggg                                        28

<210> SEQ ID NO 46
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 46
ccgtccagtc gaaggcgttg cgtgc                                           25

<210> SEQ ID NO 47
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 47
gggagacgta cacgaccgac tcggccgtcc                                      30

<210> SEQ ID NO 48
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 48
ggggagacga acacggtcga ctcggcc                                         27

<210> SEQ ID NO 49
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 49
gctcggtacg gaaggtgacc gtgcttgtc                                       29

<210> SEQ ID NO 50
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 50
gctcggtacg gaagctgacc gtgcttgtc                                       29
```

<210> SEQ ID NO 51
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 51
gagacgtaca cggccgactc ggccgtc                           27

<210> SEQ ID NO 52
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 52
gagacgtaca cgctcgactc ggccgtc                           27

<210> SEQ ID NO 53
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 53
gggagacgta cacgaccgac tcggccgtcc                        30

<210> SEQ ID NO 54
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 54
gggcagcccg atggtagcga ccacgctc                          28

<210> SEQ ID NO 55
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 55
gggcagcccg atgttagcga ccacgctc                          28

<210> SEQ ID NO 56
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 56
gcccgatgag agcgaccacg ctcttg                            26

<210> SEQ ID NO 57
<211> LENGTH: 32
<212> TYPE: DNA
<213> ORGANISM: Artificial Sequence
<220> FEATURE:
<223> OTHER INFORMATION: oligonucleotide primer

```
<400> SEQUENCE: 57
cagcccgatg atagcgacca cgctcttgaa gc                              32

<210> SEQ ID NO 58
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 58
gactggacgg cccagtcgac cgtgt                                      25

<210> SEQ ID NO 59
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 59
cgactggacg gccgattcga ccgtgtac                                   28

<210> SEQ ID NO 60
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 60
gactggacgg ccgcgtcgac cgtgtac                                    27

<210> SEQ ID NO 61
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 61
ggctccacgc tcttcaccca cctgctg                                    27

<210> SEQ ID NO 62
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 62
gcccaacgac ccggccgtgc gcatgcac                                   28

<210> SEQ ID NO 63
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 63
agcgtgcgca tgaacgaggc gctcg                                      25
```

```
<210> SEQ ID NO 64
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 64
gtgcgcatgc aggaggcgct cgg                                              23

<210> SEQ ID NO 65
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 65
gagcgtgcgc atggccgagg cgctcgga                                         28

<210> SEQ ID NO 66
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 66
caagcacggt caacgcccgt accgagccgc                                       30

<210> SEQ ID NO 67
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 67
ggcccgcgaa ggcgatgccg gcga                                             24

<210> SEQ ID NO 68
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 68
gcgggcccct gggcggcacg caacgc                                           26

<210> SEQ ID NO 69
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 69
cccctggaag gcagccaacg cctacgac                                         28

<210> SEQ ID NO 70
<211> LENGTH: 25
<212> TYPE: DNA
<213> ORGANISM: Artificial Sequence
<220> FEATURE:
<223> OTHER INFORMATION: oligonucleotide primer
```

<400> SEQUENCE: 70
gcacgcaacg ccttcgactg gacgg                                    25

<210> SEQ ID NO 71
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 71
ggacggccga gtcggtcgtg tacgtctccc                               30

<210> SEQ ID NO 72
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 72
ggccgagtcg accgtgttcg tctcccc                                  27

<210> SEQ ID NO 73
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 73
gacaagcacg gtcaccttcc gtaccgagc                                29

<210> SEQ ID NO 74
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 74
gacaagcacg gtcagcttcc gtaccgagc                                29

<210> SEQ ID NO 75
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 75
gacggccgag tcggccgtgt acgtctc                                  27

<210> SEQ ID NO 76
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 76
gacggccgag tcgagcgtgt acgtctc                                  27

```
<210> SEQ ID NO 77
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 77
ggacggccga gtcggtcgtg tacgtctccc                                            30

<210> SEQ ID NO 78
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 78
gagcgtggtc gctaccatcg ggctgccc                                              28

<210> SEQ ID NO 79
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 79
gagcgtggtc gctaacatcg ggctgccc                                              28

<210> SEQ ID NO 80
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 80
caagagcgtg gtcgctctca tcgggc                                                26

<210> SEQ ID NO 81
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 81
gcttcaagag cgtggtcgct atcatcgggc tg                                         32

<210> SEQ ID NO 82
<211> LENGTH: 43
<212> TYPE: DNA
<213> ORGANISM: Artificial Sequence
<220> FEATURE:
<223> OTHER INFORMATION: oligonucleotide primer

<400> SEQUENCE: 82
attttcaggg cgccatggat ccgatgggta gcccagaacg acg                             43

<210> SEQ ID NO 83
<211> LENGTH: 44
<212> TYPE: DNA
<213> ORGANISM: Artificial Sequence
<220> FEATURE:
<223> OTHER INFORMATION: oligonucleotide primer
```

<400> SEQUENCE: 83
catccgccaa aacagccaag cttttagatc tgtgtgacgg gccg        44

<210> SEQ ID NO 84
<211> LENGTH: 46
<212> TYPE: DNA
<213> ORGANISM: Artificial Sequence
<220> FEATURE:
<223> OTHER INFORMATION: oligonucleotide primer

<400> SEQUENCE: 84
cgattcatta atcactctgt ggtctcaaat gagcccagaa cgacgc      46

<210> SEQ ID NO 85
<211> LENGTH: 50
<212> TYPE: DNA
<213> ORGANISM: Artificial Sequence
<220> FEATURE:
<223> OTHER INFORMATION: oligonucleotide primer

<400> SEQUENCE: 85
ccactgaaga gccacttcgt ggtctcaaag ctcagatctc ggtgacgggc  50

<210> SEQ ID NO 86
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 86
cgattcatta atcactctgt ggtctcaaat gggtagccca gaacgacg    48

<210> SEQ ID NO 87
<211> LENGTH: 52
<212> TYPE: DNA
<213> ORGANISM: Artificial Sequence
<220> FEATURE:
<223> OTHER INFORMATION: oligonucleotide primer

<400> SEQUENCE: 87
ccactgaaga gccacttcgt ggtctcaaag cttagatctg tgtgacgggc cg  52

<210> SEQ ID NO 88
<211> LENGTH: 183
<212> TYPE: PRT
<213> ORGANISM: Streptomyces hygroscopicus

<400> SEQUENCE: 88

```
Met Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
                20                  25                  30

Thr Val Asn Phe Arg Thr Glu Pro Gln Glu Pro Gln Glu Trp Thr Asp
            35                  40                  45

Asp Leu Val Arg Leu Arg Glu Arg Tyr Pro Trp Leu Val Ala Glu Val
        50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95
```

```
His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
            115                 120                 125

Pro Asn Asp Pro Ser Val Arg Met His Glu Ala Leu Gly Tyr Ala Pro
            130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                    165                 170                 175

Val Leu Pro Val Thr Glu Ile
            180

<210> SEQ ID NO 89
<211> LENGTH: 183
<212> TYPE: PRT
<213> ORGANISM: Streptomyces viridochromogenes

<400> SEQUENCE: 89

Met Ser Pro Glu Arg Arg Pro Val Glu Ile Arg Pro Ala Thr Ala Ala
1               5                   10                  15

Asp Met Ala Ala Val Cys Asp Ile Val Asn His Tyr Ile Glu Thr Ser
                20                  25                  30

Thr Val Asn Phe Arg Thr Glu Pro Gln Thr Pro Gln Glu Trp Ile Asp
            35                  40                  45

Asp Leu Glu Arg Leu Gln Asp Arg Tyr Pro Trp Leu Val Ala Glu Val
        50                  55                  60

Glu Gly Val Val Ala Gly Ile Ala Tyr Ala Gly Pro Trp Lys Ala Arg
65                  70                  75                  80

Asn Ala Tyr Asp Trp Thr Val Glu Ser Thr Val Tyr Val Ser His Arg
                85                  90                  95

His Gln Arg Leu Gly Leu Gly Ser Thr Leu Tyr Thr His Leu Leu Lys
            100                 105                 110

Ser Met Glu Ala Gln Gly Phe Lys Ser Val Val Ala Val Ile Gly Leu
            115                 120                 125

Pro Asn Asp Pro Ser Val Arg Leu His Glu Ala Leu Gly Tyr Thr Ala
            130                 135                 140

Arg Gly Thr Leu Arg Ala Ala Gly Tyr Lys His Gly Gly Trp His Asp
145                 150                 155                 160

Val Gly Phe Trp Gln Arg Asp Phe Glu Leu Pro Ala Pro Pro Arg Pro
                    165                 170                 175

Val Arg Pro Val Thr Gln Ile
            180

<210> SEQ ID NO 90
<211> LENGTH: 189
<212> TYPE: PRT
<213> ORGANISM: Kitasatospora phosalacinea

<400> SEQUENCE: 90

Met Ser Thr Pro Glu Gln Arg Glu Gly Val Arg Leu Ala Arg Ala Glu
1               5                   10                  15

Asp Leu Pro Ala Val Cys Glu Ile Val Asn Phe Tyr Ile Arg Thr Ser
                20                  25                  30

Thr Val Asn Phe Arg Thr Ser Pro Gln Leu Pro Glu Glu Trp Glu Gln
            35                  40                  45
```

```
Asp Trp Ala Ala His Arg Glu Arg Tyr Pro Trp Tyr Val Ala Leu Val
     50                  55                  60

Gly Gly Glu Val Ala Gly Ile Ala Tyr Ala Ala Pro Trp Lys Ala Arg
 65                  70                  75                  80

Asn Ala Tyr Asp Trp Thr Thr Glu Thr Thr Val Tyr Val Ser Asp Arg
                 85                  90                  95

His Arg Gly Arg Gly Leu Gly Ser Ala Leu Tyr Glu Arg Leu Leu Lys
                100                 105                 110

Thr Leu Glu Ala Gln Gly Tyr Arg Ser Ala Met Ala Val Val Ser Leu
            115                 120                 125

Pro Asn Glu Gly Ser Val Ala Leu His Glu Ala Phe Gly Phe Glu Ser
        130                 135                 140

Val Gly Arg Ile His Ala Ala Gly His Lys Leu Gly Gly Trp His Asp
145                 150                 155                 160

Ile Gly Phe Trp Gln Arg Arg Phe Val Leu Asp Glu Asp Ala Pro Gly
                165                 170                 175

Pro Ile Thr Pro Leu Ala Asp Leu Ser Thr Glu Ala Pro
            180                 185

<210> SEQ ID NO 91
<211> LENGTH: 195
<212> TYPE: PRT
<213> ORGANISM: Streptomyces xiamenensis

<400> SEQUENCE: 91

Met Asn Val Met Thr Ala Ala Gly Ile Arg Phe Ala Thr Ala Glu Asp
 1               5                  10                  15

Leu Pro Ala Val Cys Ala Val Val Asn His Tyr Ile Glu Thr Thr Ala
             20                  25                  30

Ala Asn Phe Arg Thr Glu Pro Gln Pro His Glu Trp Leu Glu Gln
         35                  40                  45

Trp Glu Arg Gly His Arg Thr His Pro Trp Leu Val Ala Glu Val Asp
     50                  55                  60

Gly Glu Val Ala Gly Ile Ser Tyr Ala Phe Pro Trp Lys Ala Arg Ala
 65                  70                  75                  80

Ala Tyr Ala Trp Thr Val Glu Cys Ala Val Tyr Leu Ala Pro Gly Gln
                 85                  90                  95

His Gly Arg Gly Leu Gly Arg Ala Leu Tyr Glu Arg Leu Phe Ala Leu
                100                 105                 110

Leu Ser Glu Gln Gly Phe His Ser Val Ile Ala Gly Val Ala Leu Pro
            115                 120                 125

Asn Pro Ala Ser Glu Gly Leu His Arg Ser Leu Gly Phe Arg Gln Val
        130                 135                 140

Gly Thr Phe Arg Glu Asn Gly Tyr Lys Met Gly Ser Trp Arg Asp Val
145                 150                 155                 160

Ser Tyr Trp Gln Arg Pro Leu Ala Ala His Ser Gly Ala Pro Ala Pro
                165                 170                 175

Thr Ala Pro Ala Pro Thr Ala Pro Val Pro Ala Ala Gln Glu Ala Val
            180                 185                 190

Gly Ala Glu
        195

<210> SEQ ID NO 92
<211> LENGTH: 195
<212> TYPE: PRT
<213> ORGANISM: Salinispora tropica
```

```
<400> SEQUENCE: 92

Met Thr Val Arg Glu Ala Thr Ala Ala Asp Trp Pro Ala Val Thr Asp
1               5                   10                  15

Ile Val Asn His Tyr Ile Ala Thr Thr Thr Leu Asn Leu His Thr Glu
            20                  25                  30

Ala Arg Thr Leu Gln Asp Trp Thr Ala Asp Trp Thr Arg Tyr Arg Glu
        35                  40                  45

Arg Tyr Pro Trp Leu Val Ala Thr Asp Asp Arg Val Val Gly Val
    50                  55                  60

Ala Tyr Ala Gly Pro Trp Lys Ala Arg Asn Ala Tyr Asp Trp Cys Ala
65                  70                  75                  80

Glu Val Thr Gly Tyr Val Ser Thr Asp Met Arg Gly Arg Arg Val Gly
                85                  90                  95

His Ala Leu Tyr Arg Ser Leu Leu Ala Val Leu Asp Ala Gln Gly Phe
            100                 105                 110

Arg Ser Gln Ile Ala Val Ile Gly Leu Pro Asn Asp Pro Ser Ala Gly
        115                 120                 125

Phe His Glu Ser Phe Gly Phe Arg His Val Gly Thr Leu Ala Gly Val
130                 135                 140

Gly Phe Lys Asn Gly Thr Trp Leu Asp Val Gly Phe Trp Gln Arg Ser
145                 150                 155                 160

Ala Gly Asp Thr Ser Gln Ala Pro Asp Pro Leu Leu Pro Cys Ala Asp
                165                 170                 175

Val Leu Lys Glu Val Leu Asp Ala Val Gly Arg Glu Arg Ala Pro Val
            180                 185                 190

Gln Arg Arg
        195

<210> SEQ ID NO 93
<211> LENGTH: 161
<212> TYPE: PRT
<213> ORGANISM: Owenweeksia hongkongensis

<400> SEQUENCE: 93

Met Leu Arg Pro Val Asn Leu Asn Asp Ala Pro Ala Ile Ala Glu Ile
1               5                   10                  15

Tyr Asn His Tyr Val Arg Glu Thr Ile Thr Phe Glu Glu Ile Glu
            20                  25                  30

Ile Asp Ala Ala Glu Ile Glu Lys Arg Ile Glu Ile Thr Ala Lys
        35                  40                  45

Tyr Pro Trp Ile Val Phe Glu Glu Asp Gly Glu Ile Leu Gly Tyr Ala
    50                  55                  60

Tyr Ala Gly Glu Trp Arg Thr Arg Ser Ala Tyr Arg Phe Val Ala Glu
65                  70                  75                  80

Ser Ala Val Tyr Leu Lys His Asp Leu Pro Pro Lys Gly Ile Gly Ser
                85                  90                  95

Leu Leu Tyr Ala Glu Leu Leu Gln Lys Leu Lys Ala Gln Gly Ile His
            100                 105                 110

Ala Val Met Gly Val Leu Gly Leu Pro Asn Glu Pro Ser Ile Lys Leu
        115                 120                 125

His Glu Lys Phe Gly Phe Lys Lys Val Ala His Phe Lys Glu Val Gly
130                 135                 140
```

```
Phe Lys Phe Glu Lys Trp Val Asp Val Gly Tyr Trp Gln Leu Thr Phe
145                 150                 155                 160

Asp

<210> SEQ ID NO 94
<211> LENGTH: 164
<212> TYPE: PRT
<213> ORGANISM: Vibrio diazotrophicus

<400> SEQUENCE: 94

Met Leu Ile Arg Lys Val Ser Ser Asp Ile Asp Ser Met Ala Arg
1               5                   10                  15

Ile Tyr Asn His Tyr Ile Ala Thr Thr Thr Ile Ser Phe Glu Glu Leu
                20                  25                  30

Pro Val Ser Thr Glu Glu Met Thr Asn Arg Val Glu Asn Val Leu Ser
            35                  40                  45

Leu Gly Leu Pro Trp Ile Val Leu Glu Gln Asp Gly Glu Val Arg Gly
        50                  55                  60

Tyr Ala Tyr Ala Asn Gln Trp Lys Ala Arg Ser Ala Tyr Arg Tyr Thr
65                  70                  75                  80

Val Glu Pro Ser Ile Tyr Val Ala His Glu Met Lys Gly Lys Gly Ile
                85                  90                  95

Gly Arg Leu Leu Tyr Gly Glu Leu Leu Glu Ile Leu Lys Ser Ala Gly
            100                 105                 110

Phe Lys Asn Ala Val Gly Ser Ile Ala Leu Pro Asn Pro Ser Ser Val
        115                 120                 125

Ala Leu His Glu Arg Met Gly Phe Lys Lys Val Gly Glu Phe Asn Asn
    130                 135                 140

Ile Gly Phe Lys Phe Asp Gln Gln Ile Ser Val Gly Tyr Trp Gln Leu
145                 150                 155                 160

Glu Phe Asn Ser

<210> SEQ ID NO 95
<211> LENGTH: 197
<212> TYPE: PRT
<213> ORGANISM: Alcaligenes faecalis

<400> SEQUENCE: 95

Met Pro Ser Ser Ser His Pro Ser Thr Pro Asp Ala Pro Gln Arg
1               5                   10                  15

Val Gly Val Glu Leu Ala Arg Cys Ala Cys Thr Val Arg Val Arg
                20                  25                  30

Asp Asp Asp Leu Pro Ala Ile Thr Ala Ile Tyr Ala His His Val Arg
            35                  40                  45

Thr Gly Thr Ala Ser Phe Glu Glu Val Pro Pro Asp Asp Thr Glu Met
        50                  55                  60

Arg Ala Arg Cys Ala Lys Val Leu Asp Ala Gly Leu Pro Tyr Leu Val
65                  70                  75                  80

Ala Glu Arg Asp Gly Lys Leu Leu Gly Tyr Ala Tyr Ala Thr His Tyr
                85                  90                  95

Arg Pro Arg Ser Ala Tyr Arg Phe Thr Leu Glu Asp Ser Val Tyr Ile
            100                 105                 110

Ala Pro Asp Ala Ile Gly Gln Gly Val Gly Arg Thr Leu Leu Leu Thr
        115                 120                 125

Leu Ile Ala Arg Cys Glu Gly Gly Pro Trp Arg Gln Leu Ile Ala Asn
    130                 135                 140
```

Val Gly Asp Ser Gly Asn Thr Ala Ser Leu Gly Leu His Ala Ala Cys
145                 150                 155                 160

Gly Phe Val Gln Ala Gly Val Leu Lys Ser Val Gly Phe Lys Phe Gly
                165                 170                 175

Arg Trp Ile Asp Thr Val Leu Met Gln Arg Pro Leu Asn Ala Gly Asp
            180                 185                 190

Thr Thr Leu Pro Glu
            195

<210> SEQ ID NO 96
<211> LENGTH: 179
<212> TYPE: PRT
<213> ORGANISM: Sphingomonas wittichii

<400> SEQUENCE: 96

Met Ala Gly Ala Leu Ile Val Arg Asp Ala Ser Pro Asp Asp Ala Ala
1               5                   10                  15

Ala Ile Ala Ala Ile Tyr Ala Pro Tyr Val His Asp Thr Val Ile Thr
                20                  25                  30

Phe Glu Ile Asp Ala Pro Asp Ala Ala Glu Met Arg Asn Arg Ile Val
            35                  40                  45

Glu Thr Ser Ala Arg Phe Pro Trp Leu Val Ala Glu Ser Gly Ala
    50                  55                  60

Val Cys Gly Tyr Ala Tyr Ala Thr Ser Phe Arg Ala Arg Ala Ala Tyr
65                  70                  75                  80

Arg Trp Val Ala Glu Thr Thr Val Tyr Ile Ala Asp Gly Phe His Arg
                85                  90                  95

Arg Gly Ile Gly Arg Ala Leu Tyr Ala Pro Leu Leu Asp Arg Leu Glu
            100                 105                 110

Arg Gln Gly Tyr Gln Ala Ala Ile Gly Ala Ile Ala Leu Pro Asn Ala
        115                 120                 125

Gly Ser Val Gly Leu His Glu Ala Met Gly Phe Val His Gln Gly Leu
130                 135                 140

Tyr Arg Gln Val Gly Phe Lys Leu Asp Gly Trp His Asp Val Gly Leu
145                 150                 155                 160

Trp Gln Arg Asp Phe Gly Glu Arg Pro Ala Arg Pro Thr Glu Pro Leu
                165                 170                 175

Ser Pro Leu

<210> SEQ ID NO 97
<211> LENGTH: 185
<212> TYPE: PRT
<213> ORGANISM: Ponticaulis koreensis

<400> SEQUENCE: 97

Met Ile Ile Arg Phe Ala Thr Ala Ala Asp Pro Lys Ile Ala Glu
1               5                   10                  15

Ile Tyr Ala Pro Phe Val Asp Gly Ser Ala Val Ser Phe Glu Met Glu
                20                  25                  30

Pro Pro Ala Ala Asp Ile Met Ala Gly Arg Ile Glu Lys Leu Trp Pro
            35                  40                  45

Thr His Pro Trp Ile Val Ala Glu Asp Glu Gly Glu Val Val Gly Tyr
    50                  55                  60

Ala Tyr Gly Ser Pro Tyr Arg Glu Arg Lys Ala Tyr Gln Trp Ala Val
65                  70                  75                  80

Glu Val Thr Val Tyr Leu Ala Pro Ala Ala Arg Gly Lys Gly Leu Gly
                85                  90                  95

Arg Lys Leu Tyr Asn Val Leu Ile Asp Ile Leu Thr Gln Gly Phe
            100                 105                 110

Thr Lys Ala Tyr Gly Val Val Thr Leu Pro Asn Ala Gly Ser Ala Ala
            115                 120                 125

Leu His Glu Ala Val Gly Phe His His Phe Ala Thr Tyr Arg Asn Ile
130                 135                 140

Gly Phe Lys Asn Gly Ser Trp His Asp Val Gly Trp Trp Glu Arg Asp
145                 150                 155                 160

Leu Ala Pro Cys Ile Val Pro Gln Pro Asp Leu Lys Thr Leu Thr Glu
                165                 170                 175

Leu Gly Tyr Ser Glu Gly Gly Ser Val
            180                 185

<210> SEQ ID NO 98
<211> LENGTH: 182
<212> TYPE: PRT
<213> ORGANISM: Pseudomonas syringae

<400> SEQUENCE: 98

Met Ser Lys Thr Thr Val Arg Ile Ala Gln Val Ser Asp Ala Gln Ala
1               5                   10                  15

Ile Gln Ala Ile Tyr Ala Pro Met Val Glu Ser Thr Thr Ile Ser Phe
            20                  25                  30

Glu Leu Glu Pro Pro Ser Val Glu Glu Met Ala Met Arg Ile Glu Ser
            35                  40                  45

Thr Leu Leu Thr Tyr Pro Tyr Leu Val Ala Val Arg Asp Gly Gln Val
50                  55                  60

Ile Gly Tyr Ala Tyr Ala Ser Gln His Arg Ala Arg Glu Ala Tyr Arg
65                  70                  75                  80

Trp Ser Val Asp Val Thr Val Tyr Ile Ser Pro Glu Ala His Arg Ser
                85                  90                  95

Gly Val Gly Arg Ala Leu Tyr Asp Val Leu Leu Pro Thr Leu Lys Lys
            100                 105                 110

Gln Gly Phe His Ala Ala Tyr Ala Gly Ile Ala Leu Pro Asn Asp Gly
            115                 120                 125

Ser Val Gly Leu His Glu Ala Leu Gly Phe Ala His Ile Gly Thr Tyr
130                 135                 140

Pro Glu Val Gly Phe Lys His Gly Ala Trp Arg Asp Val Gly Tyr Trp
145                 150                 155                 160

Arg Ile Ala Leu Asp Ser Thr Asn Pro Pro Lys Leu Pro Val Leu Phe
                165                 170                 175

Ser Glu Ile Ser Leu Phe
            180

<210> SEQ ID NO 99
<211> LENGTH: 190
<212> TYPE: PRT
<213> ORGANISM: Sphingobium herbicidovorans

<400> SEQUENCE: 99

Met Leu Thr Leu Arg Lys Ala Val Val Glu Asp Gly Ala Ala Leu Ala
1               5                   10                  15

Ala Ile Tyr Ala Pro Tyr Val Leu Asp Thr Val Ile Ser Phe Glu Ala
            20                  25                  30

```
Val Pro Pro Thr Ala Glu Glu Phe Gly Gly Arg Ile Ala Asn Cys Leu
    35                      40                  45

Pro Asn Tyr Pro Trp Leu Val Ala Glu Leu Asp Gly Gln Val Ala Gly
    50              55                  60

Tyr Ala Tyr Ala Gly Pro His Ser Gly Arg Ala Ala Tyr Asn Trp Ser
65              70                  75                      80

Ala Asp Ile Ser Val Tyr Leu Ala Pro Asp His His Arg Arg Gly Ile
            85                  90                  95

Gly Arg Ser Leu Tyr Asp Ala Leu Ile Ala Leu Leu Arg Arg Gln Gly
            100                 105                 110

Tyr His Ala Leu Phe Ala Gly Ile Thr Leu Pro Asn Glu Ala Ser Val
        115                 120                 125

Ala Ile His Ser Ala Ile Gly Met Arg Gln Val Gly Ile Tyr Arg Glu
        130                 135                 140

Val Gly Phe Lys Phe Gly Gln Trp His Asp Val Met Trp Met Gly Met
145                 150                 155                 160

Thr Ile Ser Pro Arg Ala Gln Pro Met Ser Ala Pro Thr Pro Phe Ser
                165                 170                 175

Ala Leu Thr Asn Leu Gln Asp Ile Val Pro His Leu Thr Gly
            180                 185                 190
```